(12) United States Patent
Wu et al.

(10) Patent No.: US 8,367,822 B2
(45) Date of Patent: Feb. 5, 2013

(54) COMPOSITIONS AND METHODS FOR BONE FORMATION AND REMODELING

(75) Inventors: Dianqing (Dan) Wu, Cheshire, CT (US); Dakai Liu, South Setauket, NY (US); James J. Donegan, Long Beach, NY (US)

(73) Assignee: Enzo Therapeutics, Inc., Farmingdale, NY (US)

( * ) Notice: Subject to any disclaimer, the term of this patent is extended or adjusted under 35 U.S.C. 154(b) by 1141 days.

(21) Appl. No.: 11/598,916

(22) Filed: Nov. 14, 2006

(65) Prior Publication Data
US 2010/0298308 A1 Nov. 25, 2010
US 2012/0178747 A9 Jul. 12, 2012

Related U.S. Application Data

(63) Continuation-in-part of application No. 11/097,518, filed on Apr. 1, 2005, which is a continuation-in-part of application No. 11/084,668, filed on Mar. 18, 2005, which is a continuation-in-part of application No. 10/849,067, filed on May 19, 2004.

(60) Provisional application No. 60/504,864, filed on Sep. 22, 2003.

(51) Int. Cl.
*C07D 265/34* (2006.01)
*C07D 498/02* (2006.01)
*C07D 498/12* (2006.01)
*C07D 265/38* (2006.01)

(52) U.S. Cl. .................................. 544/101; 544/102
(58) Field of Classification Search .................. 544/101, 544/102
See application file for complete search history.

(56) References Cited

U.S. PATENT DOCUMENTS

| 6,844,422 B1 | 1/2005 | Niehrs et al. |
|---|---|---|
| 2003/0165500 A1 | 9/2003 | Rhee |
| 2003/0181660 A1 | 9/2003 | Todd et al. |
| 2004/0009535 A1 | 1/2004 | Brunkow |
| 2004/0023356 A1 | 2/2004 | Krumlauf |
| 2004/0038860 A1 | 2/2004 | Allen |
| 2004/0235728 A1 | 11/2004 | Stoch |
| 2005/0043385 A1 | 2/2005 | Guy |
| 2005/0084494 A1 | 4/2005 | Prockop |
| 2005/0196349 A1 | 9/2005 | Wu et al. |
| 2005/0261181 A1 | 11/2005 | Wu et al. |
| 2006/0127393 A1 | 6/2006 | Li et al. |
| 2006/0257892 A1 | 11/2006 | Cohen et al. |

OTHER PUBLICATIONS

Dostal et al. 1982, "Acid-Base Equilibria of some 7-dimethylamino-3-phenoxazone derivative." Collection Czechoslovak Chem. Commun, vol. 47, pp. 1588-1598.*

Lars Grotewold and Ulrich Ruther, Bmp, Fgf and Wnt signaling in programmed cell death and chondrogenesis during vertebrate limb development: the role of Dickkopf-1, Int J. Dev. Biol., 2002, 943-947, 46.
Carl Gregory, The Wnt signaling inhibitor Dickkopf-1 is required for reentry into the cell cycle of human adult stem cells from bone marrow, Journal of Biological Chemistry, 2003, 28067-28078, 278(30).
2001 NIH Consensus Conference Development Panel on Osteoporosis Prevention, Diagnosis and Therapy. JAMA 285:785-795.
Axford, John S. Glycobiology & Medicine: A Millenial Review, Jul. 11-12, 2000 lecture at 5$^{th}$ Jenner Symposium held at Royal Society of Medicine, London, UK, http://www/glycoscience.com/glycoscience/document_viewer.wm?FILENAME=D006.
Babij et al., 2003, J Bone Miner Res 18:960-74.
Bafico et al., 2001, Nat Cell Biol 3:683-6.
Bain et al., 2003, Biochem Biophys Res Commun 301:84-91.
Barrandon, Yann Mar. 20, 2003, Nature vol. 422:272-273.
Boyden et al., May 16, 2002, N Engl J Med 346(20):1513-21.
Capelluto et al. 2002, Nature 419(6908):726-9.
Cheyette et al. 2002, Dev Cell, vol. 2, 449-461.
Clark et al. 2002, J. Mol. Graph.
Culi et al. 2003, Cell 112:343-54.
Dale et al. 1998, 329:209-223.
Daniels et al 2002, 10(3):573-84.
Dann et al. 2001, Nature, vol. 412, 86-90.
Erickson et al. Mar. 1973, Journal of Lipid Research, vol. 14:133-137.
Gao, Yuan et al., May 18, 2004, PNAS, vol. 101, No. 20, pp. 7618-7623.
Glinka et al, 1998, Nature 391(6665):357-62.
Glinka et al, Jun. 10, 2002, DKFZ 2001: Research Report 1999/2000: 36-40.
Gong et al. 2001, Cell 107:513-23.
Gumbiner et al. 1998, 8:430-5 Curr Opin Genet Dev.

(Continued)

*Primary Examiner* — Sreeni Padmanabhan
*Assistant Examiner* — Kara R McMillian
(74) *Attorney, Agent, or Firm* — Elie Gendloff, Esq.

(57) ABSTRACT

The mechanism by which the high bone mass (HBM) mutation (G171V) of the Wnt coreceptor LRP5 regulates the canonical Wnt signaling was investigated. The mutation was previously shown to reduce Dkk protein-1-mediated antagonism, suggesting that the first YWTD repeat domain where G171 is located may be responsible for Dkk protein-mediated antagonism. However, we found that the third YWTD repeat, but not the first repeat domain, is required for DKK1-mediated antagonism. Instead, we found that the G171V mutation disrupted the interaction of LRP5 with Mesd, a chaperon protein for LRP5/6 that is required for the coreceptors' transport to cell surfaces, resulting in less LRP5 molecules on the cell surface. Although the reduction in the level of cell surface LRP5 molecules led to a reduction in Wnt signaling in a paracrine paradigm, the mutation did not appear to affect the activity of coexpressed Wnt in an autocrine paradigm. Together with the observation that osteoblast cells produce autocrine canonical Wnt, Wnt7b, and that osteocytes produce paracrine Dkk1, we believe that the G171V mutation may cause an increase in Wnt activity in osteoblasts by reducing the number of targets for paracrine Dkk1 to antagonize without affecting the activity of autocrine Wnt.

17 Claims, 32 Drawing Sheets

OTHER PUBLICATIONS

Guo, Nini et al. Jun. 22, 2004, vol. 101, No. 25, pp. 9277-9281.
Graham et al. 2000 Cell. 103(6):885-96.
Gruneberg, et al. 2001, Angew. Chem. Int. Ed Engl. 40, 389-393.
Hey et al. 1998. Gene 216, 103-11.
Hsieh et al. 2003, Cell 112:355-67.
Hsu et al. 1998, Molecular and Cellular Biology 18:4807-4818.
Hurst 1994 J. Chem. Inf. Comput. Sci. 34, 190-196.
Jeon et al. 2001, Nat Struct Biol 8:499-504.
Kalajzic et al. 2002, J Bone Miner Res 17(1):15-25.
Kannus et al. 2000, Osteoporos Int 11:443-8.
Kato et al. 2002, J Cell Biol 157(2):303-14.
Krupnik et al. 1999, Gene 238:301-13.
Leyns et al. 1997, Cell, vol. 88, 747-756.
Li et al. 2002, J Biol Chem 277(8):5977-81.
Li et al. 1999, EMBO J 18:4233-4240.
Li et al. 1999, J. Biol. Chem. 274:129-134.
Lilien, Ryan H. et al., Mar. 4, 2004 Dartmouth Computer Science Dept. Technical Report No. TR2004-492 at http://www.cs.dartmouth.edu/reports/reports.html.
Lips, 1997, Am J Med 103:3S-8S; discussion 8S-11S.
Little et al. 2002, Am J Hum Genet 70:11-9.
Love et al, 1995, Nature. 376(6543):791-5.
Mao et al. 2002, Nature 417:664-7.
Mao et al, Nature vol. 411:321-5, (2005).
Mao et al, 2001, Mol Cell 7:801-9.
Monaghan 1999, Mech Dev 87:45-56.
Moon RT et al, 1997, Cell, vol. 88, 725-728.
Nusse 2001, Nature 411:255-6.
Pandur et al, 2001, Bioessays 23:207-10.
Pfaffl 2001, Nucleic Acids Res May 1, 2001;29(9):e45.
Pinson et al, 2000, Nature 407:535-538.
Poy 2001, Nat Struct Biol. 8(12):1053-7.
Rarey et al, 1996 J. Mol. Biol. 261: 470-479.
Reddy, Seshamma T., et al. 2004 J Invest Dermatol 123:275-282.
Schweizer et al, 2003, BMC Cell Biol 4:4.
Semenov et al, 2001, Curr Biol 11: 951-61.
Szilagyi, Andras et al., Phys.Biol. 2 (2005) 1-16.
Takagi et al, 2003, Nature 424:969-74.
Tamai et al, 2000, Nature 407:530-5.
Tamai et al, 2004, Molecular Cell, vol. 13, 149-156.
Tolwinski et al, 2003, et al, Dev Cell 4:407-18.
Toogood, Peter L. Apr. 11, 2002, Journal of Medicinal Chemistry vol. 45, No. 8, pp. 1543-1558.
Van Wesenbeeck et al, 2003, Am J Hum Genet 72:763-71.
von Kries et al, 2000, Nat Struct Biol. 7(9):800-7.
Waszkowycz, et al, 2001, IBM Systems J. 40, 360-376.
Wang, et al., 2005 Journal of Medicinal Chemistry, vol. 48, No. 7, 2432-2444.
Wehrli, et al, 2000, Nature 407:527-30.
Wharton 2003, Dev Biol. 253(1):1-17.
Wodarz 1998, Annu. Rev. Cell Dev. Biol. 14:59-88.
Wong et al, 2003, Mol Cell. 12(5):1251-60.
Wong et al, 2000, Nat Struct Biol. 7(12):1178-84.
Xing Y et al, 2003, Genes Dev. Nov. 15, 2003;17(22):2753-64.
Wang et al., Am Chem Society, 2004.
Zuckerman 1996, N Engl J Med 334:1519-25.
Reya et al, 2005 Nature 434: 843.
Kleber et al, 2004 Curr Opin Cell Biol 16:681.
Logan et al, 2004 Annu Rev Cell Dev Biol 20: 781.
Sancho et al, 2004 Annu Rev Cell Dev Biol 20: 695-723.
Wang et al, 2004 Curr Opin Genet Dev 14: 533.
Moon et al, 2004, Nat Rev Genet 5:691.
Kawano et al, 2003, J Cell Sci 116: 2627.
Zhang et al., 2004, Mol Cell Biol 24:4677-4684.
Fujino et al., 2003, Proc Natl Acad Sci USA 100: 229.
Yamazaki et al, 2003, Biochem Biophys Res Commun 304: 229.
Hoffmann et al., 1999, J Med Chem 42: 4422.
Kramer 1999, Proteins 37: 228.
Mundy et al., 1999, Science 286: 1946.
Dunstan et al., 1999, J Bone Miner Res 14:953.
Li, et al, 2001, Cell Mol Life Sci 58: 2085.
Smith, 1999, Trends Biochem Sci 24: 181.
Yuan et al, 1999, J. Biol. Chem. 274: 30419-30423.
Li et al, 2002, JBC 277; 5977-5981.
Li et al., 2005, JBC vol. 280, No. 20, 19883-19887.
Wei et al. 2006, Cell 124; 1141-1154.
Johnson et al., 2004, J Bone Disease and Mineral Research 19; 1749-1757.
Hay et al. 2005, JBC 280; 13616-13623.
Kikuchi et al., 2006, Exp Molec. Med 38; 1-10.
Semenov et al. 2005, JBC 280; 26770-26775.
Logan et al, Annu. Rev. Cell Dev. Biol 20; 781-810, (2004).
Streeten et al., 2008, Bone 43(2008) 584-590.
Krane 2005, J Exp Med 201; 841-843.
Krishnan et al., 2006, J Clin Invest 116; 1202-1.
Liang et al., 2003, Cancer Cell 4:349-360.
Weeraratna et al., 2002, Cancer Cell 1:279-288.
Polakis 2000 Genes Dev 14: 1837-1851.
Behrens and Lustig 2004 Int J Dev Biol 48: 477-487.
Luu et al., 2004 Curr Cancer Drug Targets 4; 653-671.
Bafico et al., 2004 Cancer Cell 6; 497-506.
Janssens et al., 2006 Investigational New Drugs 24; 263-280.
Tian et al. 2003 NEJM 349: 2483-2494.
Oshima et al., 2005 Blood 106: 3160-3165.
Toomes et al., 2004 Am. J. Hum. Genet. 74: 751-730.
Niemann et al., 2004 Am J. Hum. Genet 74: 558-563.
Grant et al., 2006, Nature Genetics 38: 320-323.
Rodova et al., 2002 J. Biol. Chem 277: 29577-29583.
Surendran et al., Am J Physiol Renal Physiol 282: F431-F441, (2002).
Chilosi et al., 2003, Am J. Pathol. 162: 1495-1502.
Cheon et al., 2002 Proc. Nat, Acad. Sci. (USA) 99: 6973-6978.
Miyaoka et al., 1999 Schizophr. Res. 38:1-6.
Symolon et al. 2004 J. Nutr. 134: 1157-1161.
Chen H. et al. Cell 84: 491-495, 1996.
Lee G.H. Nature 379: 632-635, 1996.
Nusse and Varmus 1982, Cell 31:99-109.
Couso et al., 1995 Development 120: 621-636.
Mukhopadhyay et al., 2001 Dev Cell 1:423-434.
Li et al., 2005 Nature Genetics 37:945-952.
Mukhopadhyay et al., 2006 Development 133:2149-2154.
Pinson et al., 2000 Nature 407:535-538.
Kelly et al., Development 131:2803-2815, (2004).
Magoori et al., 2003 J Biol Chem 278:11331-11336.
Van Amerongen and Burns, 2006 Trends Genet 12:678-389.
Bockamp et al., 2002 Physiol Genomics 11:115-132.
Raport et al., 1996 J. Biol Chem 271:17161-17166.
Deng et al., 1996 Nature 382:661-666.
Dragic et al., 1996 Nature 381-667-673.
Abrami et al., 2003 J. Cell Biol 160:321-328.
Bradley et al., 2001, Nature 414:225-229.
Scobie et al., 2003 Proc Nat Acad Sci USA 100:5170-5174.
Molloy et al., 1992 J. Biol Chem 267:16396-16402.
Petosa et al., 1997 Nature 385:833-838.
Chauhan and Bhatnagar 2002, Infect Immunol 70:4477-4484.
Cunningham et al., 2002 Proc Nat Acad Sci USA 99:7049-7083.
Pannifer et al., 2001 Nature 414:229-233.
Elliot et al., 2000 Biochemistry 39:6706-6713.
Lacy et al.,2002 J. Biol. Chem. 277:3006-3010.
Rosovitz et al., 2003 J. Biol. Chem. 278:30936-30944.
Little et al., 1988 Infect Immun 56:1807-1813.
Lacy et al., 2004 Proc Nat Acad Sci USA 13147-13151.
Liu et al., Apr. 2007 Cell Microbiol 9(4):977-987.
Moayeri et al., 2006 Antimicrob Agents and Chemotherapy 50:2658-2665.
Schepetkin et al., 2006 J. Med. Chem. 49:5232-5244.
Goldman et al., 2006 BMC Pharmacology 6:8-15.
Panchal et al., 2004 Nat Struct Mol Biol 11:67-72.
Forino et al., 2005 Proc Nat Acad Sci USA 102:9499-9504.
Johnson et al., 2006 J. Med. Chem. 12:27-30.
Turk et al., 2004 Nat Struct Mol Biol 11:60-66.
Kocer et al., 2005 Infection and Immunity 73:7548-7557.
Karginov et al., 2005 Proc Nat Acad Sci USA 102:15075-15080.
Opal et al., 2005 Infect Immun 73:5101-5105.

Komiyama et al., 2005 Antimicrob Agents Chemotherapy 49:3875-3882.
Basha et al., 2006 Proc Nat Acad Sci USA 103:13509-13513.
E.L. Eliel & S.H. Wilen, Stereochemistry of Carbon Compounds, John Wiley & Sons, New York, NY, 1994, pp. 1119-1190.
Simon-Chazottes et al., 2006 Genomics 87:673-677.
Erlanson et al., 2004 J. Med Chem. 47:3463-3482.
Erlanson, 2006 Curr Opin Biotech 17:643-652.
Morrisey, 2003 Am J Path 162:1393-1397.
Pongracz and Stockley 2006 Respiratory Research 7:15.
Tickenbrock 2006 J Leuk Biol 79:1306-1311.
Figueroa et al., 2000 J. Histochem & Cytochem, 48(10):1357-1368.
Sen et al., 2000 Proc Nat Acad Sci USA 2791-2796.
Nakamura et al., 2005 Am J Path 167:97-105.
Gustafson and Smith 2006 J. Biol Chem 281:9507-9516.
Cawthorn et al., 2007 Cell Death Differ 14:1361-1373.
Diarra et al., 2007 Nature Medicine 13:156-163.
Rothbacher and Lemaire 2002 Nature Cell Biology 4:E172-E173.
Liu et al., 2003 Molec and Cell Biol 23:5825-5835.
Mi and Johnson, J.Cell Biochem 95:328-338, (2005).
Andl et al., 2002 Developmental Cell 2:643-653.
Sick et al., 2006 Science 1447-1450.
Papakonstantinou et al., J. Invest Dermatol 125:673-684, (2005).
Tamamura et al., 2005 J. Biol Chem. 280:19185-19195.
Hertz and Strickland, 2001 J. Clin. Invest. 108:779-784.
Zeng et al. 2008 Development 135:367-375.
Nam et al., 2006 JBC 281(19):13247-13257.
Mercurio et al., 2003 Development 131:2137-2147.
Davidson et al., Nature 438:867-872, (2005).
Swiatek et al., 2006 J. Biol Chem 281:12233-12241.
Mi et al., JBC 281:4787-4794, (2006).
Zeng et al., Nature 438:873-877, (2005).
Zilberberg et al., 2004 J. Biol Chem 279:17535-17542.
Guo et al., 2006 J Med Genet 43:798-803.
Mani et al., 2007 Science 315:1278-1282.
He et al., 2005 Development 131:1663-1677.
Wu et al., 2000 Curr Biol 10:1611-1614.
Zorn, 2001, Curr Biol 11:R592-R595.
Brott and Sokol, 2002 Molec and Cell Biol 22:6100-6110.
Mikels and Nusse, 2006 PloS 4:0570-0582.
Johnson et al., 2006 Genomics 88:600-609.
Pukrop et al., 2006 Proc Natl Acad Sci USA 103:5454-5459.
Lin et al., 1994 Anal Record 240:492-506.
Miyauchi et al., 2001 Histochem Cell Biol 116:57-62.
Elbashir, S. M. et al. Duplexes of 21-nucleotide RNAs mediate RNA interference in cultured mammalian cells. *Nature* 411, 494-8 (2001).
Brummelkamp, T. R., Bernards, R. & Agami, R. A system for stable expression of short interfering RNAs in mammalian cells. *Science* 296, 550-3 (2002).
Kahler, R. A. & Westendorf, J. Lymphoid enhancer factor-1 and beta-catenin inhibit Runx2-dependent transcriptional activation of the osteocalcin promoter. *J Biol Chem* vol. 278, No. 14, 11937-44 (2003).
Mundlos, S. et al. Mutations involving the transcription factor CBFA1 cause cleidocranial dysplasia. *Cell* 89, 773-9 (1997).
Otto, F. et al. Cbfa1, a candidate gene for cleidocranial dysplasia syndrome, is essential for osteoblast differentiation and bone development. *Cell* 89, 765-71 (1997).
Komori, T. et al. Targeted disruption of Cbfa1 results in a complete lack of bone formation owing to maturational arrest of osteoblasts. *Cell* 89, 755-64 (1997).
Ducy, P., Zhang, R., Geoffroy, V., Ridall, A. 1. & Karsenty, G. Osf2/Cbfa1 : a transcriptional activator of osteoblast differentiation. *Cell* 89, 747-54 (1997).
Pandur, P., Lasche, M., Eisenberg, 1. M. & Kuhl, M. Wnt-11 activation of a non-canonical Wnt signaling pathway is required for cardiogenesis. *Nature* 418, 636-41 (2002).
Zhang, J, et al. Identification of the haematopoietic stem cell niche and control of the niche size. Nature 425, 836-841 (2003).
Itoh, K., Antipova, A., Ratcliffe, M. J. & Sokol, S. Interaction of dishevelled and Xenopus axin-related protein is required for Wnt signal transduction. *Mol Cell Biol* vol. 20, No. 6, 2228-38 (2000).
Calvi, L, et al. Osteoblastic cells regulate the haematopoietic stem cell niche. Nature 425, 841-846 (2003).
Li, Song et al., A computer screening approach to immunoglobulin superfamily atructures and interactions: Discovery of small non-peptidic CD4 inhibitors as novel immunotherapeutics, Proc Natl Acad Sci USA vol. 94, pp. 73-78, Jan. 1997.
Willert, K, et al. Wnt proteins are lipid-modified and can act as stem cell growth factors. Nature 423, 448-452 (2003).
Gregory, C, et al. The Wnt signaling inhibitor Dickkopf-1 is required for re-entry into the cell cycle of human adult stem cells from bone marrow. The Journal of Biological Chemistry 278, (30):28067-28078 (2003).
Teitelbaum, S, et al. Genetic Regulation of osteoclast development and function. Nature Genetics 4, 638-649 (2003).
Prockop, D, et al. One strategy for cell and gene therapy: Harnessing the power of adult stem cells to repair tissues. PNAS 100, Supp. 1, 11917-11923 (2003).
Brossay, L. et al. CD1d-mediated recognition of an α-galactosylceramide by natural killer T cells is hightly conserved through mammalian evolution. J. Exp. Med. 188,(8): 1521-1528 (1998).
Van der Vliet, H., et al. Potent expansion of human natural killer T cells using α-galactosylceramide (KPN7000)-loaded monocyte-derived dendritic cells, cultured in the presence of IL-7 and IL-15. J. Immunol. Methods 247, 61-72 (2001).
Taichman R.,et al. The Hematopoietic Microenvironment: Osteoblasts and the Hematopoietic Microenvironment. Hematol. 4(5):421-426 (2000).
Rattner A, et al. A family of secreted proteins contains homology to the cysteine-rich ligand-binding domain of frizzled receptors. PNAS. 94(7):2859-63. (1997).
Yamane T., et al. Wnt Signaling Regulates Hemopoiesis through Stromal Cells. J. Immunology. 167:765-772. (2001).
Johnson et al., Journal of Bone and Mineral Research, Nov. 2004, vol. 19, No. 11:1749-1757.
Gallager, 1990, Metabolism, vol. 39, issue 4, supplement 1, Apr. 1990, pp. 27-29, abstract only.
DTP Datawarehouse Index Results, from http://dtp.nci.nih.gov/dtpstandard/servlet/dwindex?searchtype=NSC&outputformat=html&searchlist=366218 accessed Dec. 3, 2007.
In Vivo Models, http://dtp/nci.nih.gov/docs/invivo/invivomodels.html, accessed Dec. 3, 2007, p. 33 only of 55 provided.
NCI Communication re InVivo screening: email From: Daniel Zaharevitz[zaharevitz@dtpax2.ncicrf.gov], Sent: Tuesday, Dec. 4, 2007 5:37 PM, To: Garnett, Daniel C., Subject: Re: In vivo screen data, p. 1 of 1.
NCI In Vivo Screening Data http://dtp.nci.nih.gov/dtpstandard/servlet/InvivoScreen?testshortname=tumor+PS . . . Accessed Dec. 3, 2007.
NSC668036-Substance Summary, http://pubchem.ncbi.nlm.nih.gov/summary/summary.cgi?sid=512577&loc=ec_rcs; viewed Oct. 30, 2008.
Reya and Clevers, Nature 2005;434:843-850.
Suzuki et al., Nature Genetics 2004;36:417-422.
Itahana et al., Mol Cell. Nov. 2003;12(5):1251-1260.
Barker and Clevers, Nature Reviews: Drug Discovery 2006;5:997-1014.
U.S. Appl. No. 11/598,916, filed Nov. 14, 2006, Wu et al.
U.S. Appl. No. 09/356,294, filed Jul. 16, 1999, Rabbani et al.
U.S. Appl. No. 08/574,443, filed Dec. 15, 1995, Rabbani et al.
U.S. Appl. No. 11/097,518, filed Apr. 1, 2005, Zheng et al.
U.S. Appl. No. 10/849,643, filed May 19, 2004, Wu et al.
U.S. Appl. No. 10/849,067, filed May 19, 2004, Wu et al.
U.S. Appl. No. 11/084,668, filed Mar. 18, 2005, Wu et al.
U.S. Appl. No. 60/963,771, filed Aug. 6, 2007, Alexanian et al.
U.S. Appl. No. 60/965,279, filed Aug. 17, 2007, Wu et al.

* cited by examiner

COMPOSITIONS AND METHODS FOR BONE FORMATION AND REMODELING

REFERENCE TO RELATED PATENT APPLICATIONS

This application is a continuation-in-part of application Ser. No. 11/097,518, filed Apr. 1, 2005, which is a continuation-in-part of application Ser. No. 11/084,668, filed Mar. 18, 2005, which is continuation-in-part of application Ser. No. 10/849,067, filed May 19, 2004, which claims the benefit of provisional Application No. 60/504,860, filed Sep. 22, 2003, the contents of all of which are incorporated herein by reference.

FIELD OF THE INVENTION

The present invention relates to the field of therapeutic methods, compositions and uses thereof, in the treatment of bone fractures, bone disease, bone injury, bone abnormality, tumors, growths or viral infections as well as for modulating pathophysiological processes including but not limited to glucose metabolism, lipid metabolism, triglyceride metabolism, adipogenesis, tumorigenesis, neurogenesis and bone-related activity. More particularly, the methods and compositions of the invention are directed to the stimulation, enhancement and inhibition of bone formation or bone remodeling.

BACKGROUND OF THE INVENTION

Osteoporosis is a major public health problem, and it is especially prevalent in aging populations (1, 15, 21). The majority of fractures that occur in people over the age of 65 are due to osteoporosis (15, 40). Peak bone mass is a determining factor in establishing the risk of osteoporotic fracture (Heaney et al., 2000), and studies indicate that genetic factors contribute significantly to the variance in peak bone mass. One of the genes that regulate bone mass has recently been identified via positional cloning. Loss of function mutations in low density lipoprotein receptor-related protein 5 (LRP5), a co-receptor for the canonical Wnt signaling pathway (27), were found to be associated with Osteoporosis-Pseudoglioma Syndrome (OPPG), an autosomal recessive disorder which shows a reduction of bone density in humans (9). In addition, two independent kindreds that manifest familial High Bone Mass (HBM) phenotypes were found to harbor a Gly171 to Val substitution mutation (G171V) in LRP5 (5, 22). More recently, additional HBM mutations were reported in the same structural domain of the G171V mutation (36). Moreover, mice in which the LRP5 genes were inactivated by gene targeting showed phenotypes similar to those of OPPG patients (16), and transgenic expression of LRP5G171V in mice resulted in HBM (2). Furthermore, mouse primary osteoblasts showed reduced responsiveness to Wnt in the absence of LRP5 (16), and Wnt (9) or activated beta-catenin (4) stimulated the canonical Wnt signaling activity and induced the production of the osteoblast marker alkaline phosphatase (AP) in osteoblast-like cells. Together, these pieces of evidence indicate that the canonical Wnt signaling pathway plays an important role in the regulation of bone development.

Wnt

The Wnt family of secretory glycoproteins is one of the major families of developmentally important signaling molecules and has been shown to regulate a wide range of biological and pathophysiological processes that include glucose metabolism, bone remodeling, adipogenesis, neurogenesis, stem cell biology, and tumorigenesis. The canonical Wnt signaling pathway is initiated by the binding of canonical Wnts to their receptor complexes consisting of LDL receptor-related protein (LRP) 5/6 and frizzled (Fz) proteins. Through yet to be fully characterized mechanisms, beta-catenin, which is degraded via ubiquitin-mediated proteolysis in the absence of Wnts, is stabilized, leading to an increase in the cytosolic level of β-catenin. Free beta-catenin enters the nucleus and activates gene transcription in a complex with the TCF/LEF-1 transcription factors (61-66). In addition, the Wnt pathway is negatively regulated by many naturally occurring antagonists including the Dickkopf (Dkk) family of polypeptides (67, 68). Dkk binds to LRP5/6 and presumably leads to the inactivation of the receptor proteins (34). Both human and mouse genetic evidence indicates that the Wnt coreceptor LRP5 has an important role in the regulation of bone remodeling; hypomorphic or null alleles lead to early onset of osteoporosis (14), whereas different mutant alleles are associated with high bone mass phenotypes (32, 5, 51). It has been previously shown that that the mutation indirectly reduced Dkk-mediated antagonism of canonical Wnt signaling (69), thus suggesting the Dkk-LRP5 interaction as a potential therapeutic target for increasing bone mass.

Until recently, the canonical Wnt signaling pathway was believed to start when Wnt bound to frizzled Fz proteins. The seven transmembrane domain-containing Fz proteins suppress the Glycogen synthase kinase 3 (GSK3)-dependent phosphorylation of beta-catenin through ill-defined mechanisms involving Dishevelled proteins. This suppression leads to the stabilization of beta-catenin. Beta-catenin can then interact with transcription regulators, including lymphoid enhancing factor-1 (LEF-1) and T cell factors (TCF), to activate gene transcription (7, 10, 38). Recently, genetic and biochemical studies have provided solid evidence to indicate that co-receptors are required for canonical Wnt signaling in addition to Fz proteins (27, 28). The fly ortholog of LRP5/6 (LRP5 or LRP6), Arrow, was found to be required for the signaling of Wg, the fly ortholog of Wnt-1 (37). LRP5 and LRP6 are close homologues which basically function the same way, yet exhibit, different expression patterns. In addition, LRP6 was found to bind to Wnt1 and regulate Wnt-induced developmental processes in *Xenopus* embryos (34). Moreover, mice lacking LRP6 exhibited developmental defects that are similar to those caused by deficiencies in various Wnt proteins (30). Furthermore, LRP5, LRP6 and Arrow were found to be involved in transducing the canonical Wnt signals by binding Axin and leading to Axin degradation and beta-catenin stabilization (25, 35). The LRP5/6-mediated signaling process does not appear to depend on Dishevelled proteins (18, 31). Recently, a chaperon protein, Mesd, was identified as required for LRP5/6 transport to the cell surface (6, 11).

The involvement of the Wnt pathway in inducing repression or expansion of bone growth was demonstrated in a number of publications that described the various effects of mutations in LRP5 upon skeletal structures that served to give rise to low bone mass (14, 88) or increased bone mass (32, 5, 51). There is even a recently described genetically modified mouse model for osteoporosis, where disruption in both chromosomal copies of LRP5 (a LRP5-/- knockout) generates a low bone mass phenotype (89). However, it should be noted that even though the above mentioned references are in regard to LRP5, it should be obvious that intervention in other points along the Wnt signaling pathway could also benefit from administration of compound that have been identified through the processes of the present invention. For recent reviews of the interconnections between the Wnt pathway and bone growth, (see cited references 82, 90, and 91).

Dkk Proteins

*Xenopus* Dickkopf (Dkk)-1 was initially discovered as a Wnt antagonist that plays an important role in head formation (8). Thus far, four members of Dkk have been identified in mammals (17, 26). These include Dkk1, Dkk2, Dkk3 and Dkk4. Dkk1 and Dkk2 inhibit canonical Wnt signaling by simultaneously binding to LRP5 or LRP6 and a single transmembrane protein Kremen (3, 23, 24, 32). It has been previously reported that the LRP5 HBM G171V mutation appeared to attenuate Dkk1-mediated antagonism to the canonical Wnt signaling (5). The present invention describes the mechanism for this attenuation.

The third YWTD repeat domain of LRP5 which is required for Dkk-mediated antagonism of Wnt signaling has previously been identified (69). In addition, the Dkk-binding cavity and key residues within the cavity has been delineated by site-directed mutagenesis (69). This cavity is located at the large opening of the barrel-like structure of the YWTD repeat domain that is made of six beta-propellers (FIG. 17A). Importantly, the two most important residues in the interaction with Dkk, Residues Glu721 and Trp780 (69), are located at the bottom of this cavity, suggesting that small molecule chemicals that bind to this cavity may be able to disrupt the Dkk-LRP5 interaction by blocking the access to this key residue.

SUMMARY OF THE INVENTION

As described herein, the invention provides a model which explains the functional interactions of cavities on domains of receptors or co-receptors involved in bone formation or bone remodeling with Dkk, Wnt, Mesd, or other proteins which function in similar ways. These receptors include, but are not limited to, the LRP5 receptor, the LRP6 receptor, and the frizzled receptor. The LRP5 and LRP6 receptor contains four YWTD repeat domains. Each domain contains multiple YWTD repeats of amino acids. The LRP5 and LRP6 receptor also have an LDL receptor repeat. Both LRP5 and LRP6 are close homologues and function in basically the same way although they possess different expression patterns.

The invention provides methods for identifying non-native or exogenous compounds which bind to or interact with these cavities to cause the stimulation, inhibition or regulation of Wnt signaling, and thus bone formation, tumorigenesis and any other biological and pathological process regulated by Wnt signaling. In particular, the invention is directed to disheveled, beta-catenin or LEF-1/TCF protein or receptor. In a particular embodiment, the invention is directed to a method for identifying a compound that interferes with the binding of protein to LRP5, LRP6, Wnt, Dkk, frizzled, disheveled, beta-catenin or LEF-1/TCF protein or receptor. In one embodiment, the method comprises:

(a) identifying a compound that binds to LRP5, LRP6, Wnt, Dkk, frizzled, disheveled, beta-catenin or LEF-1/TCF protein; and
(b) determining if the compound identified in (a) modulates the binding of a protein to LRP5, LRP6, Wnt, Dkk, frizzled, disheveled, beta-catenin or LEF-1/TCF protein or receptor.

The compounds in step (a) may be identified by:
(a) screening for a compound that fits into the cavity or binding site of LRP5, LRP6, Wnt, Dkk, frizzled, disheveled, beta-catenin, or LEF-1/TCF using the UNITY program;
(b) docking said compound into the cavity using the Flexx program; and
(c) identifying the compound with the highest binding affinity using the Cscore program.

In another embodiment, the method comprises:
(a) identifying a compound that modulates Wnt signaling; and
(b) determining whether the compounds identified in (a) interact or bind to LRP5, LRP6, Wnt, Dkk, frizzled, disheveled, beta-catenin or LEF-1/TCF protein or receptor.

The compound identified may be a small molecule, protein peptide, polypeptide, cyclic molecule, heterocyclic organic molecule, nucleic acid, lipid, charged lipid, polar lipid, non-polar lipid, sugar, glycoprotein, glycolipid, lipoprotein, chemical, or a fragment of a compound that comprises a heterocyclic, organic molecule, nucleic acid, lipid, charged lipid, polar lipid, non-polar lipid, sugar, glycoprotein, glycolipid, lipoprotein, or chemical.

A non-native compound identified using the method of the present invention comprises a compound that is not naturally or normally found in a cell or organism, as opposed to a native compound which is not introduced from an outside source. As will be described in further detail below, the compounds may be identified from a National Cancer Institute (NCI) database through various screening methods and assays. These compounds could also be modified to create derivates or analogues not found in the NCI database or in nature which also function effectively. Compounds are identified which disrupted Dkk and LRP5/6 interactions, Wnt and LRP5/6 interactions and Mesd and LRP5/6 interactions.

In a particular embodiment, the invention is directed to methods of and/or compositions for modulating a pathophysiological process which includes but is not limited to glucose metabolism, cholesterol metabolism, adipogenesis, tumorigenesis, neurogenesis and/or bone-related activity, as well as methods of or compositions for treating a bone fracture, bone disease, bone injury or bone abnormality, diabetes, hyperglycemia or any metabolic disease using the compounds identified using the screening methods of the present invention. In particular embodiments, the compound may have the structure (I):

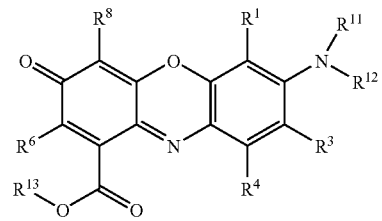

wherein at least one of $R^1$, $R^3$, $R^4$, $R^6$, $R^8$, $R^{11}$, $R^{12}$ or $R^{13}$ is a hydrogen atom and wherein at least one of $R^1$, $R^3$, $R^4$, $R^6$, $R^8$, $R^{11}$, $R^{12}$ or $R^{13}$ comprises an atom other than a hydrogen atom;

the structure (II):

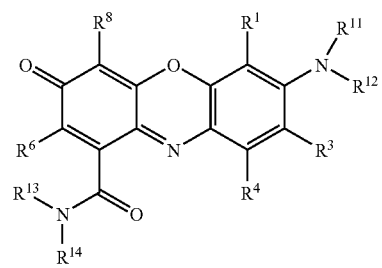

wherein at least one of $R^1$, $R^3$, $R^4$, $R^6$, $R^8$, $R^{11}$, $R^{12}$, $R^{13}$ or $R^{14}$ is a hydrogen atom and wherein at least one of $R^1$, $R^3$, $R^4$, $R^6$, $R^8$, $R^{11}$, $R^{12}$, $R^{13}$ or $R^{14}$ comprises an atom other than a hydrogen atom;
the structure (III):

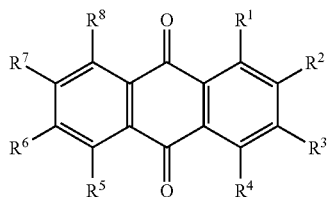

wherein at least one of $R^1$, $R^2$, $R^3$, $R^4$, $R^5$, $R^6$, $R^7$ or $R^8$ is a hydrogen atom and wherein at least one of $R^1$, $R^2$, $R^3$, $R^4$, $R^5$, $R^6$, $R^7$ or $R^8$ comprises an atom other than a hydrogen atom;
the structure (IV):

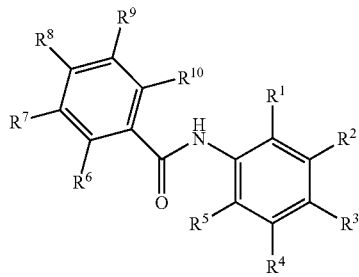

wherein at least one of $R^1$, $R^2$, $R^3$, $R^4$, $R^5$, $R^6$, $R^7$, $R^8$, $R^9$, $R^{10}$ is a hydrogen atom and wherein at least one of $R^1$, $R^2$, $R^3$, $R^4$, $R^5$, $R^6$, $R^7$ or $R^8$, $R^9$ or $R^{10}$ comprises an atom other than a hydrogen atom; or
the structure (V):

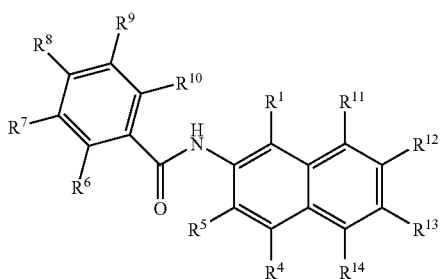

wherein at least one of $R^1$, $R^4$, $R^5$, $R^6$, $R^7$, $R^8$, $R^9$, $R^{10}$, $R^{11}$, $R^{12}$, $R^{13}$ or $R^{14}$ is a hydrogen atom and wherein at least one of $R^1$, $R^4$, $R^5$, $R^6$, $R^7$, $R^8$, $R^9$, $R^{10}$, $R^{11}$, $R^{12}$, $R^{13}$ or $R^{14}$ comprises an atom other than a hydrogen atom.

These compounds are administered in the methods of the present invention or are present in the compositions of the present invention in amounts effective to modulate said pathophysiological processes or to treat said bone fracture, bone disease, bone injury or bone abnormality, diabetes or hyperglycemia to a subject in need thereof. In one embodiment, the subject is a mammalian subject; in a particular embodiment, the subject is a human subject.

In a specific embodiment, the invention is directed to isolated compounds having the following structures:

structure (VI):

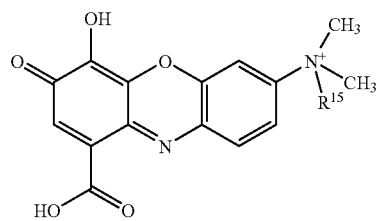

wherein $R^{15}$ is a linear or branched alkyl group;
structure (VII):

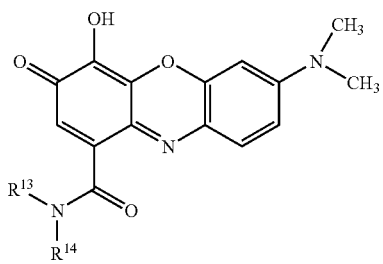

wherein $R^{13}$ and $R^{14}$ are each independently H, or a linear or branched alkyl group; or
structure (VIII):

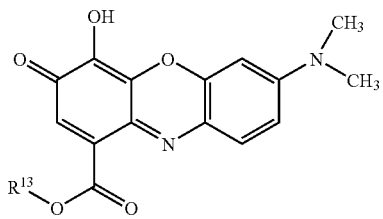

wherein $R^{13}$ is a linear or branched alkyl group or substituted or unsubstituted cycloalkyl group.

The invention is further directed to methods for obtaining compounds (VI)-(VIII). In a particular embodiment, compound (VI) is obtained by reacting gallocyanine with an alkyl halide under conditions promoting formation of said compound. Compound (VII) may be obtained by (a) reacting gallocyanine with an agent to replace the COOH group with a leaving group to obtain an intermediate; and (b) reacting the compound obtained in step (a) with an alkyl amine to obtain said compound.

BRIEF DESCRIPTION OF THE DRAWINGS

FIG. 4B shows equal amounts of Wt and mutant LRP5 expression after transfection.

FIG. 7 shows that amino acid residues in the third YWTD repeat domain, consisting of interaction surfaces, are required for Dkk-mediated inhibition of Wnt.

FIG. 11 shows that at certain concentrations, NCI366218 (FIG. 11A) and NCI8642 (FIG. 11B) can significantly reverse Dkk-mediated inhibition of Wnt activity.

FIG. 12 shows that NCI366218 (FIG. 12A) and NCI8642 (FIG. 12B) inhibit Dkk1 binding to LRP5 wt, and Dkk protein binding to LRP5R34.

FIG. 13 shows that the osteoblast differentiation marker, 2.3Col-GFP, was turned on when BMS culture was treated with IIC8.

FIG. 15 illustrates that both LRP5R12 and LRP5R34 contain Dkk1 binding sites, E721 in R34 is required for the Dkk1 binding and the G171V LRP5 mutant can abolish the Dkk binding to the cell surface.

FIG. 17 shows structures of Dkk-binding cavity and chemicals.

In FIGS. 18 A and B, cells were transfected with Wnt activity reporter gene. Varying concentrations of compounds were added with Wnt3a CM, Wnt3a+Dkk1 CM, or control CM (Basal). Six hours later, Wnt reporter gene activity was determined. (AU: arbitrary unit). The errors are less than 5%. (C, D) Cells were transfected with wildtype LRP5 (C) or LRP5R34 (D). The binding of Dkk-1-AP to the cells was determined. The data with the binding of Dkk-1-AP to cells expressing LacZ being subtracted are presented.

FIG. 19 shows Wnt antagonistic compounds and molecular modeling.

FIG. 20 shows the effects of IIIC3 on bone formation.

DETAILED DESCRIPTION OF THE INVENTION

Figure 1:
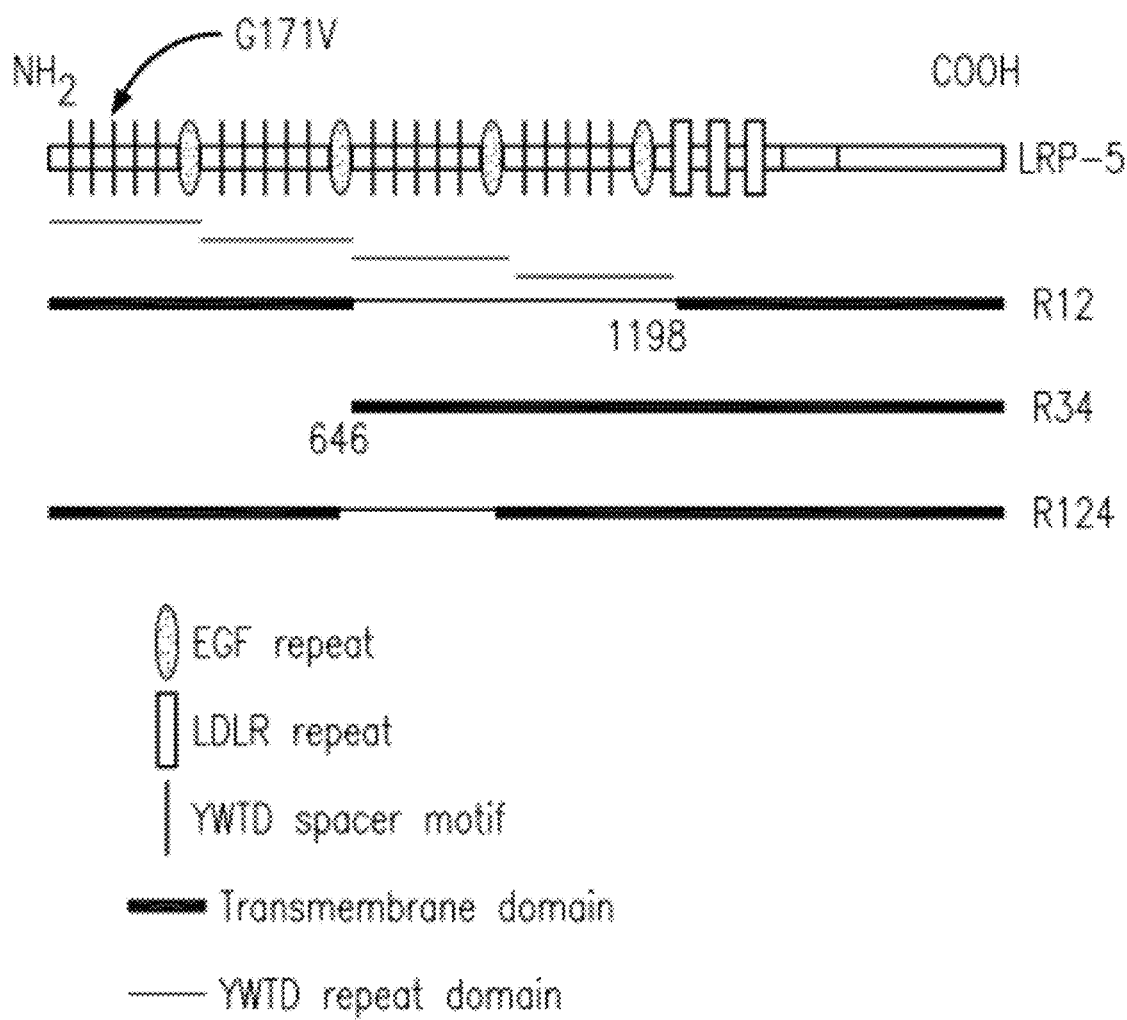
FIG. 1 shows a schematic representation of wild-type LRP5 and its deletion mutants.

The terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. That the upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

The present invention has identified compounds which, when provided to a cell, bind to, interact with or fit into sites or cavities found on the domains of the co-receptors involved in the stimulation, enhancement, inhibition or regulation of bone formation, or bone remodeling. These receptors include the LRP5 receptor, the LRP6 receptor, the frizzled receptor or any other receptor involved in the LRP5 or LRP6 (LRP5/6) receptor system: LRP5 and LRP6 are commonly referred to as LRP5/6 in the literature due to a number of shared features with regard to how they are involved in the canonical Wnt system: LRP5 and LRP6 share a 70% homology on the amino acid level. Due to this similarity, it is expected that many of the compounds that were selected for an ability to bind to LRP5 should also be able to interact with the LRP6 receptor as well. The frizzled receptor is a co-receptor that has a domain containing CRD, a Wnt-binding site which functions to increase or decrease Wnt activity.

The LRP5 and LRP6 receptors contain YWTD repeat domains. In general, the areas comprising the YWTD repeat domains of the LRP5 or LRP6 receptor share sufficient amino acid homology with each other that similar structures are formed by each of these domains, but they are dissimilar enough that they vary in some of the dimensions of the pockets formed and have differences in some of the amino acids that are likely to be important in protein/protein interactions. In a particular embodiment, compounds used in the methods and/or compositions of the present invention interact with or bind to the $3^{rd}$ YWTD domain of the LRP5 and/or LRP6 receptor. Such compounds may or not be able to bind to other YWTD domains. In a particular embodiment, the compounds may bind to the $1^{st}$ or $2^{nd}$ YWTD domain of the LRP5 and/or LRP6 receptor.

Some of these compounds may disrupt the Dkk and LRP5 interaction. Other compounds inhibit Wnt signaling by inhibiting the binding of Wnt to LRP5/6. As will be described herein below, the invention has also identified compounds that modulate interactions between Dkk and kremin, LEF/TCF-1 and beta-catenin, Wnt and frizzled. The compounds of the present invention are non-native or exogenous compounds which are not present in the cell, but originate from an outside source. They comprise agonists, which are agents that can combine with the receptors to initiate events, antagonists, which are agents that combine with the receptors to inhibit the effect of agonists, and partial agonists, which have characteristics of both agonists and antagonists—at times appearing to cause actions and at other times inhibiting actions by decreasing the effects of agonists, for example. Some of these compounds may also increase affinities, or the degree to which drugs or compounds are attracted to receptor binding sites.

Identification of Candidate Compounds

The compounds used in the compositions and methods of the present invention are identified using screening methods described herein.

Screening Compounds that Interact with the Specified Domains of LRP5

Screening Compounds Using Domain III of LRP5 as a Template

Virtual Screening

In a specific embodiment, the UNITY™ program (Tripos, Inc.) may be used to screen the National Cancer Institute (NCI) database (http://129.43.27.140/ncidb2) for chemical compounds that are able to fit into the cavity on Domain III of the YWTD repeat domain of the LRP5 receptor. This database is freely searchable and includes the coordinates of 250, 251 small chemical compounds. A search query is designed to consist of R764 and E721 with 0.3 Å tolerance, and a hydrophobic center with 1.0 Å tolerance that is 3.2 Å away from Trp781, pointing towards the cavity. Taking the flexibility of the compounds into consideration, the Directed Tweak algorithm in the UNITY™ program allows for a rapid, conformationally flexible three dimensional search (21).

The candidate compounds obtained using the UNITY™ program are then docked into the Dkk1 binding surface using the FlexX™ program (Tripos, Inc.) for energy minimization (17), which quickly and flexibly docks ligands to protein-binding sites (44). Residues E721, W864, Y719, R764, D877, F888, G782, W781 and M891, shown to be critical for Dkk1 recognition (FIG. 7A), are considered in the calculations. Following the docking procedures, the compounds are then ranked based on their predicted ability to bind to the Dkk1 binding pocket using the Cscore™ program. Cscore™ generates a relative consensus score based on how well the individual scoring functions of the protein-ligand complexes performed (8). The Cscore™ is then subjected to final manual visual inspection.

Biological Assays

Dkk-1 Binding Assay

The compounds identified may be screened for their ability to affect binding of Dkk-1 to LRP-5 by methods known in the art, e.g., by Dkk-APP assay (see Examples and (69)).

Wnt Activity

The compounds identified may also be screened for Wnt activity. The second and third domains of LRP5 are required for Wnt signaling, and these domains probably directly interact with Wnt molecules. Since these domains share extensive amino acid sequence homology, it is probable that certain compounds that bind to the third domain may also bind to the first two domains, potentially causing the inhibition of Wnt activity. The compounds may be examined for the following: 1) basal reporter activity inhibition; 2) Wnt activity inhibition; and 3) reversal of Dkk-mediated inhibition of Wnt activity.

Osteogenic Assays

Compounds identified may be tested using in vitro or in vivo osteogenic assays.

(a) In Vitro Assays

Wnt stimulates the proliferation and differentiation of cultured osteoblasts and Dkk inhibits this process. Therefore, these compounds increase osteogenesis. This may be monitored by the examination of mineralization or the expression of osteogeneic markers, including the expression of BSP, osteocalcin, and collagen.

(b) In Vivo Assays

Testing for the effectiveness of these compounds in vivo may be conducted to determine if the compounds increase osteogenesis in vivo. A variety of compound doses may be injected at the outer surfaces of calvarias and into bone marrow cavities. Increased bone formation may be examined histologically and through the use of pQCT, DNX, and X-ray radioautography.

Beta-Catenin Level Assay

Cytosolic B-catenin is stabilized by Wnt signaling. The effect of these compounds on Wnt signaling may be examined by the resulting levels of β-catenin.

Phosphorylation of PPPSP Sites of LRP5/6

It was recently discovered that Wnt stimulates the phosphorylation of LRP5 at PPPSP motifs at the intracellular domain of LRP5 (49). Antibodies specific to phosphorylated PSPPP may be obtained and used to examine Wnt activity as described in the examples and as known in the art (49).

Screening Compounds Using Domain II of LRP5 as a Template

Virtual Screening

The structure of this domain may be deduced using homology modeling, as described above. As described in the Examples, site-directed mutagenesis is used to map the residues that are required for Wnt signaling. Virtual screening methods are applied to this Wnt signaling surface using the methods described above. Since domain II is involved in Wnt signaling, compounds identified using domain II as a template may increase Wnt signaling or decrease Wnt signaling. Since domain II and domain III are homologous, the compounds identified using virtual screening may: 1) increase Dkk binding; 2) decrease Dkk binding; 3) increase Dkk antagonism; and/or 4) decrease Dkk antagonism.

Biological Assays

Compounds are tested using biological assays described above. Compounds that increase or decrease Wnt activity are identified using methods described above. Compounds that enhance or inhibit Dkk1 binding are determined using assays described above. Compounds that enhance or inhibit Dkk1 antagonism are determined using assays described above.

Screening Compounds by Using Domain I of LRP5 as a Template

Virtual Screening

The structure of this domain may be deduced using homology modeling, as described above. Site-directed mutagenesis is used to map the residues that are required for Mesd binding and function, as described in FIG. 2. Virtual screening methods are applied to this Mesd-binding surface using the methods described in Example 5.1(A). Since domain I is involved in Mesd functions, compounds identified using domain I as a template may increase or decrease LRP5 presentation to the cell surface, thereby increasing or decreasing Wnt signaling and/or increasing or decreasing Dkk antagonism. Since domain I and domain II are homologous, the compound identified using virtual screening may increase or decrease Wnt signaling. Since domain I and domain III are homologous, the compounds identified using virtual screening may: 1) increase Dkk binding; 2) decrease Dkk binding; 3) increase Dkk antagonism; and/or 4) decrease Dkk antagonism.

Biological Assays

Compounds that increase or decrease Wnt activity are identified using methods described above. Compounds that enhance or inhibit Dkk1 binding and antagonism may be determined in a particular embodiment using assays described in Example 5.1. Compounds that affect Mesd function are determined using assays shown in FIG. 2.

Screening Compounds that Interact with Other Regions of LRP5

The three domains of the extracellular portion of LRP described herein above are not the only potential sites that are candidates for virtual screening. For instance, the EGF repeats that are also in the extracellular portion of LRP 5 are likely to be binding sites for protein/protein interactions and could be used with the methods of the present invention. Furthermore, the intracellular portion of LRP5 is known to have sites that are involved in protein interactions that are also potential target sites.

Screening of Compounds that Interact with the CRD of the Frizzled Receptor

Wnt signals through a transmembrane receptor of the frizzled family. This frizzled receptor passes through the cell membrane several times. A conserved cysteine-rich domain (CRD) located on the N-terminal extracellular region of frizzled acts as a Wnt binding site. Secreted frizzled-related protein Frzb-1 contains CRD and serves as an antagonist of Wnt signaling expression.

The crystal structures of the CRDs of Frizzled 8 and secreted Frizzled-related protein 3 from mice have been determined (12). The Wnt binding sites may be determined by Wnt-binding and mutagenesis assays.

Virtual Screening

Virtual screening methods described above are used to screen for potential compounds that interact with CRD to regulate the Wnt signaling pathway. A homology model is created using the known CRD structure from mouse protein as a template. Homology models for other frizzled family members or for human frizzled protein CRD regions are created. Based on the structure and the amino acids involved in the CRD-Wnt interaction, energy minimization methods were used to screen for compounds to further test the biological activity of each compound. For those that showed higher biological activity, a similar structural query was used to identify additional candidate compounds.

Biological Assays

Wnt-binding assays may be used to screen the effect of compounds on the CRD region of frizzled proteins. CRD peptides (or frizzled proteins) expressed on the surface of the cell with a detectable marker (e.g, Myc-tag). Medium containing the compound and Wnt-alkaline phosphatase fusion protein (e.g Wnt8-AP) was used. After incubation, binding was determined using immuno-histochemistry staining.

Once the candidate compounds show an effect on Wnt binding, other biological assays (as described above are applied to determine each compounds effect on Wnt signaling. (27, 38, 12)

Screening of Compounds that Interact with LRP6

LRP5 and LRP6 are commonly referred to as LRP5/6 in the literature due to a number of shared features with regard to how they are involved in the canonical Wnt system. Therefore, many of the compounds selected for the ability to bind to LRP5 should also be able to interact with LRP6 as well. However, LRP5 and LRP6 just share 70% homology on the amino acid level. Therefore the sequence of LRP6 may be used as a template to identify effectors of the Wnt system in a similar manner to the way that LRP5 to obtain compounds used in the method of the present invention. Each of the first, second and third YWTD repeat domains of LRP6 can be used as selective sites for predicting interactions of a virtual library of chemical compounds. In turn, it is expected that many of the compounds selected for binding to LRP6 could also interact with LRP5.

Screening of Compounds that Interact with Dkk

Virtual Screening

The structure of Dkk1 is solved and its interaction surfaces to Kremen and LRP5/6 may be mapped using mutagenesis, as described in the examples herein. Virtual screening is conducted according to the methods described above. Compounds are found to increase or decrease Dkk binding to LRP5 or Kremen, or increase or decrease Dkk-mediated inhibition of Wnt.

Biological Assays

Compounds that increase or decrease Dkk binding to LRP5 are determined as described above. Compounds that increase or decrease Dkk binding to Kremen are determined as described above with the exception that the cells are transfected with Kremen instead of LRP5. Compounds that increase or decrease Dkk antagonism may in a particular embodiment be determined as described in Example 5.1.

Screening of Compounds that Interact with Dishevelled (DSL) Domains

Cytoplasm disheveled (DSL) proteins are activated by the Wnt-frizzled receptor complex. They are essential in both canonical and non-canonical Wnt signaling pathways. DSL proteins are composed of an N-terminal DIX domain, a central PDZ domain, and a C-terminal DEP domain. These three conserved domains each associate with different proteins, thereby each functioning in a different pathway.

The DIX domain exists as a homodyne and forms a predominantly helical structure. This was determined using pulsed-field gradient NMR studies. The DIX domain mediates targeting to acting stress fibers and cytoplasm vesicles in vivo. It thereby may represent a point of divergence in Wnt signaling. The stabilization of β-catenin through canonical Wnt signaling involves membrane targeting of DSL. Lees 58, Ser 59 and Met 60 in mouse Dvl2 are critically involved in the acting interaction. Lees 68 and Glue 69 are important in cytoplasm vesicle localization.

The PDZ domain interacts with several molecules and plays an important role in both the canonical and non-canonical Wnt pathways. The three dimensional *Xenopus* PDZ domain structure has been determined (7). Through the use of chemical-shift perturbation NMR spectroscopy and binding assays, there is a direct interaction between the conserved motif KTXXXW of frizzled and the PDZ domain of mouse Dvl1. This allows the binding region to be determined (57).

The DEP domain of DSL proteins transducers signals to effector proteins downstream of Dvl in the Wnt pathway. The DEP domain of disheveled is required for the upregulation of β-catenin activity and the stimulation of Lef-1 mediated transcription in mammalian cells. The mouse Dvl1 DEP domain's structure has been determined. (Wong, et al) It has been shown that Lys434, Asp445, and Asp 448 play an important role in protein-protein interaction, and that their mutations Wnt-1 induced Lef-1 activation.

Virtual Screening

Since the functional residues and secondary structures of the DIX domain have been determined, a screening of the existing protein domains may provide information for tertiary structural configurations and potential candidates, and a simulation for the same may generate candidate compounds for binding analysis. Candidate compounds affecting binding may be analyzed, and a new group of similar compounds may be assayed biologically.

Since the three dimensional structure for PDZ and DEP is known, a virtual screening method similar to the method described above may be used. This structure may be used as a template to create a homology model for human protein domains or other similar functional protein domains. Based on the structure and the amino acids involved in specified functions, energy minimization methods may be used to screen compounds. The biological activity of each compound may be tested. For those compounds that show high biological activity, a similar structural query may be used to find more candidate compounds, and biological activity will be further assayed.

Biological Assays

Actin-binding inhibition assays for actin binding regions, and Xnr3 or Siamois expression levels may be used for DIX domain vesicle localization. A constructed vector containing tagged DIX may be transfected into a cell, after compound treatment. Immunofluorescence staining may then be used to determine actin-binding inhibition. RT-PCR may be used to detect Xnr3 or Siamois levels for vesicle localization.

An in vitro binding assay may be used for initial screening for the PDZ domain. A peptide (e.g, Drp C terminal region) that binds to the PDZ domain of Dvl may be used. Purified tagged peptide bound to beads may be mixed with the PDZ domain and each compound, and after incubation, antibody may be used to detect the bound compounds. The binding efficiency effect of each compound may be determined.

To screen for compounds that will affect the canonical Wnt pathway, a luciferase assay may be used for the domain. Cells may be transfected with the Dvl domain. Once these cells are incubated with compounds, Wnt/β-catenin activated luciferase activity may be assayed, thereby measuring each compound's effect.

The compounds are then classified based on their structure, and the identified compounds are further screened. Once candidate compounds affecting protein binding are identified, other biological assays described above may be used to determine the effect of each compound on Wnt signaling (57, 6, 58, 55, and 7).

Screening of Compounds that Interact with β-Catenin

β-catenin mediates the transmission of the Wnt signal into the nucleus and thereby activates the target genes. The Wnt signal prevents β-catenin degradation, allowing β-catenin to accumulate and subsequently translocate to the nucleus to form a transcriptional activating complex with members of the Tcf/LEF family of proteins.

The crystal structure of β-catenin, as well as the complex it forms with Axin, Lef, TCF and several other proteins, have been solved. This information may be used for the screening of compounds that regulate canonical Wnt signaling.

β-catenin contains N-terminal armadillo repeats, which are the binding sites for APC, LEF/TCF, E-cadherin and conductin/axin. All the binding sites are located in armadillo repeat units 3-8 of β-catenin. The binding of the factors occupy the groove and thus preclude the simultaneous binding of other competing β-catenin partners.

Virtual Screening

A modified strategy similar to the virtual screening described above may be used for identifying compounds for β-catenin interaction for binding. The homology model of β-catenin from different species may be generated using β-catenin as a template. Based on the structure and the critical amino acids involved in the interactions with LEF/TCF, Axin and APC, energy minimization methods may be used to screen for compounds to create groups of candidate compounds. Since all the aforementioned proteins occupy similar positions on β-catenin, when biological assays are used for the screening of each compound, all four interactions are tested. Based on initial biological activity, the structures of effective compounds are analyzed, and new groups of compounds are tested using similar methods. Additional biological assays may be carried out to identify the most effective compounds.

Biological Assays

Since all the β-catenin partners occupy similar positions, in vitro translation and protein binding assays may be used to determine the effectiveness of each compound. Tagged β-catenin, TCF, APC, LEF or Axin constructs may be transcribed and translated in vitro. Once they are incubated with the compounds, immunoblotting may be used to detect binding.

Once compounds are identified which affect Wnt binding, other biological assays may be used, as described in section 5.1(B), to determine the effect of each compound on Wnt signaling (52, 43, 16, 59, and 11).

Screening of Compounds that Interact with LEF-1/TCF Transcription Factors

Lymphoid enhancer-binding factor (LEF) is a DNA-binding protein that plays an architectural role in the assembly and function of a regulatory nucleoprotein complex. It recognizes specific nucleotide sequences through a high-mobility-group (HMG) domain. The solution structure of the HMG domain of mouse LEF-1, complexed with a 15-base-pair oligonucleotide duplex containing the optimal binding site from the TCR-alpha gene enhancer, has been solved.

Virtual Screening

A strategy similar to the virtual screening described above may be used to screen for potential compounds that interact with HMG-oligonucleotide binding, to thereby affect the activity of gene expression regulation. Based on the structure, proteins containing HMG domains bend the DNA to which they bind. Any compounds that affect DNA bending or binding ability have an effect on the regulation of gene expression. The homology model for the LEF HMG domain for different species may be created using the known structure as a template. Based on the structure and the amino acids involved in HMG-oligo interaction, energy minimization methods may be used to screen for compounds. Compounds which may either force the bending or prohibit the bending are selected. The DNA binding activity is used to screen the compounds. For compounds which show a much higher or much lower biological activity, a similar structural query may be used to identify additional candidate compounds.

Biological Assays

DNA-binding assays may be used to screen the compounds. Oligonucleotides and HMG domains are incubated with the compounds. Gel retardation assays are used to determine the DNA binding. The binding experiment may be modified with uniformly $^{13}C$ labeled NMR to analyze domain bending. Since LEF controlled gene regulation is directly affected, a luciferase assay may also be used for detecting compound effects. Once compounds affecting protein binding are identified, other biological assays may be used to determine the effect of each compound on Wnt signaling (33).

In carrying out the virtual screening of a library it is understood that the library itself can be a physical library (as exemplified by screening of the NCI library) or it can be a virtual library (as exemplified in Example 6 with compounds Enz 1-Enz 72). The library can be made up of any compounds that can interact with the protein target of interest and affect its interaction with another protein. Examples of such compounds can include but not be limited to organic molecules, peptides, and nucleic acids. The peptides can include but not be limited to a library of peptides of random nature, a permutational series of amino acids, fragments of antibodies to the protein of interest and fragments of a protein that interacts with the protein of interest. The nucleic acids can include but not be limited to aptamers and a library of protein binding sequences.

The Use of Structural Comparison to Find More Effective Compounds

Knowledge of the effectiveness of a compound also allows the purposeful design of a family of novel analogues or compounds that have variations in the groups that are appended to a core structure of the initial compound. The novel compounds obtained in a particular embodiment modulate the binding of a protein to LRP5 or LRP6. As defined herein "modulate" means enhancing or preventing the binding and/or stability of binding of a protein to LRP5 or LRP6, preferably a YWTD repeat domain of LRP5 or LRP6. The protein may include but is not limited to a member of the Dkk family, a member of the Wnt family, sclerostin, or a PA receptor (e.g., TEM8 or CMG2).

For instance, NCI 8642 (also referred to as IIIC3), has the structure:

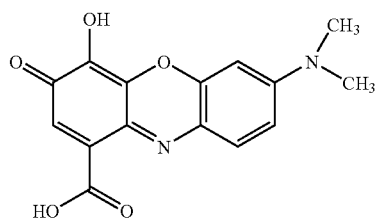 [SMILES: CN(C)c1ccc2nc3c(C(=O)O)cc(=O)c(O)c-3oc2c1]

Retaining the core structure, and indicating where various substitutions can take place, a generalized formula for a family of analogues of this compound can be as follows (I):

wherein at least one of $R^1$, $R^3$, $R^4$, $R^6$, $R^8$, $R^{11}$, $R^{12}$ or $R^{13}$ is a hydrogen atom and wherein at least one of $R^1$, $R^3$, $R^4$, $R^6$, $R^8$, $R^{11}$, $R^{12}$ or $R^{13}$ comprises an atom other than a hydrogen atom. In a particular embodiment, $R^1$, $R^3$, $R^4$, $R^6$, $R^8$, $R^{11}$, $R^{12}$, and $R^{13}$ independently comprise hydrogen, oxygen, hydroxy, a halogen, a linear or branched ($C_1$-$C_{16}$) alkyl group, a substituted linear or branched ($C_1$-$C_{16}$) alkyl group, a cycloalkyl group, a substituted cycloalkyl group, a heterocyclic group, a substituted heterocyclic group, an aryl alkyl group, a substituted aryl alkyl group, a heteroarylalkyl group, a substituted heteroararylalkyl group, an alkoxy group, a substituted alkoxy group, an alkene group, a substituted alkene group, an acyl group, an amine group, an amide group, a nitrate, a nitrate ester, a carboxyl group, a carboxyl ester, a sulfide, a sulfoxide, a sulfonate, a sulfonate ester, a sulfone, a sulfonamide, a phosphate, a phosphate ester, a phosphonate, a phosphonate ester, a phosphamide, a phosphoramide, a thiophosphate, a thiophosphate ester, a thiophosphonate, or a thiophosphonate ester, wherein $R^1$ and $R^{11}$, $R^{11}$ and $R^{12}$, $R^{12}$ and $R^3$, $R^3$ and $R^4$, $R^{13}$ and $R^6$ may independently be fused together to form one or more rings, or any combination of the foregoing. When the nitrogen of the amine group comprising $R^{11}$ and $R^{12}$ is charged and further comprises $R^{15}$, wherein $R^{15}$ is as described previously for $R^1$, $R^3$, $R^4$, $R^6$, $R^8$, $R^{11}$, $R^{12}$ and $R^{13}$. In a particular embodiment, the compound has the structure (VIII):

wherein $R^{13}$ is a linear or branched alkyl group or substituted or unsubstituted cycloalkyl group. In a most particular embodiment $R^{13}$ is a linear or branched $C_{2-4}$ group. In another particular embodiment R13 is a cycloalkyl C3-8 group.

This core compound can be generalized further by retaining the ring structure and allowing substitutions for the carboxyl or ester group shown in the structure above, giving a formula (II) for a series of other analogues as follows:

wherein at least one of $R^1$, $R^3$, $R^4$, $R^6$, $R^8$, $R^{11}$, $R^{12}$, $R^{13}$ or $R^{14}$ is a hydrogen atom and wherein at least one of $R^1$, $R^3$, $R^4$, $R^6$, $R^8$, $R^{11}$, $R^{12}$, $R^{13}$ or $R^{14}$ comprises an atom other than a hydrogen atom In a particular embodiment, $R^1$, $R^3$, $R^4$, $R^6$, $R^8$, $R^{11}$, $R^{12}$, $R^{13}$ and $R^{14}$ independently comprise hydrogen, oxygen, hydroxy, a halogen, a linear or branched ($C_1$-$C_{16}$) alkyl group, a substituted linear or branched ($C_1$-$C_{16}$) alkyl group, a cycloalkyl group, a substituted cycloalkyl group, a heterocyclic group, a substituted heterocyclic group, an aralalkyl group, a substituted arylalkyl group, a heteroarylalkyl group, a substituted heteroarylalkyl group, an alkoxy group, a substituted alkoxy group, an alkene group, a substituted alkene group, an acyl group, an amine group, an amide group, a nitrate, a nitrate ester, a carboxyl group, a carboxyl ester, a sulfide, a sulfoxide, a sulfonate, a sulfonate ester, a sulfone, a sulfonamide, a phosphate, a phosphate ester, a phosphonate, a phosphonate ester, a phosphamide, a phosphoramide, a thiophosphate, a $R^{11}$ and $R^{12}$, $R^{12}$ and $R^3$, $R^3$ and $R^4$, $R^{13}$ and $R^6$ may independently be fused together to form one or more thiophosphate ester, a thiophosphonate, or a thiophosphonate ester, wherein $R^1$ and $R^{11}$, rings, or any combination of the foregoing.

In a particular embodiment the compound has the structure (VII):

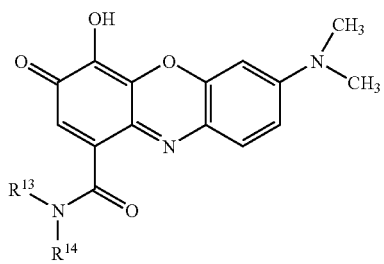

wherein $R^{13}$ and $R^{14}$ are each independently H or a linear or branched alkyl group.

In a more particular embodiment, $R^{13}$ and $R^{14}$ are independently H or a linear or branched $C_{1-5}$ linear or branched alkyl group. In most specific embodiments, $R^{13}$ is H and $R^{14}$ is $CH_3$ groups. (Enz M14); $R^{13}$ and $R^{14}$ are $CH_3$ groups (Enz M15); $R^{13}$ are $CH_3$ groups and wherein $R^{14}$ is $C(CH_3)_3$ (Enz M25); $R^{13}$ is H and $R^{14}$ is $(CH_2)_2CH(CH_3)_2$. (Enz M35); $R^{13}$ is H, wherein $R^{11}$ and $R^{12}$ are $CH_3$ groups and wherein $R^{14}$ is $CH_2CH(CH_3)(CH_2CH_3)$. (Enz M39).

The compound encompassed by (VII) may be obtained by
(a) reacting gallocyanine with an agent to replace the COOH group on gallocyanine with a leaving group;
(b) reacting the compound obtained in step (a) with an alkyl amine to obtain said compound (VII).

The invention is further directed to a novel compound having the structure (VI):

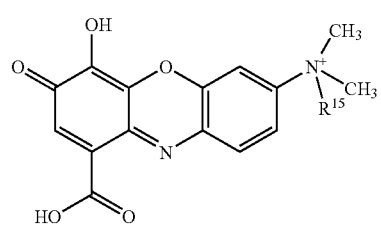

wherein $R^{15}$ is a linear or branched alkyl group. In a particular embodiment, $R^{15}$ is a linear or branched $C_{1-5}$ alkyl group. In most specific embodiments, $R^{15}$ is a methyl group (Enz M01); $R^{15}$ is an ethyl group (EnzM02); $R^{15}$ is a propyl group (EnzM03); $R^{15}$ is $CH_2C(CH_3)_3$ (EnzM12).

This compound may be obtained by reacting gallocyanine with an alkyl halide under conditions promoting formation of said compound.

In a similar fashion, a series of compounds that may be of interest may be designed using IC15 and IC5 as starting points:

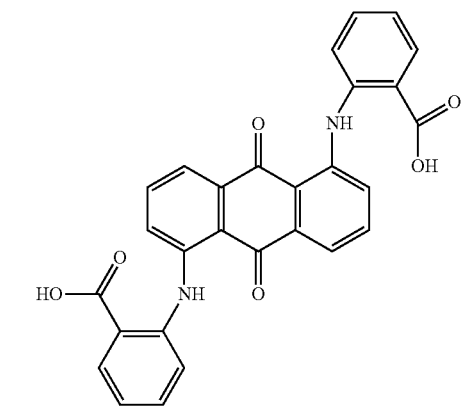

IC 15 and

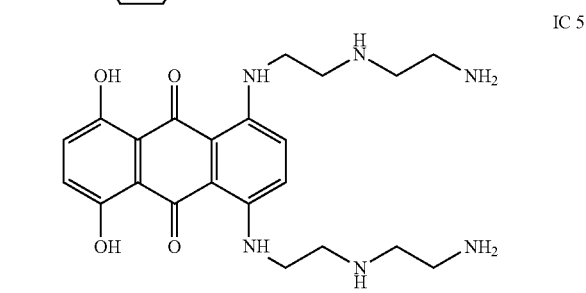

IC 5

As described previously, the common anthra-9,10-quinone structure in these two compounds was used in a secondary screening with UNITY™ followed by docking with FlexX™ and biological assays. This led to the identification of IIC8, IIC10, IIC18 and IIC19 (all sharing the anthra-9,10-quinone) as demonstrating effects upon Wnt activity. Thus, in this instance a family of analogues could have the generalized structure (III):

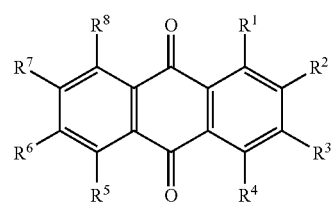

wherein at least one of $R^1$, $R^2$, $R^3$, $R^4$, $R^5$, $R^6$, $R^7$ or $R^8$ is a hydrogen atom and wherein at least one of $R^1$, $R^2$, $R^3$, $R^4$, $R^5$, $R^6$, $R^7$ or $R^8$ comprises an atom other than a hydrogen atom. In a preferred embodiment, $R^1$, $R^2$, $R^3$, $R^4$, $R^6$, $R^6$, $R^7$, $R^8$ independently comprise hydrogen, oxygen, hydroxy, a halogen, a linear or branched ($C_1$-$C_{16}$) alkyl group, a substituted linear or branched ($C_1$-$C_{16}$) alkyl group, a cycloalkyl group, a substituted cycloalkyl group, a heterocyclic group, a substituted heterocyclic group, an aralalkyl group, a substituted aralalkyl group, a heteroarylalkyl group, a substituted heteroaryllalkyl group, an alkoxy group, a substituted alkoxy group, an alkene group, a substituted alkene group, an acyl group, an amine group, an amide group, a nitrate, a nitrate ester, a carboxyl group, a carboxyl ester, a sulfide, a sulfoxide, a sulfonate, a sulfonate ester, a sulfone, a sulfonamide, a phosphate, a phosphate ester, a phosphonate, a phosphonate ester, a phosphamide, a phosphoramide, a thiophosphate, a thiophosphate ester, a thiophosphonate, or a thiophosphonate ester, wherein $R^1$ and $R^2$, $R^2$ and $R^3$, $R^3$ and $R^4$, $R^5$ and $R^6$, $R^6$ and $R^7$, $R^7$ and $R^8$ may independently be fused together to form one or more rings, or any combination of the foregoing.

The invention further provides a family of compounds that could be based upon the secondary screening described above where IIC15 (structure shown below) showed interesting effects upon Wnt regulation.

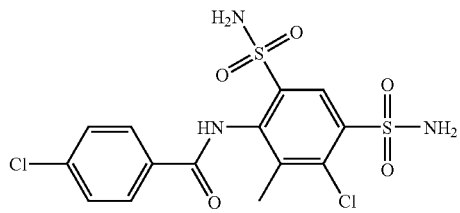

IIC 15

Other compounds that share common structural elements with this compound and which demonstrate effects upon Wnt activity are IIC1, IIC2, IIC7 and IIIC10, the structures of which are shown in Table IV.

Thus, the invention provides for compounds having the structure (IV):

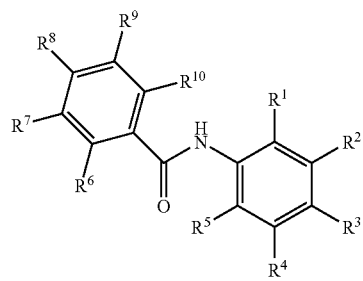

wherein at least one of $R^1$, $R^2$, $R^3$, $R^4$, $R^5$, $R^6$, $R^7$, $R^8$, $R^9$, $R^{10}$ is a hydrogen atom and wherein at least one of $R^1$, $R^2$, $R^3$, $R^4$, $R^5$, $R^6$, $R^7$ or $R^8$ comprises an atom other than a hydrogen atom. In a specific embodiment, $R^1$, $R^2$, $R^3$, $R^4$, $R^5$, $R^6$, $R^7$, $R^8$, $R^9$ or $R^{10}$ independently comprise hydrogen, oxygen, hydroxy, a halogen, a linear or branched ($C_1$-$C_{16}$) alkyl group, a substituted linear or branched ($C_1$-$C_{16}$) alkyl group, a cycloalkyl group, a substituted cycloalkyl group, a heterocyclic group, a substituted heterocyclic group, an arylalkyl group, a substituted arylalkyl group, a heteroarylalkyl group, a substituted heteroarylalkyl group, an alkoxy group, a substituted alkoxy group, an alkene group, a substituted alkene group, an acyl group, an amine group, an amide group, a nitrate, a nitrate ester, a carboxyl group, a carboxyl ester, a sulfide, a sulfoxide, a sulfonate, a sulfonate ester, a sulfone, a sulfonamide, a phosphate, a phosphate ester, a phosphonate, a phosphonate ester, a phosphamide, a phosphoramide, a thiophosphate, a thiophosphate ester, a thiophosphonate, or a thiophosphonate ester, wherein $R^1$ and $R^2$, $R^2$ and $R^3$, $R^4$ and $R^5$, $R^3$ and $R^4$, $R^6$ and $R^7$, $R^7$ and $R^8$, $R^8$ and $R^9$ and $R^9$ and $R^{10}$ may independently be fused together to form one or more rings, or any combination of the foregoing.

It should be noted that the R groups on the aromatic rings of these core structures may be fused together to form more complex ring structures. Thus, for instance, carbon chains of $R^2$ and $R^3$ could be joined together to give a series of compounds having the structure (V):

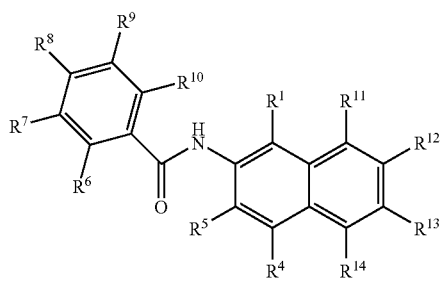

wherein at least one of $R^1$, $R^4$, $R^5$, $R^6$, $R^7$, $R^8$, $R^9$, $R^{10}$ is a hydrogen atom and wherein at least one of $R^1$, $R^4$, $R^5$, $R^6$, $R^7$ or $R^8$, $R^9$, $R^{10}$, $R^{11}$, $R^{12}$, $R^{13}$ comprises an atom other than a hydrogen atom. In a specific embodiment, $R^1$, $R^4$, $R^5$, $R^6$, $R^7$, $R^8$, $R^9$, $R^{10}$, $R^{11}$, $R^{12}$, $R^{13}$ and $R^{14}$ independently comprise hydrogen, oxygen, hydroxy, a halogen, a linear or branched ($C_1$-$C_{16}$) alkyl group, a substituted linear or branched ($C_1$-$C_{16}$) alkyl group, a cycloalkyl group, a substituted cycloalkyl group, a heterocyclic group, a substituted heterocyclic group, an arylalkyl group, a substituted arylalkyl group, a heteroarylalkyl group, a substituted heteroarylalkyl group, an alkoxy group, a substituted alkoxy group, an alkene group, a substituted alkene group, an acyl group, an amine group, an amide group, a nitrate, a nitrate ester, a carboxyl group, a carboxyl ester, a sulfide, a sulfoxide, a sulfonate, a sulfonate ester, a sulfone, a sulfonamide, a phosphate, a phosphate ester, a phosphonate, a phosphonate ester, a phosphamide, a phosphoramide, a thiophosphate, a thiophosphate ester, a thiophosphonate, or a thiophosphonate ester, wherein $R^1$ and $R^{11}$, $R^{11}$ and $R^{12}$, $R^{12}$ and $R^{13}$, $R^{13}$ and $R^{14}$, $R^{14}$ and $R^4$, $R^4$ and $R^5$, $R^6$ and $R^7$, $R^7$ and $R^8$, $R^8$ and $R^9$ and $R^9$ and $R^{10}$ may independently be fused together to form one or more rings, or any combination of the foregoing.

Examples of tested compounds that share this structure are IIC1 and IIC2 mentioned above.

The core compounds disclosed hereinabove can be combined to form compounds that are an amalgam that span various interaction points of the various core compounds described above. For instance, IC13, which was shown to affect Wnt activity, has two of the III moieties linked together and in combination with the linkage between them it also comprises an analogue structure derived from the IV moiety. The structure of this hybrid molecule is shown below:

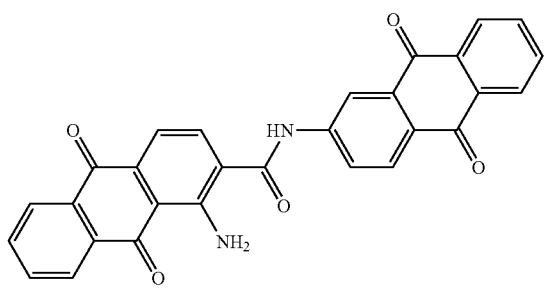 [SMILES: Nc1c(C(=O)Nc2ccc3c(c2)C(=O)c2ccccc2C3=O)ccc2c1C(=O)c1ccccc1C2=O]

Other Protein Surface Targets of the Wnt Signaling Pathway

There are numerous proteins involved in the Wnt signaling pathway that participate in protein/protein interactions which can be affected by the administration of pharmacological compounds. Examples of various proteins that participate in protein/protein interactions in the LRP516 and/or canonical and non-canonical Wnt pathways are described in numerous references (82, 68, 83, 81, 84, 85, 86, and 87). For a given target protein of this group, there can be a variety of different proteins that interact with the target protein. These binding partners may bind to different sites on the target protein or two different binding partners may share the same site or overlapping sites on the target protein. The methods of the present invention can be applied to either participant in each interaction pair and appropriate structures and domains can be identified by any means known to those skilled in the art. These means can include but not be limited to, construction of clones comprising the various portions of target proteins (extracellular and intracellular domains, for example) and testing for binding with various deletion mutants of the interacting protein partner; random mutation of the target protein and measuring effects upon Wnt activity or some other biological marker followed by sequencing of interesting mutants; alanine scanning to identify critical amino acids involved in the function of protein/protein interactions of the selected interacting pair, construction of various deletion mutants of the target protein and measuring their ability to influence Wnt activity or some other biological marker; construction of AP fusion versions of deletion mutants of the target protein; the use of analogous proteins to prepare models of protein structures; the use of peptide libraries to determine peptide sequences that bind to particular targets; X-ray crystallography and NMR analysis. As described above, many of these structure and sites are known in the art and the particular site on a target protein may be chosen for virtual screening and assayed by various means. For other protein/protein interactions, the existence of the interaction is known but the particular site needs further investigation by any of the means described above. Examples of protein targets and their binding site for an interacting protein are given below and include but are not limited to:

| Structural Target | Binding sites for: |
| --- | --- |
| Wnt | LRP5/6, Dkk, Frizzled, sFRPs, Wif-1, Cerebrus |
| LRP5/6 | Wnt, Axin, Boca, mesd, Frat1, Wise, SOST, TEM8/ATR, CMG2 |
| Dkk | Wnt, Kremen |
| Dishevelled | Frizzled, Axin, naked |
| Frizzled | Wnt, Disheveled, Norrin |
| Beta-catenin | APC, LEF/TCF, E-cadherin, Axin |
| LEF/TCF | Beta-catenin |

In protein/protein interactions, there is a site on each constituent that participates in the interaction, and thus either surface can serve as a potential target for virtual screening. There are at least two benefits achieved by this approach. In the first place, the potential pharmacopia of compounds influencing Dkk/LRP reactions is now widened by the inclusion of entirely new families of compounds identified by an affinity for Dkk. Secondly, the binding domains of proteins that are involved in signal generation tend to be multivalent. For instance, the binding domains on LRP5/6 are used by a number of different proteins that vary in their purpose and effect. With regard to the present example, Dkk may bind to the second and third domains of LRP5/6 (79), but it has also recently been shown that sclerostin can bind to the first and second LRP5/6 domains (80) and that one of these domains serves as a binding site for the toxic effects of anthrax (81).

Thus, even when a particular drug is targeted to a single site on the LRP5/6 receptor, there may be a number of different signal generating proteins other than Dkk that may be affected by a drug binding to that site. These effects may also be beneficial or they may be neutral or even deleterious thus affecting the use of a compound for therapeutic use. By the same token, when the corresponding LRP5/6 binding site on Dkk is chosen as a target, there may be a variety of other protein/protein interactions that also use this locus. As such, when a drug is identified that binds to this site, the particular proteins that may be influenced by a drug selected for binding to the LRP/Dkk binding site on Dkk may represent a different group of proteins from those affected by a drug selected for binding to the LRP/Dkk binding site on LRP5/6.

In addition to targeting the other side of the Wnt/Dkk reaction, other protein/protein interactions involved in Wnt signaling have also been described as potential candidates for the foregoing processes. In a similar fashion, they achieve some of the benefits described above. For instance, similar to choosing Dkk instead of LRP5/6 as a target, the use of a different protein target should allow the discovery of an entirely different set of compounds that can affect the Wnt signaling pathway. In this case, it is possible that the same effect may be achieved (influencing Wnt signaling) but a different part of the pathway is affected. It also should be understood that a dual discovery program can be carried out where each partner of a protein/protein interaction is a candidate for drug discovery. Secondly, as described earlier, a compound that influences one particular protein/protein interaction is also likely to affect other protein/protein interactions that were not necessarily the primary target. Thus it may prove that some members of the Wnt signaling pathways may be more specific than others in achieving desirable effects. In addition to the particular protein/protein interactions that were specified earlier, it should be understood that all proteins that participate in protein/protein interactions for Wnt signaling can potentially be candidates for carrying out procedures of the present invention. These protein targets can participate in both canonical and non-canonical signaling pathways or they may be restricted to one pathway or the other.

As noted above, the compounds used in the compositions and methods of the present invention may be used to modulate pathophysiological processes. As defined herein "modulate" includes but is not limited to altering the amount of or rate of a particular process, adjusting a process, or adjusting to or keeping in proper measure or proportion.

The present invention can be applied to numerous systems that are affected by or dependent upon the canonical or non-canonical Wnt signaling pathway. These may be diseases or conditions that are caused by alterations or defects in the Wnt signaling pathway where adjustments in Wnt activity may alleviate these diseases or conditions. Alternatively, there may be disease or conditions that are not caused by problems with Wnt activity per se but curative or therapeutic effects may be achieved by manipulations of Wnt activity. As described previously in U.S. Patent Application Serial No. 20050196349, U.S. Patent Application Serial No. 20050261181 and U.S. Patent Application Serial No. 20060030523, all of which are incorporated herein by reference, examples of applications where manipulations of the Wnt signaling system may provide beneficial effects can include but not be limited to influencing bone formation and remodeling as well as treating tumors and abnormal growths.

As described above, the compounds that have been identified through the present invention may also find application in curative or preventive means in tumors and abnormal growth. Although it would be understood from the previous passage that tumors or abnormal growth of bone cells or bone tissues could be a target for these compounds, Wnt activity is more widespread and a factor in abnormal growth of other cells and tissues as well. It should be pointed out that when the first Wnt gene was isolated, it was considered to be a proto-oncogene (92) and named "int-1" due to its propensity to cause tumors when mouse mammary virus integrated into this site. It was only years later, when the role of this family of genes in embryonic development became clear, that it was renamed "Wnt" (39). Since genes involved in the Wnt pathway are expressed in a wide variety of tissues, there is an equal connection with a large variety of different tumor types associated with changes in Wnt pathway expression. Additionally, there are different effects depending upon the particular type of cancer. For instance, evidence has been shown that Wnt 5A could be a tumor suppressor in hematopoietic cells (93) and on the other hand, Wnt 5A may promote motility and invasiveness in melanomas thereby potentially having a role in metastasis (94). For reviews on the interactions of the Wnt pathway and tumorigenesis or tumor maintenance as well as the numerous types of cancers where these effects are seen (see cited references 95, 96, 97, 66, 98, and 99). It should also be understood that a linkage of effects by Wnt on cancer and control of bone growth is not a phenomenon that is restricted to bone cancers. Multiple myeloma, which is essentially a hematologic cancer, also has indirect effects upon bone growth where increased fragility is one of the hallmarks of the disease. This latter effect has been traced to increased levels of Wnt inhibitors Dkk (100) and sFRP-2 (101) in myeloma cells.

Disease conditions associated with alterations in the Wnt pathway signaling system are not restricted to just tumors or abnormal bone growth. Genetic defects in genes involved in expression of components of the Wnt signaling system exhibit defects in various organs and systems. Even for the same gene, the particular site or even the particular mutation can affect the particular phenotypic expression of the defect. As described earlier, certain mutations in LRP5 lead to increased bone growth and other mutations lead to diminished bone growth. Some genetic diseases are likely related to developmental processes that are affected by a defect in a constituent of the Wnt signaling system. For instance, a mutation in either LRP5 or FZD4 can lead to Familial Exudative Vitreoretinopathy characterized by a lack of vascularization of the retina (102). In a more radical instance, there is a complete failure to generate limbs in a condition called Tetraamelia which is caused by a defect in Wnt3 (103). Other genetic mutations may affect the role of Wnt signaling in homeostatic processes that are post-embryonic in nature. For instance, the defects that led to either increased or decreased bone mass as well as tumorigenic events are ongoing post-birth processes. However, as described above, these are not the only homeostatic processes affected by Wnt signaling. The possibility of a mutation in a Wnt pathway gene affecting diabetes had been previously indicated by results from mice deficient in both copies of LRP5. Although these mice were cited earlier in the context of a potential model for osteoporosis, further studies showed that this strain exhibited other phenotypic characteristics as well including increased serum cholesterol levels and a markedly impaired glucose tolerance response (20). The latter result is not surprising since the LRP5 gene was initially mapped and cloned due to its proximity to the IDDM4 region which has been associated with diabetes (18). In addition, a recent study (104) has shown an increased likelihood of development of Type 2 Diabetes in individuals with an allele in the TCF7L2 gene (formerly referred to as TCF4) with risk factors of 1.45 and 2.41 for heterozygous and homozygous conditions, respectively. Other diseases or conditions that have been found to be associated with various members of the Wnt signaling system include development of polycystic kidney disease (105), renal fibrosis (106), pulmonary fibrosis (107), aggressive fibramotosis (108), and schizophrenia (109). (For reviews on the relationship between Wnt signaling pathways and disease, see cited references 63 and 66).

As such, any disease processes that are either caused by changes in Wnt signaling or show differences in Wnt signaling as a result of the presence of a particular disease or condition may find use with the compounds that are identified through the use of the present invention.

The compounds used in the method of the present invention modulate, and in particular, attenuate the Mesd-LRP5 interaction, resulting in less LRP5 receptors present at the cell surface which may lead to an increase in bone density through bone formation or bone remodeling.

Dkk acts as a Wnt antagonist when it binds to, or interacts with, the third domain of the LRP5 receptor. Compounds have been identified that inhibit the Dkk-LRP5 interaction to promote bone formation or remodeling. As described in the Examples below, one compound, NCI366218 (IIC8) has been found to stimulate osteoblast differentiation in tissue culture models. Wnt and Dkk have been shown to regulate the growth and differentiation of mesenchymal stem cells. Compounds have been identified which function as mesenchymyl stem cell regulators for the regulation of bone formation and for the development and differentiation of hemaetopoietic stem cells.

Wnt has been shown to regulate the growth and differentiation of hematopoietic stem cells. Compounds have been identified which function as hemaetopoietic stem cell regulators for the regulation of bone formation and for the proliferation and expansion of stem cells in vivo and in vitro.

Compositions

The compound(s) used in the method of the present invention may be formulated into a composition, most notably a pharmaceutical composition. Such a composition typically contains from about 0.1 to 90% by weight of a metabolic intermediate of the invention formulated in and/or with a pharmaceutically acceptable carrier or excipient. Pharmaceutical formulation is a well-established art, and is further described in Gennaro (ed.), Remington: The Science and Practice of Pharmacy, 20th ed., Lippincott, Williams & Wilkins (2000); Ansel et al., Pharmaceutical Dosage Forms and Drug Delivery Systems, 7th ed., Lippincott Williams & Wilkins (1999); and Kibbe (ed.), Handbook of Pharmaceutical Excipients American Pharmaceutical Association, 3rd ed. (2000).

Briefly, formulation of the pharmaceutical compositions of the present invention will depend upon the route chosen for administration. The pharmaceutical compositions utilized in this invention can be administered by various routes including both enteral and parenteral routes, including oral, intravenous, intramuscular, subcutaneous, inhalation, intrathecal, intraventricular, transmucosal, transdermal, intranasal, intraperitoneal, and intrapulmonary. The pharmaceutical composition may comprise one or more agents of the present invention.

Oral dosage forms can be formulated as tablets, pills, dragees, capsules, liquids, gels, syrups, slurries, suspensions, and the like, for ingestion by the patient. Solid formulations of the compositions for oral administration can contain suitable carriers or excipients, such as carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, sodium carboxymethylcellulose, or microcrystalline cellulose; gums including arabic and tragacanth; proteins such as gelatin and collagen; inorganics, such as kaolin, calcium carbonate, dicalcium phosphate, sodium chloride; and other agents such as acacia and alginic acid. Agents that facilitate disintegration and/or solubilization can be added, such as the cross-linked polyvinyl pyrrolidone, agar, alginic acid, or a salt thereof, such as sodium alginate, microcrystalline cellulose, corn starch, sodium starch glycolate, and alginic acid. Tablet binders that can be used include acacia, methylcellulose, carboxymethylcellulose, polyvinylpyrrolidone (Povidon™), hydroxypropyl methylcellulose, sucrose, starch and ethylcellulose. Lubricants that can be used include magnesium stearates, stearic acid, silicone fluid, talc, waxes, oils, and colloidal silica. Fillers, agents that facilitate disintegration and/or solubilization, tablet binders and lubricants, including the aforementioned, can be used singly or in combination. Solid oral dosage forms need not be uniform throughout. For example, dragee cores can be used in conjunction with suitable coatings, such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures.

Oral dosage forms of the present invention include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers. Additionally, dyestuffs or pigments can be added to the tablets or dragee coatings for product identification or to characterize the quantity of active compound, i.e., dosage.

Liquid formulations of the pharmaceutical compositions for oral (enteral) administration are prepared in water or other aqueous vehicles and can contain various suspending agents such as methylcellulose, alginates, tragacanth, pectin, kelgin, carrageenan, acacia, polyvinylpyrrolidone, and polyvinyl alcohol. The liquid formulations can also include solutions, emulsions, syrups and elixirs containing, together with the active compound(s), wetting agents, sweeteners, and coloring and flavoring agents.

The pharmaceutical compositions of the present invention can also be formulated for parenteral administration. Formulations for parenteral administration can be in the form of aqueous or non-aqueous isotonic sterile injection solutions or suspensions.

For intravenous injection, water soluble versions of the compounds of the present invention are formulated in, or if provided as a lyophilate, mixed with, a physiologically acceptable fluid vehicle, such as 5% dextrose ("D5"), physiologically buffered saline, 0.9% saline, Hanks' solution, or Ringer's solution. Intravenous formulations may include carriers, excipients or stabilizers including, without limitation, calcium, human serum albumin, citrate, acetate, calcium chloride, carbonate, and other salts.

Intramuscular preparations, e.g. a sterile formulation of a suitable soluble salt form of the compounds of the present invention, can be dissolved and administered in a pharmaceutical excipient such as Water-for-Injection, 0.9% saline, or 5% glucose solution. Alternatively, a suitable insoluble form of the compound can be prepared and administered as a suspension in an aqueous base or a pharmaceutically acceptable oil base, such as an ester of a long chain fatty acid (e.g., ethyl oleate), fatty oils such as sesame oil, triglycerides, or liposomes.

Parenteral formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like).

Aqueous injection suspensions can also contain substances that increase the viscosity of the suspension, such as sodium carboxymethyl cellulose, sorbitol, or dextran. Non-lipid polycationic amino polymers can also be used for delivery. Optionally, the suspension can also contain suitable stabilizers or agents that increase the solubility of the compounds to allow for the preparation of highly concentrated solutions.

Pharmaceutical compositions of the present invention can also be formulated to permit injectable, long-term, deposition. Injectable depot forms may be made by forming microencapsulated matrices of the compound in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in microemulsions that are compatible with body tissues.

Inhalation formulations can also readily be formulated. For inhalation, various powder and liquid formulations can be prepared. For aerosol preparations, a sterile formulation of the compound or salt form of the compound may be used in inhalers, such as metered dose inhalers, and nebulizers. Aerosolized forms may be especially useful for treating respiratory disorders.

Alternatively, the compounds of the present invention can be in powder form for reconstitution in the appropriate pharmaceutically acceptable carrier at the time of delivery.

The pharmaceutically active compound in the pharmaceutical compositions of the present invention can be provided as the salt of a variety of acids, including but not limited to hydrochloric, sulfuric, acetic, lactic, tartaric, malic, and succinic acid. Salts tend to be more soluble in aqueous or other protonic solvents than are the corresponding free base forms.

After pharmaceutical compositions have been prepared, they are packaged in an appropriate container and labeled for treatment of an indicated condition.

The active compound will be present in an amount effective to achieve the intended purpose. The determination of an effective dose is well within the capability of those skilled in the art.

The therapeutically effective dose of the compound(s) used in the present invention can be estimated initially by in vitro tests, such as cell culture assays, followed by assay in model animals, usually mice, rats, rabbits, dogs, or pigs. The animal model can also be used to determine an initial preferred concentration range and route of administration.

For example, the $ED_{50}$ (the dose therapeutically effective in 50% of the population) and $LD_{50}$ (the dose lethal to 50% of the population) can be determined in one or more cell culture or animal model systems. The dose ratio of toxic to therapeutic effects is the therapeutic index, which can be expressed as $LD_{50}/ED_{50}$. Pharmaceutical compositions that exhibit large therapeutic indices are preferred.

The data obtained from cell culture assays and animal studies are used in formulating an initial dosage range for human use, and preferably provide a range of circulating concentrations that includes the $ED_{50}$ with little or no toxicity. After administration, or between successive administrations, the circulating concentration of active agent varies within this range depending upon pharmacokinetic factors well known in the art, such as the dosage form employed, sensitivity of the patient, and the route of administration.

The exact dosage will be determined by the practitioner, in light of factors specific to the subject requiring treatment. Factors that can be taken into account by the practitioner include the severity of the disease state, general health of the subject, age, weight, gender of the subject, diet, time and frequency of administration, drug combination(s), reaction sensitivities, and tolerance/response to therapy. Long-acting pharmaceutical compositions can be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. In a particular embodiment, the daily dosage is about 0.01 mg to 30 mg/kg of body weight of the patient (e.g., 1 mg/kg to 5 mg/kg). The pharmaceutical formulation can be administered in multiple doses per day, if desired, to achieve the total desired daily dose.

Conventional methods, known to those of ordinary skill in the art of medicine, can be used to administer the pharmaceutical formulation(s) of the present invention to the patient. The pharmaceutical compositions of the present invention can be administered alone, or in combination with other therapeutic agents or interventions. Specifically, the compositions of the present invention may further comprise a plurality of agents of the present invention. The treatment of a disease in any of the described methods results in a change in the number or function of regulatory, immune-regulatory or NKT cells. This change encompasses a reduction, inhibition, or decrease in the number or function of the cells. This inhibition may be caused by the competitive displacement of activating elements from the CD1d molecule. A change may also include a stimulation or increase in the number or function of the cells. This stimulation may be caused by increased binding of the activating elements from the CD1d molecule
Synergism and Indirect Effects When tested in biological assays, the compounds selected by virtual screening for binding to LRP5/6 showed various effects upon: a) Lef activity; b) enhancement of lef activity by Wnt; and c) repression of Wnt enhancement by Dkk (as seen in Table I). Thus, the compositions of the present invention may comprise two or more compounds that modulate pathophysiological processes in a subject.

It is well known that the binding of a small molecule to a protein can alter the conformation of the protein. For instance, numerous crystallographic studies have been pursued to study the conformation of proteins with and without substrates to elicit details on binding sites and catalytic mechanisms of enzymes. As such, it could easily be understood that binding of a compound can alter the conformation of a protein such that it can enhance its activity or reduce its activity but also it can be understood that even a change in the conformation may have no effect upon the activity per se. However, it can be seen that a protein with a small molecule bound to it is not the same protein without the molecule. Thus small molecules that are able to bind to a particular target protein but had no effect upon the native protein may have effects on the target protein when it has been forced into a different conformation. The conjunction of two different compounds bound to the same protein target may consist of one molecule that had previously shown to change behavior of the system and a second that showed no effect when used alone or it is possible that it consists of two proteins, neither of which shows activity alone. The same assays that are used to test the individual compounds may then be used in the previously described assays with both compounds present, i.e. change in Lef activity, response of Lef activity to the presence of Wnt (Wnt activation), response to inhibition of Wnt by Dkk and lastly changes in the affinity of LRP5 and Dkk-AP. A series of reactions may be carried out where a compound such as gallocyanine or enzoM01 is used in the presence of other compounds that have been selected for binding to LRP5/6. On the other hand, a wider search may be employed where a matrix of various combinations of compounds is carried out.

A further aspect of the present invention is to take advantage of complementary or synergistic effects of administration of a mixture of two or more pharmacological agents. Another possibility is for two or more drugs that in combination at lower dosages can provide the same therapeutic effects as one of the drugs at a normal dosage. The advantage for this method may be reducing the expenses of the drug or there may be undesirable side effects that may be reduced by the use of a lower dosage.

EXAMPLES

Materials and Methods

Cell Culture, Transfection, Preparation of CM, and Luciferase Assay

Human embryonic kidney cell (HEK) line A293T and mouse fibroblast cell line NIH3T3 were maintained and transfected as previously described (1). Pre-osteoblast cell lines 2T3 and MC3T3 were cultured in a-MEM containing 10% FCS. For luciferase assays, cells in 24-well plates were seeded at $5 \times 10^4$ cells/well and transfected with 0.5 μg DNA/well using Lipofectamine Plus (Invitrogen, CA), as suggested by the manufacturer. The LacZ plasmid was usually used to make DNA concentrations equal for each transfection. Cell extracts were collected 24 hours after transfection. Luciferase assays were performed as previously described (1, 2). Luminescence intensity was normalized against fluorescence intensity of GFP. For the preparation of Dkk1-AP containing CM, HEK cells were seeded in 6 well-plates at $4 \times 10^5$ cells/well and transfected with 1 μg DNA/well. CMs were collected 48 hours after transfection.
Construction of Expression Plasmids and Mutagenesis The wild-type and mutant forms of human LRP5, LRP6, mouse Wnt1, Dkk1, and Dkk2 were generated by PCR using the high fidelity thermostable DNA polymerase Pfu Ultra (Stratagene, CA). HA or Flag epitope tags were introduced to the C-termini of the full-length and mutant molecules. The expression of these molecules was driven by a CMV promoter. The LEF-1 reporter gene constructs were obtained from an outside source (3).
Dkk1-AP Binding Assay and Immunoprecipitation Assay HEK cells in 24-well plates were transfected with LRP5 and its mutants. One day later, cells were washed with cold washing buffer (HBBS containing BSA and $NaN_3$) and incubated on ice with mouse Dkk1-AP conditioned medium for two hours. The cells were then washed three times with washing buffer and lysed. The lysates were heated at 65° C. for 10 minutes, and their AP activity was determined using a Tropix luminescence AP assay kit. The immunoprecipitation assays were carried out as previously described (4).

Biotinylation of Cell Surface Proteins

HEK cells were transfected with LacZ, LRP5, and $LRP5_{G171V}$ expression plasmids. The cells were labeled with 0.5 mg/ml sulfo-NHS-biotin (Pierce) in ice-cold PBS, washed and lysed as previously described (5). The cell lysate was immunoprecipitated with an anti-HA antibody and A/G-agarose protein.

Primary Osteoblast Cultures

Bone marrow stromal (BMS) osteoblast cultures from 3 month old mice were generated as previously described (6). The cells were induced to undergo osteogenic differentiation in the presence of 10 nM Dexamethasone, 8 mM β-Glycerophosphate, and 50 ug/ml ascorbic acid. The media was changed every two days.

Homology Modeling

A homology model of the third YWTD-EGF domain of LRP5 was built with ICM (Molsoft L.L.C., La Jolla, Calif.) using sequences obtained from the Swiss-Prot/TrEMBL database (Entry Name Q9UP66 (8)). The LDL receptor (Low-Density Lipoprotein) YWTD-EGF domain (PDB code 1IJQ (9)) was chosen as the template.

Virtual Screening

The UNITY™ program (Tripos, Inc.) was used to screen the National Cancer Institute (NCI) database for chemical compounds that were able to fit into the cavity formed by six-propellers at the end with Glu456. The candidate compounds were then docked into the Dkk1 binding cavities of the LRP5 domains using the FlexX™ program (Tripos, Inc.) for energy minimization (10). The chemical compounds displaying the highest binding affinities in the calculations were obtained from the Drug Synthesis & Chemistry Branch, Developmental Therapeutics Program, Division of Cancer Treatment and Diagnosis, National Cancer Institute, for further experimental tests. Second and third rounds of screenings were carried out based on the results of biochemical assays.

Evaluation of the Effects of Compounds on Bone

IIIC3 was dissolved in DMSO and diluted 1:1000 into PBS at a concentration of 0.44 mg/ml. For calvarial local injection, fifteen micro-liters of IIIC3 (0.22 mg/Kg/day), control vehicle, or positive control (b-FGF, 12.5 ug/Kg/day) were injected into the subcutaneous tissue over the right side of the calvaria of four weeks old CD-1 mice three times a day for 5 days using a injection method described previously (74, 75). Calvarias were collected 22 days after the first injection and fixed for sectioning. For systemic administration, IIIC3 (3 mg/Kg/d) and control vehicle were injected intraperitoneally into 2 month old C57B1 mice (n=19) once a day for 7 days. Then mice were rested for three weeks, and the treatment was repeated once. Three weeks after the last injection, the mice were anesthetized, and total femoral and whole body bone mineral content (BMC; grams) and bone area (square centimeters) were measured using the PIXImus small animal DXA system (GE-Lunar, Madison, Wis.), and BMD was calculated. Heads were excluded for the whole body measurement. These mice were also weighted at the time.

Wnt Activity Reporter Gene Assay

The assay was carried out as previously described (30, 78). In brief, cells in 24-well plates were seeded at $5 \times 10^4$ cells/well and transfected with 0.1 mg GFP, 0.025 ug LEF-1, 0.075 ug LEF luciferase reporter gene, and 0.3 ug LacZ per well using Lipofectamine Plus (Invitrogen, CA), as suggested by the manufacturer. Compounds and conditioned mediums were added 24 hr after transfection. Six hours later, cell extracts were collected, and luciferase assays were performed. Luminescence intensity was normalized against fluorescence intensity of GFP.

Example 1

Deletion Mutants of LRP5

A set of PCR primers were designed, PCR reactions were carried out, and PCR fragments were sucloned into vectors to generate several LRP5 deletion mutants. Deletion of the third and fourth domains (residues 646 to 1198) resulted in LRP5R12; deletion of the first and second domains (residues 1 to 646) resulted in LRP5R34; and deletion of the third domain (residues 947 to 1198) resulted in LRP5R124. (see FIG. 1A).

Example 2

Domain I of LRP5 is Essential for Mesd-Mediated LRP5 Function

Example 2.1

The G171V Mutation in the First Domain of LRP5 Disrupts LRP5 Trafficking

Interaction of LRP5 with Mesd

Figure 2A:
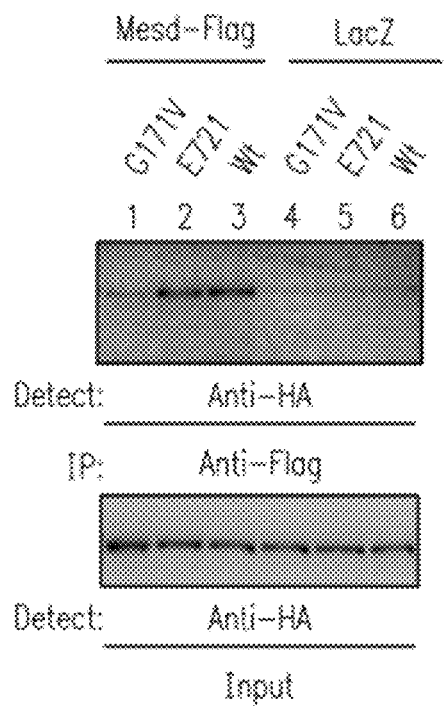
FIG. 2 illustrates that the G171V mutation disrupts LRP5 trafficking. HEK cells were transfected with expression plasmids as indicated in the figure. One day later, the cells were lysed and immunoprecipitation was carried out using an anti-Flag antibody. Mesd was Flag-tagged whereas all LRP5 molecules were HA-tagged. The G171V mutation disrupted the interactions of both LRP5 with Mesd (FIG. 2A, lanes 1 and 3), and R12 with Mesd (FIG. 2B, lanes 1 and 2), while the E721 mutation did not affect the interaction (FIG. 2A, Lanes 2 and 3). The lower panels of FIG. 2A and FIG. 2B show equal amounts of Wt and mutant LRP5 input for the immunoprecipitation. [HEK cells were transfected with the Mesd plasmid and the expression plasmids indicated in the figure.] R12TGV, R12T, R1-4 and R1-4GV (GV) are AP fusion proteins, which are LRP5 mutants lacking transmembrane domains that may be secreted in the supernatants of the cell cultures. One day later, conditioned medium (CM) was collected and centrifuged at a high speed. The supernatants were immunoprecipitated by an anti-HA antibody (FIG. 2C) or used for an AP assay (FIG. 2D). Cells were also lysed in the SDS-PAGE sample buffer and analyzed by Western blotting (lower panels of FIG. 2C and FIG. 2D). The data shows that the G171V mutation inhibited the secretion of R12 and R1-4.
FIG. 2E confirms that the G171V mutation interferes with cell surface transport of LRP5 through the use of a binding assay which detects LRP5 on the cell surface. The levels of cell surface LRP5 molecules were detected by Western analysis using streptavidin-horse radish peroxidase (SA-HRP) after the cell surfaces were biotinylated and LRP5 molecules were precipitated with anti-HA antibody (FIG. 2E, upper panel). The levels of LRP5 in the immunocomplexes are shown in the lower panel of FIG. 2E.

HEK cells were transfected with expression plasmids, as indicated in FIG. 2A. One day later, the cells were lysed and immunoprecipitation was carried out using an anti-Flag antibody. Mesd was Flag-tagged and all LRP5 molecules were HA-tagged. The results showed that the G171V mutation of domain I disrupted the interactions of both LRP5 with Mesd (FIG. 2A, lanes 1 and 3) and R12 with Mesd (FIG. 2B, lanes 1 and 2), whereas the E721 mutation of domain III showed no effect on the interaction (FIG. 2A, lanes 2 and 3).

LRP5 Mutants Do Not Efficiently Present Themselves to the Cell Surface

Figure 2B:
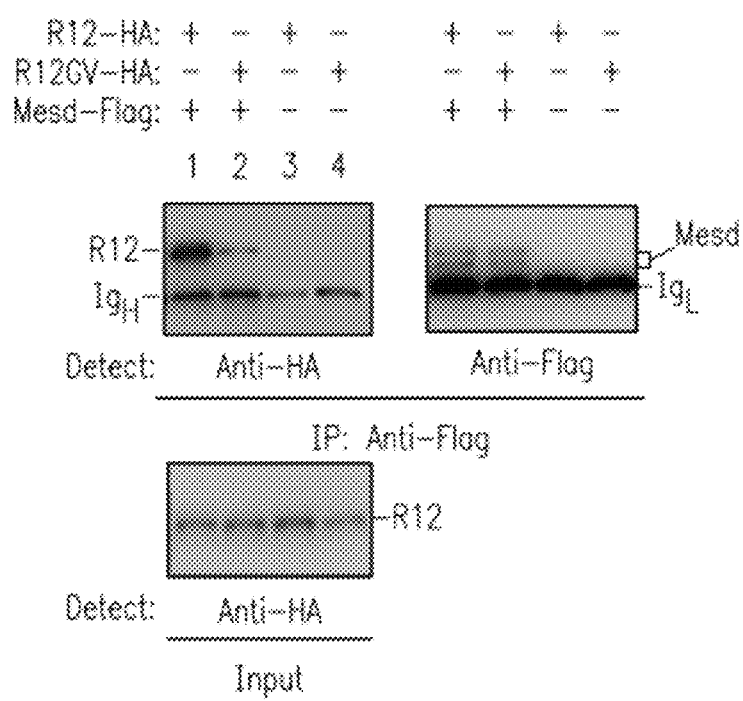
Figure 2C:
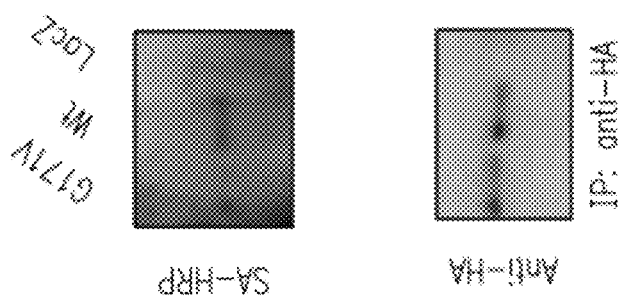
Figure 2D:
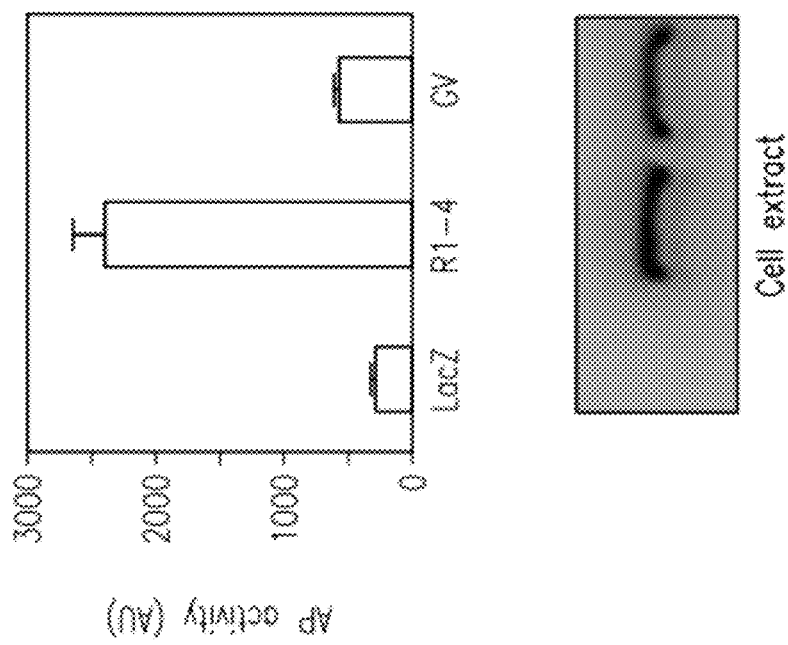

HEK cells were transfected with Mesd plasmids and expression plasmids, as indicated in FIG. 2B and FIG. 2C. R12TGV, R12T, R1-4 and R1-4GV (GV) are AP fusion proteins, which are LRP5 mutants lacking transmembrane domains that are secreted in the cell culture medium. One day later, the conditioned medium (CM) was collected and centrifuged at a high speed. The supernatant was either immunoprecipitated by an anti-HA antibody (FIG. 2C) or used for an AP assay (FIG. 2D). Cells were also lysed in the SDS-PAGE sample buffer and analyzed by Western blotting (lower panels of FIGS. 2C&D). The results indicate that the G171V mutation attenuates the presentation of LRP5 to the cell surface.

Evaluation of Cell Surface LRP5 Levels

Figure 2E:
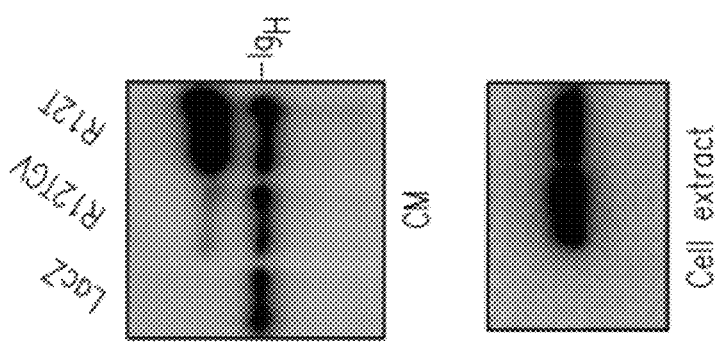

HEK cells were transfected with LacZ, wildtype HA-LRP5 or HA-LRP5G171V expression plasmids. The levels of cell surface LRP5 molecules were detected by Western analysis using streptavidin-horse radish peroxidase (SA-HRP) after the cell surfaces were biotinylated and the LRP5 molecules were precipitated with anti-HA antibody (FIG. 2E upper panel). The levels of LRP5 in the immunocomplexes are shown in the lower panel. These results show a decrease in cell surface presentation of the G171V mutant.

Example 2.2

Figure 3A:
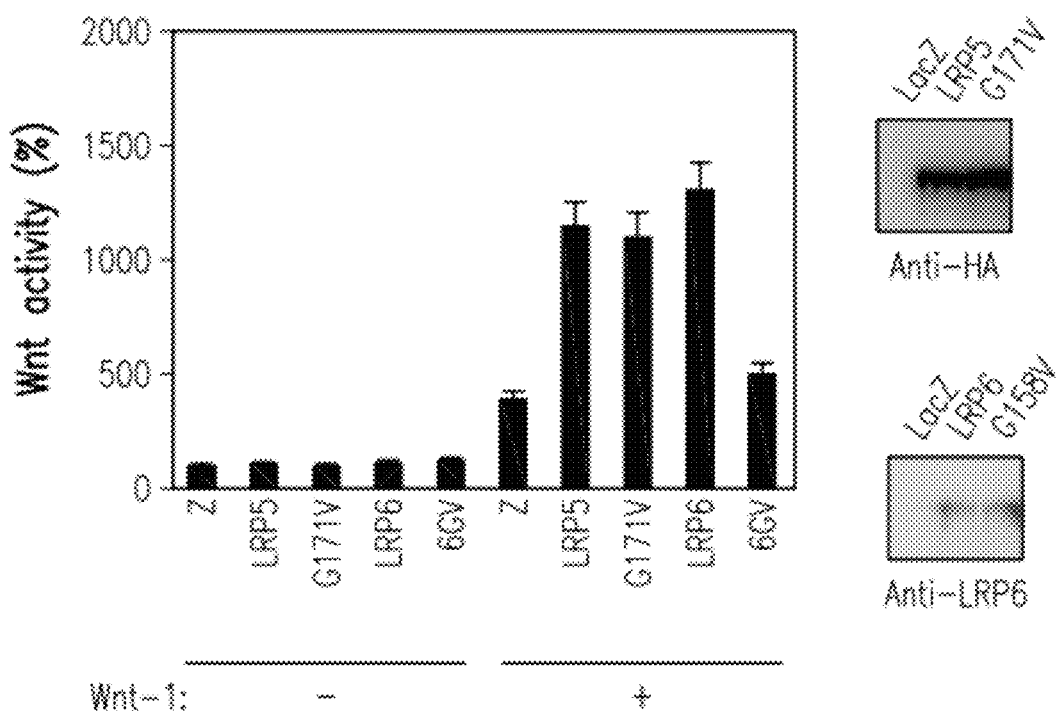
FIG. 3 shows that the HBM G171V mutation of LRP5 is less susceptible to Dkk1-mediated inhibition of coexpressed Wnt activity. The left panel of FIG. 3A shows that when HEK cells were transfected with plasmids as indicated together with LEF-1 luciferase reporter plasmids in the presence or absence of Wnt1, the HBM G171V mutation did not lead to an increase in LEF-1-dependent transcriptional activity compared to the wildtype (Wt) LRP5 (LRP5$_{Wt}$). The right panel of FIG. 3A shows expression levels of LRP5, LRP5$_{G171V}$, LRP6, and LRP6$_{G158V}$ as determined by antibodies specific to the HA tag carried by LRP5 proteins or anti-LRP6 antibodies.
FIG. 3B shows that when HEK cells were transfected with LEF-1 luciferase reporter plasmids, Wnt-1, Dkk1 and Kremen in the presence of Wt or G171V LRP5 as indicated in the figure. LEF-1 reporters-indicated Wnt activity is significantly higher in HEK cells expressing LRP5$_{G171V}$ than those expressing LRP5$_{Wt}$ when Dkk is present. The protein expression levels of Dkk1, Kremen and LRP5 were verified by Western blotting, as shown in FIG. 3C.

$LRP5_{G171V}$ is Less Susceptible to Dkk1-Mediated Inhibition of the Activity of Coexpressed Wnt Effects of the G171V Mutation on Canonical Wnt Signaling Activity HEK cells were transfected with plasmids, as indicated in FIG. 3A, together with LEF-1 expression plasmids, LEF-1 luciferase reporter plasmids and GFP expression plasmids. One day later, the cells were lysed. GFP levels and luciferase activity of the lysed cells were determined and normalized against GFP levels, as described in the Materials & Methods. The activity from cells transfected with LacZ was taken as 100% to establish the control. The expression of LRP5, LRP5$_{G171V}$, LRP6, and LRP6$_{G158V}$ was detected using an antibody specific to the HA tag carried by LRP5 proteins, or an anti-LRP6 antibody (FIG. 3A). The results indicate that the HBM G171V mutation did not lead to an increase in LEF-1-dependent transcriptional activity compared to wildtype (Wt) LRP5 (LRP5$_{Wt}$) by itself or in transducing signals for coexpressed Wnt. LEF-1 is a down-stream target transcription factor of the canonical Wnt signaling pathway. Its activity, measured by a luciferase reporter gene assay, has been widely used to gauge the canonical Wnt activity (12, 20). Thus, LRP5$_{G171V}$ is neither constitutively active nor more competent in transducing Wnt signaling. Surprisingly, the corresponding mutation on LRP6, a substitution of a Val residue for Residue G-158, rendered it unable to act synergistically with Wnt-1 (FIG. 3A), likely inactivating the receptor.

Effects of the G171V Mutation on Canonical Signaling Activity Stimulated By Coexpressed Wnt1

Figure 3B:
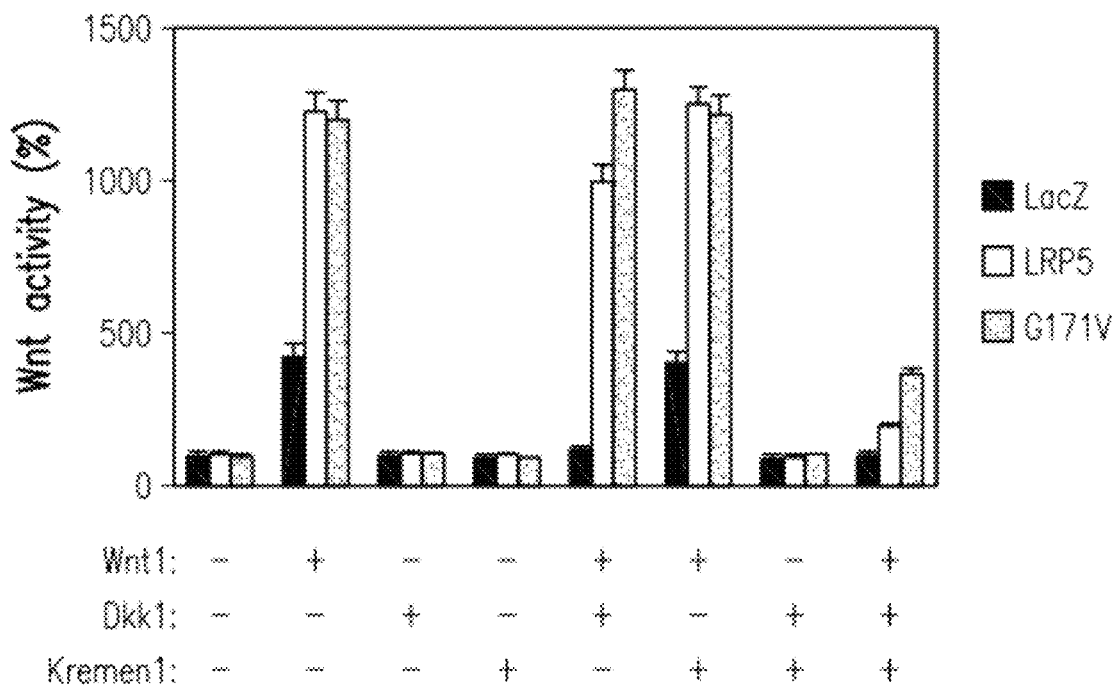
Figure 3C:
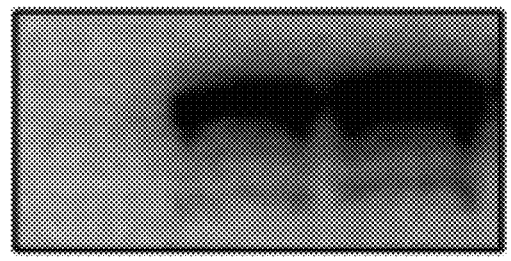
Figure 3C:
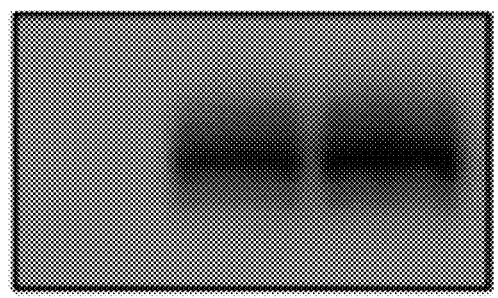
Figure 3C:
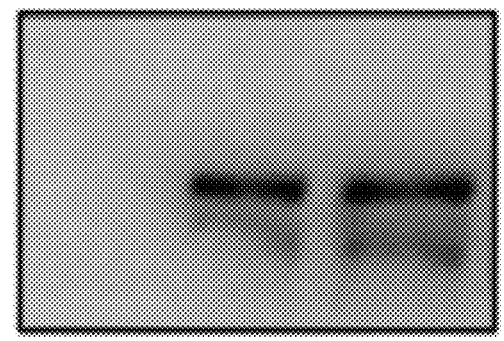

HEK cells were transfected with plasmids of LEF reporters, Wnt-1, Dkk1 and Kremen in the presence of LRP5$_{Wt}$ or LRP5$_{G171V}$, as indicated in FIG. 3B. Human HEK cells were transfected with LacZ, or cotransfected with Dkk1, Kremen1 and Wnt1 in the presence of LRP5 or LRP5$_{G171V}$. In the presence of both Kremen1 and DKK1, Wnt showed higher activity in HEK cells expressing LRP5$_{G171V}$ than those expressing LRP5$_{Wt}$ (FIG. 3B). These results indicate that the LRP5$_{G171V}$ transduces more signals than the wild type in the presence of Dkk1. To ensure that the difference was not a result of multi-plasmid transfection, the protein expression of Dkk1, Kremin1 and LRP5 (FIG. 3C) was examined. Similar results of increased resistance to Dkk-mediated inhibition of autocrine Wnt1 activity were also observed in NIH3T3 cells and two osteoblast-like cell lines, MC3T3 and 2T3.

Example 2.3

Binding of Dkk1-AP to LRP5 and LRP5 Mutants

Figure 4:
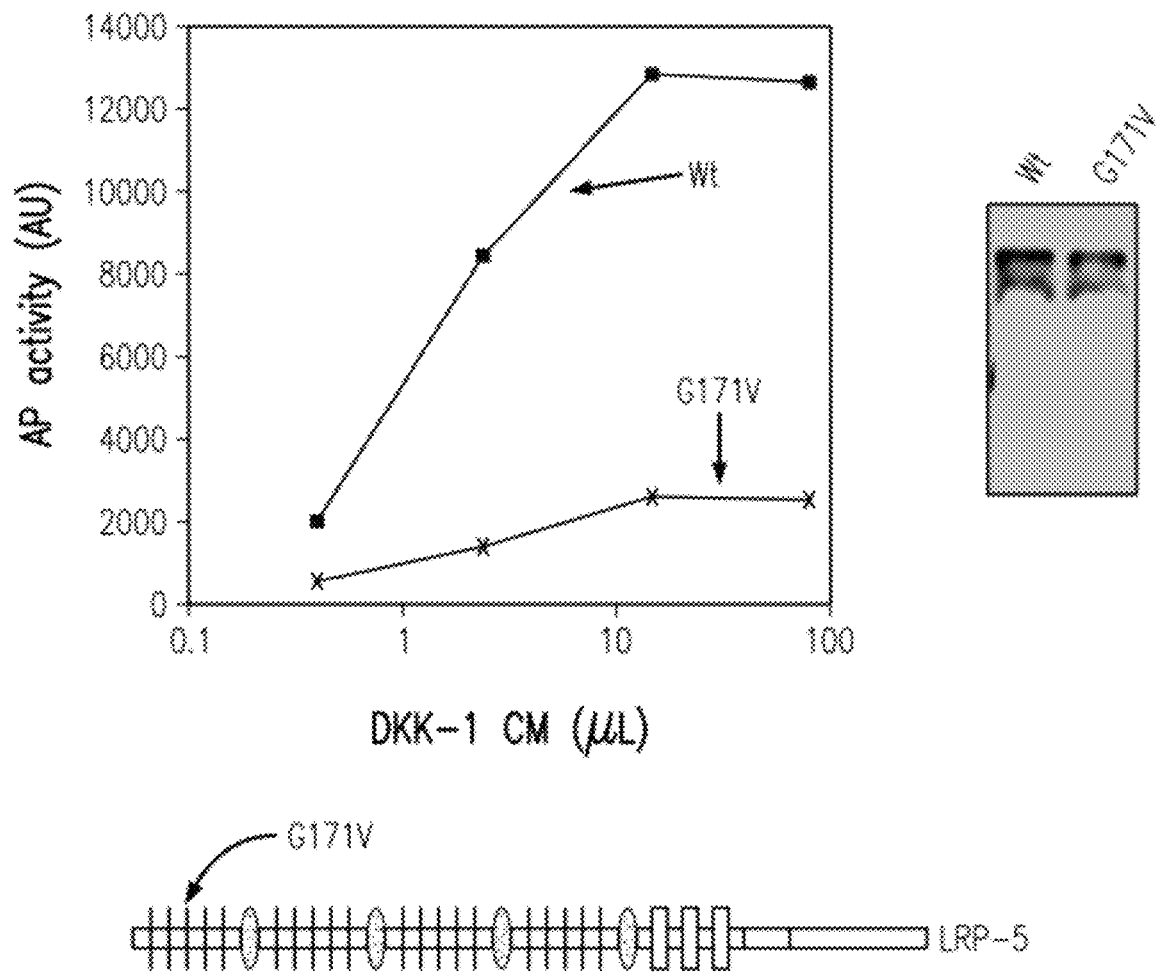
FIG. 4 illustrates that cells expressing LRP5G171 show less Dkk1 binding sites than those expressing LRP5$_{Wt}$ (FIG. 4A).

HEK cells were transfected with Mesd plasmids and LRP5 plasmids, as indicated in FIG. 4, and incubated on ice with CM prepared from HEK cells expressing Dkk1-AP. The AP activity was determined in arbitrary units (AU), as described in the Materials and Methods. The expression of Wt and mutant LRP5 molecules are shown in FIG. 4B. These results indicate that cells expressing the LRP5$_{G171V}$ mutant show less apparent Dkk binding than those expressing LRP5$_{Wt}$ (FIG. 4A), which is consistent with less LRP5$_{G171V}$ on cell surfaces, shown in FIG. 2.

Example 3

Domain II of LRP5 is Required for Wnt Activity

Figure 5:
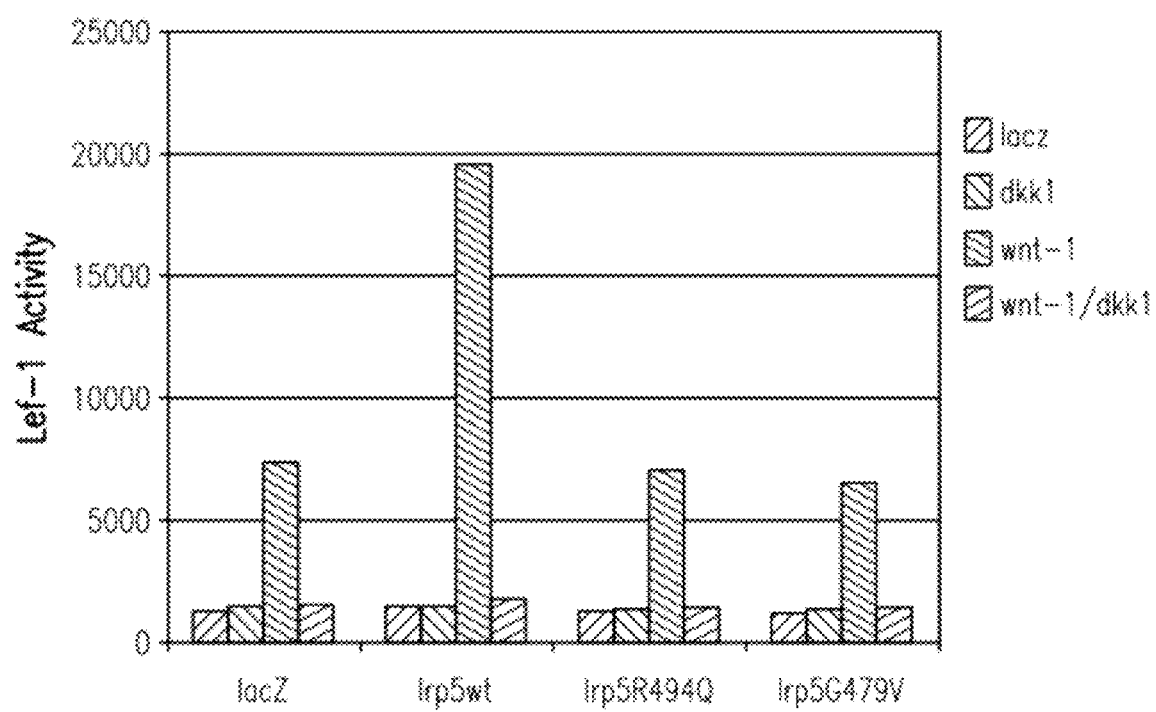
FIG. 5 shows that the second domain of LRP5 is required for Wnt activity. HEK cells were transfected with LEF activity reporter plasmids and expression plasmids. One day later, LEF reporter activity was measured, as previously described. The results in FIG. 5 show that LRP5$_{R494Q}$ and LRP5$_{G479V}$ (LRP5 with point mutations in the second domain) may abolish Wnt signaling compared to LRP5$_{Wt}$.

HEK cells were transfected with the LEF activity reporter plasmids and expression plasmids, as indicated in FIG. 5. Expression plasmids LRP5R494Q and LRP5G479V are LRP5 receptors with point mutations in their second domain. One day later, the cells were lysed. GFP levels and luciferase activity of the lysed cells were determined and normalized against GFP levels, as described in the Materials & Methods. FIG. 5 shows that LRP5R494Q and LRP5G479V can abolish Wnt signaling, as compared to LRP5$_{Wt}$. These results indicate that Domain II is required for Wnt activity.

Example 4

Domain III is Required for Dkk-Mediated Inhibition

Example 4.1

Analysis of Domain III

The prevailing hypothesis for explaining why LRP5 G171V is less susceptible to Dkk1-mediated inhibition has been that the mutation could disrupt the interaction between LRP5 and Dkk1. It is reasonable to hypothesize that the first YWTD repeat domain that contains G171 is required for Dkk1-mediated antagonism. To test this hypothesis, two LRP5 deletion mutants were generated: LRP5R12 with a deletion of the third and fourth YWTD repeat domains, and LRP5R34 with a deletion of the first and second YWTD repeat domains (FIG. 1). To further delineate the sequence that is required for Dkk1-mediated inhibition, an additional LRP5 mutant, LRP5R124, was generated in which the third YWTD repeat domain was deleted (FIG. 1).

Functional Analysis of Domain III

Figure 6A:
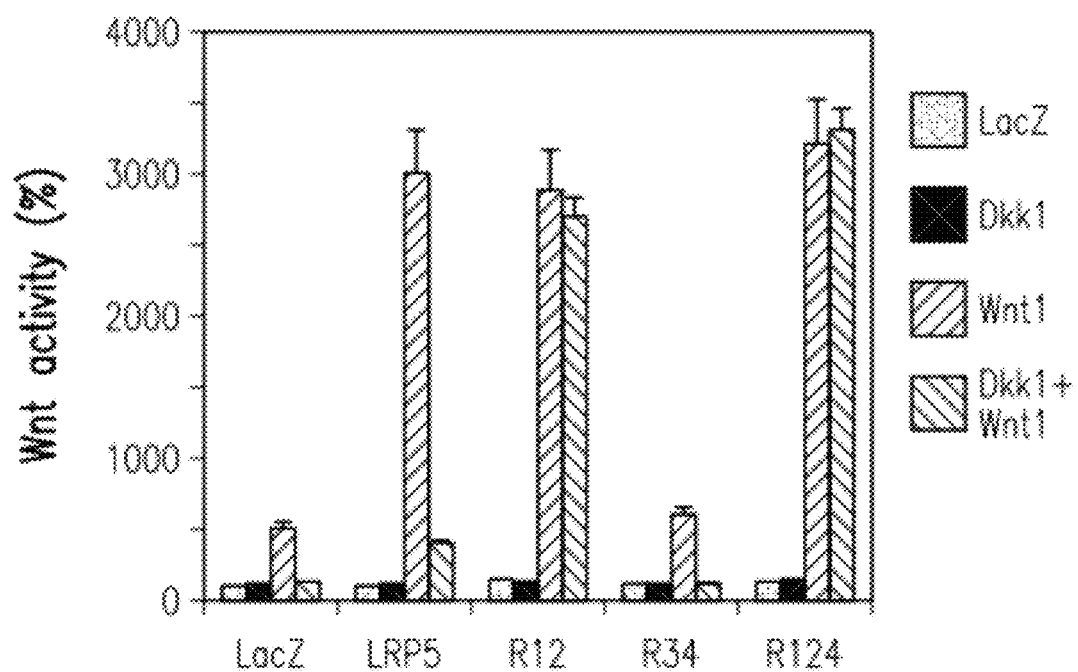
FIG. 6A shows that the third YWTD repeat domain is required for Dkk-mediated inhibition. HEK cells were transfected with LEF activity reporter plasmids, Kremen1 plasmids and expression plasmids. LRP5R12 or LRP5R124, but not LRP5R34, could still potentiate Wnt-stimulated LEF-1 activity, suggesting that either LRP5R12 or LRP5R124 retains the Wnt coreceptor function. However, Dkk1 could not inhibit Wnt signaling when LRP5R12 or LRP5R124 was present despite the coexpression of Kremen. This suggests that the third YWTD repeat domain is required for Dkk1-mediated inhibition. The expression level of LRP5$_{Wt}$ and its mutant molecules are shown in FIG. 6B.
Figure 6B:
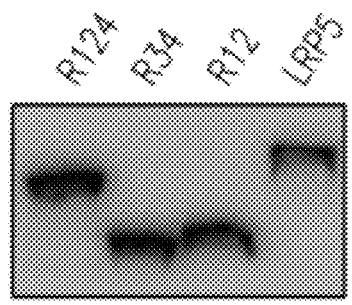
FIG. 6 illustrates that the third domain of LRP5 is required for Dkk-mediated antagonism.
FIG. 6C illustrates that LRP5R34 contains Dkk1 binding sites and that E721 in R34 is required for Dkk1 binding.
FIG. 6D is a schematic representation of the mutations.

HEK cells were transfected with the LEF activity reporter plasmids, Kremen1 plasmid and expression plasmids as indicated in the FIG. 6A. The expression of Wt LRP5 and its mutant molecules were shown in the FIG. 6B. The result shows that LRP5R12 or LRP5R124, but not LRP5R34, could still potentiate Wnt-stimulated LEF-1 activity (FIG. 6A), suggesting that LRP5R12 or LRP5R124 retains the Wnt coreceptor function. However, Dkk1 could not inhibit Wnt signaling when LRP5R12 or LRP5R124 was present (FIG. 6A). This suggests that the domain III is required for Dkk1-mediated inhibition.

Binding of DKK1-AP to LRP5 and LRP5 Mutants

Figure 6C:
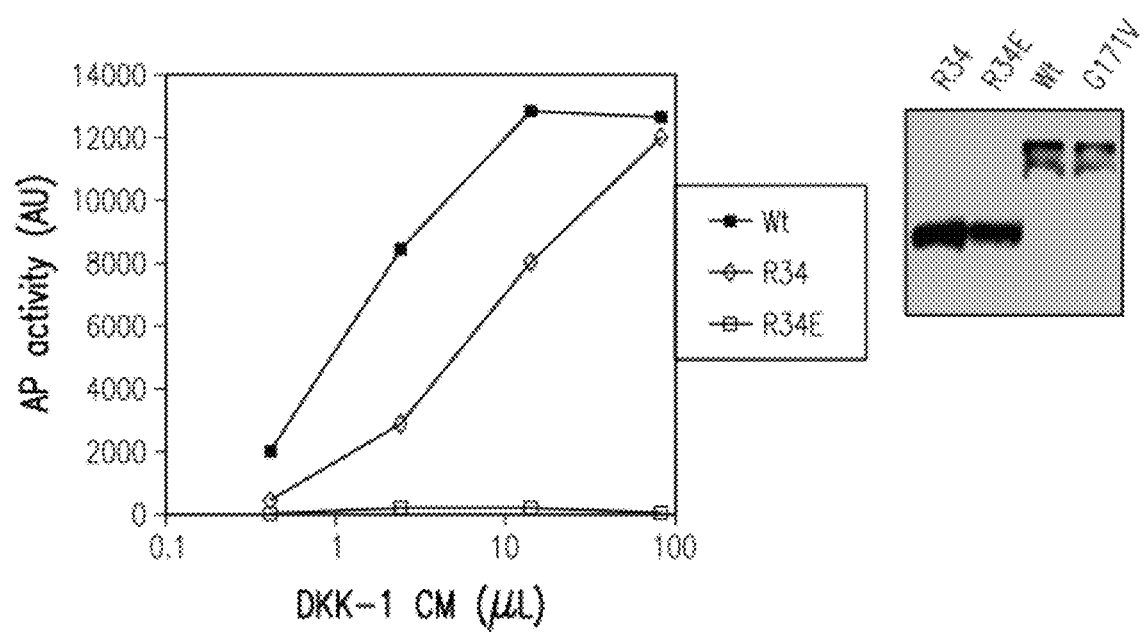
Figure 6D:
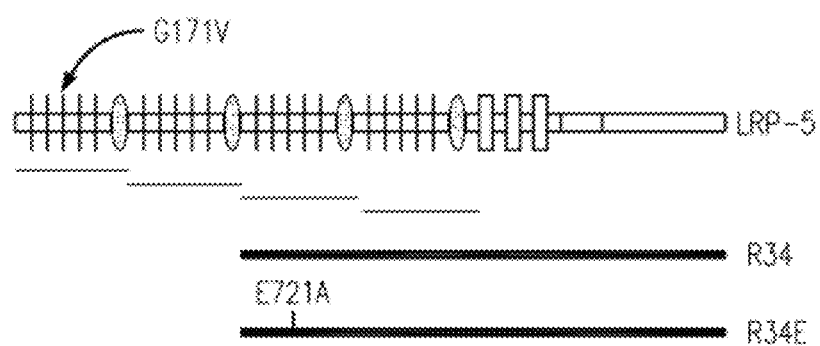

HEK cells were transfected with Mesd plasmids and LRP5 plasmids, as indicated in FIG. 6C, and incubated on ice with CM prepared from HEK cells expressing Dkk1-AP. The AP activity was determined in Arbitrary Units, as described in the Materials and Methods. The expression of Wt and mutant LRP5 molecules are shown in the right panel of FIG. 6C. These results indicate that LRP5R34 contains Dkk1 binding sites, and that E721 in R34 is required for Dkk1 binding. (FIG. 6C).

Example 4.2

Identification of the Amino Acid Residues on the Interaction Surface on Domain III which are Required for Dkk Inhibition As deletion of the entire third YWTD repeat domain may cause gross conformational changes in LRP5, as will be described herein, point mutations in this domain were created that could disrupt Dkk 1-mediated inhibition.

Figure 7A:
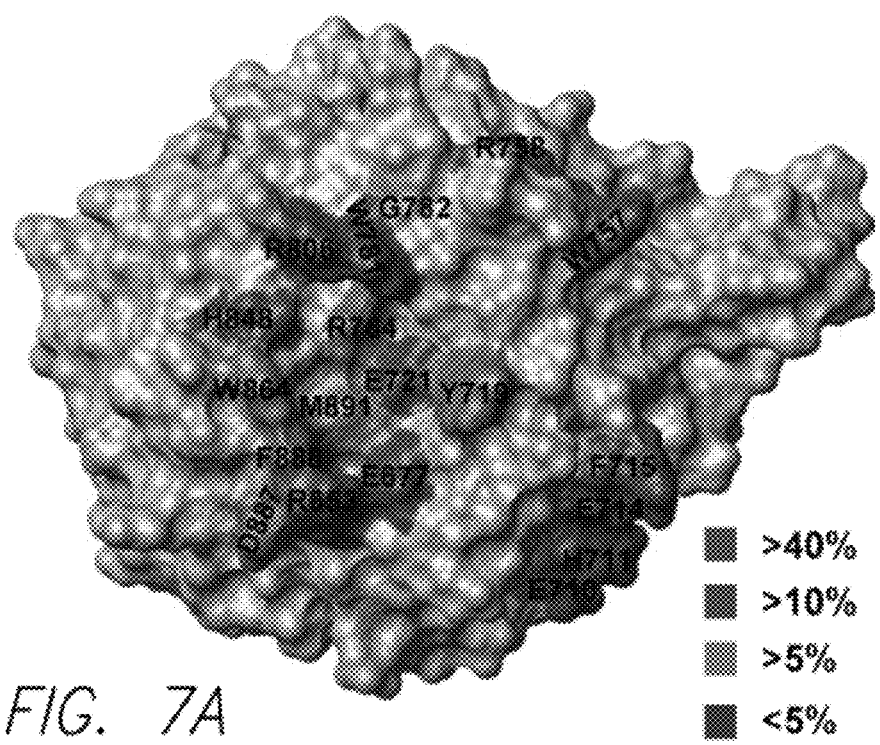
In FIG. 7A, the space filled model of the third YWTD repeat domain was deduced based on the structure of the LDL receptor YWTD repeat domain (13). Based on the three-dimensional structure, 19 LRP5 mutants containing Ala substitution mutations on the surface of the third YWTD repeat domain were generated. The ability of these mutant LRP5 proteins to resist Dkk1-mediated inhibition was determined. Nine of the mutants (more than 5%) showed altered sensitivity to Dkk1-mediated inhibition, and they all contained mutations that were localized on the same surface.

Schematic Representation of Ala Substitution Mutations on Interaction Surface III The space filled model of Domain III was deduced based on the structure of the LDL receptor YWTD repeat domain (13). The homology model of Domain III of Dkk1 was built with ICM (Molsoft L.L.C., La Jolla, Calif.) using sequences obtained from the Swiss-Prot/TrEMBL database (Entry Name Q9UP66 [18]). The Low-Density Lipoprotein (LDL) receptor YWTD-EGF domain (PDB code 1IJQ (22)) was chosen as the template. Based on the three-dimensional structure, 19 LRP5 mutants were generated containing Ala substitution mutations on the surface of Domain 111 (FIG. 7A). The ability of these mutant LRP5 proteins to resist Dkk1-mediated inhibition was determined and is shown in FIG. 7A. Nine of the mutants showed altered (more than 5%) sensitivity to Dkk1-mediated inhibition, and contained mutations localized on the same surface (FIG. 7A).

Effect of Representative Point Mutations on the Wnt Coreceptor Activity of LRP5

Figure 7B:
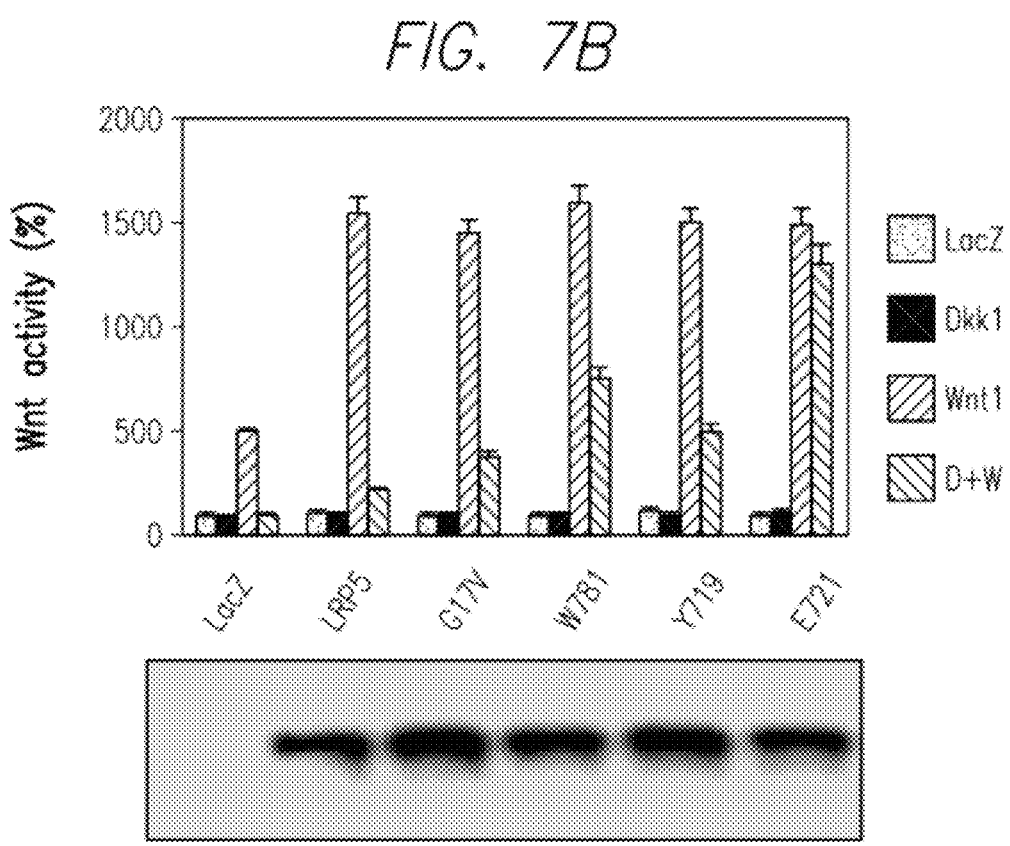
In FIG. 7B, HEK cells were transfected with LEF activity reporter plasmids, Kremin1 plasmid, and expression plasmids. The expression of Wt and mutant LRP5 molecules are shown in the lower panel. Among 19 mutations, the E721 mutation showed the strongest effect on Dkk1-mediated inhibition of Wnt, followed by W781, and then Y719. LRP5$_{G171V}$ also showed an effect on the Dkk1-mediated inhibition of Wnt.

HEK cells were transfected with LEF activity reporter plasmids, Kremen1 plasmids and expression plasmids, as indicated in FIG. 7B. The expression of Wt and mutant LRP5 molecules are shown in the lower panel. Among 19 mutations, the E721 mutation showed the strongest effect on Dkk1-mediated inhibition, followed by W781, and Y719 (FIG. 7B).

Mutations of E721-corresponding residues in the first and second YWTD repeat domains (D111 and D418, respectively) did not significantly alter the sensitivity to Dkk-mediated inhibition. All the mutants that were resistant to Dkk1-mediated inhibition were also resistant to Dkk2-mediated inhibition. All this data supports the conclusion that the third YWTD repeat domain is required for Dkk-mediated inhibition.

An obvious explanation for the requirement of the third YWTD repeat domain for Dkk-mediated inhibition is that this domain is responsible for Dkk1 binding. The direct binding of Dkk1-AP fusion protein to LRP5 expressed on the surface of HEK cells was measured (23).

Example 5

Screening Compounds that Interact with the Specified Domain III of LRP5

Example 5.1 (A)

Screening Compounds Using Domain III as a Template

Virtual Screening

The UNITY™ program (Tripos, Inc.) was used to screen the National Cancer Institute (NCI) database (http://129.43.27.140/ncidb2) for chemical compounds that were able to fit into the cavity on Domain III. This database is freely searchable and includes the coordinates of 250,251 small chemical compounds. A search query was designed to consist of R764 and E721 with 0.3 Å tolerance, and a hydrophobic center with 1.0 Å tolerance that is 3.2 Å away from Trp781, pointing towards the cavity. Taking the flexibility of the compounds into consideration, the Directed Tweak algorithm in the UNITY™ program allowing for a rapid, conformationally flexible three dimensional search (21) was applied.

Figure 8A:
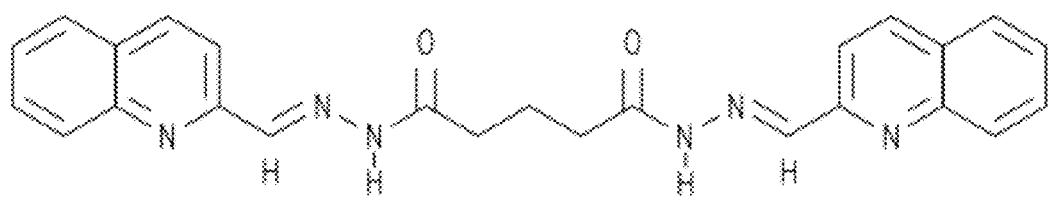
FIG. 8 shows the two dimensional structures of three compounds obtained from the National Cancer Institute (NCI). NCI106164 (FIG. 8A) shows a 68% inhibitory effect on Dkk1 binding while NCI39914 (FIG. 8B) and NCI660224 (FIG. 8C) increase Dkk1 binding by 654% and 276%, respectively.
Figure 8B:
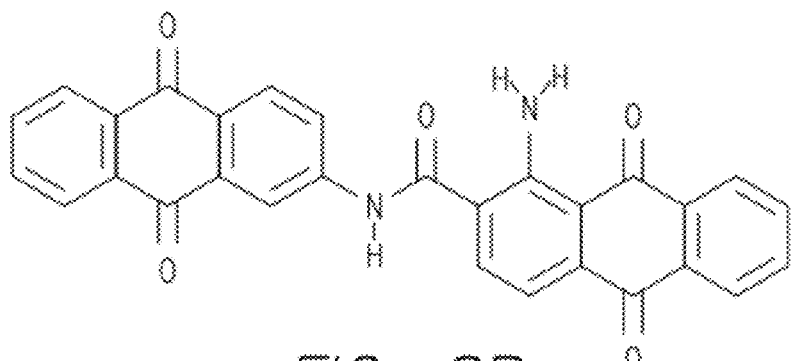
Figure 8C:
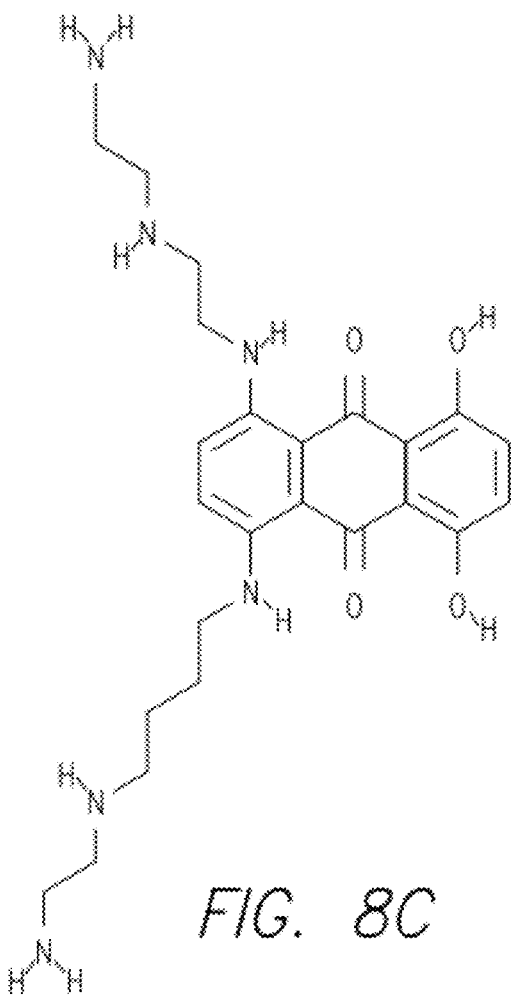
Figure 9A:
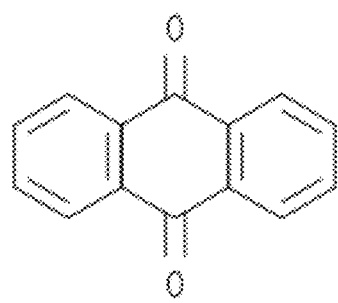
FIG. 9 illustrates the two-dimensional structure of anthra-9,10-quinone (FIG. 9A), a common substructure in NCI39914 and NCI660224.
FIG. 9B shows the two-dimensional structure of NCI 657566.
FIG. 9C shows the template that was used for the two-dimensional similarity search.
Figure 9B:
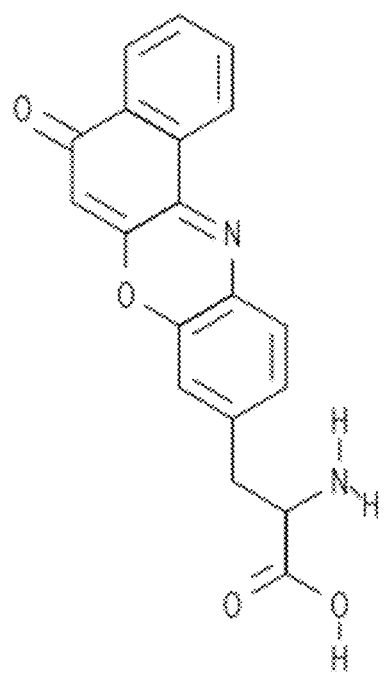
Figure 9C:
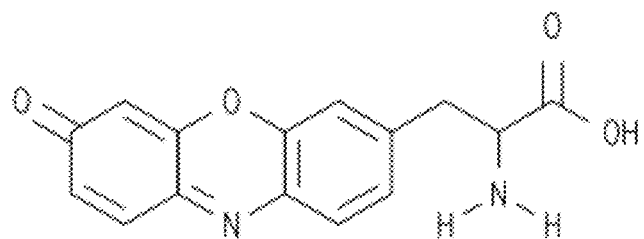
Figure 10A:
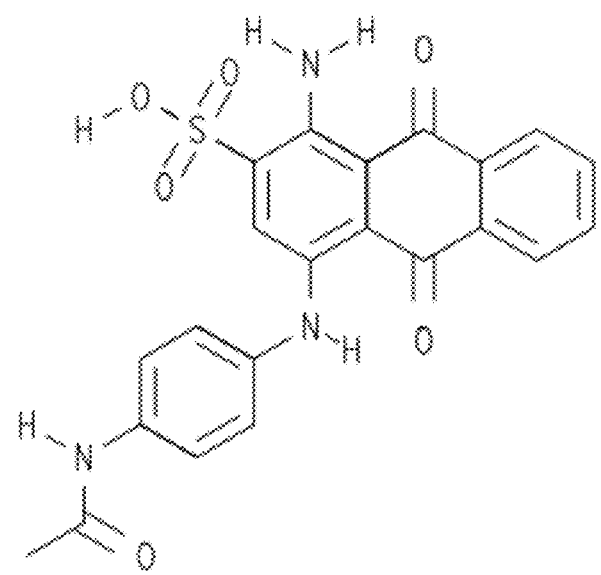
FIG. 10 shows the two-dimensional structure of compounds NCI366218 (IIC8, FIG. 10A) and NCI8642 (IIIC3, FIG. 10B) which specifically interrupt Dkk1-LRP5 interaction and reverse the inhibition of Wnt signaling by Dkk1.
Figure 10B:
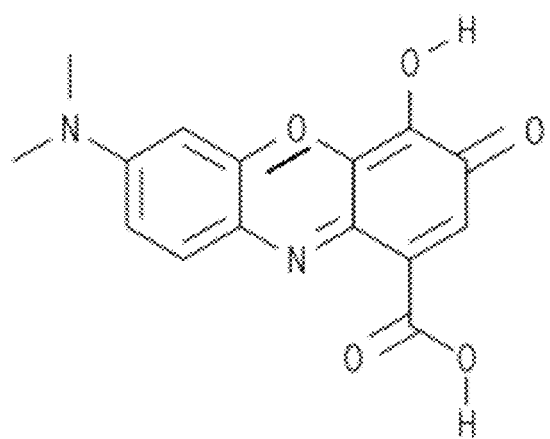

The candidate compounds obtained using the UNITY™ program were then docked into the Dkk1 binding surface using the FlexX™ program (Tripos, Inc.) for energy minimization (17), which quickly and flexibly docks ligands to protein-binding sites (44). Residues E721, W864, Y719, R764, D877, F888, G782, W781 and M891, shown to be critical for Dkk1 recognition (FIG. 7A), were considered in the calculations. Following the docking procedures, the compounds were then ranked based on their predicted ability to bind to the Dkk1 binding pocket using the Cscore™ program. Cscore™ generated a relative consensus score based on how well the individual scoring functions of the protein-ligand complexes performed (8). The Cscore™ were then subjected to final manual visual inspection. While 40 compounds with the highest consensus scores were requested from NCI, only 17 were obtained due to unavailability. These compounds were then subjected to the Dkk-1 binding assay. Three of these compounds were found to have an effect on the binding of Dkk1 to LRP-5: NCI106164 (also referred to as IC14) (FIG. 8A) inhibited Dkk1 binding by 32%, while NCI39914 (also referred to as IC13) (FIG. 8B) and NCI660224 (also referred to as IC5) (FIG. 8C) stimulated Dkk1 binding by 645% and 275%, respectively. The stimulatory effect of NCI39914 and NCI660224 may be due to the enhanced interaction of these compounds with the Dkk1 binding cavity of the third domain. This enhancement could result from bridging of the gap that exists between the interaction surfaces of Dkk1 and LRP5. Since anthra-9,10-quinone (FIG. 9A) is a common substructure among compounds NCI39914 (IC13) and NCI660224 (IC5), anthra-9,10-quinone may play a key role in the binding interaction with LRP5. A two dimensional search for compounds found in the NCI database that are similar to anthra-9,10-quinone was performed using the similarity search algorithm of the UNITY™ program. The hits were then docked with the FlexX™ program, as previously described. 25 compounds with the highest scores were obtained from NCI and tested. Compounds NCI657566 (FIG. 9B) and NCI366218 (FIG. 10A) were able to reverse the Dkk1-mediated inhibition of Wnt signaling. A new two dimensional similarity search was conducted using a NCI366218-derived template shown in FIGS. 9C and 13 candidate compounds were identified. Biological assays (as described below) showed that NCI 8642 (FIG. 10B) was the best compound for the reversal of Dkk-mediated inhibition of Wnt signaling and the disruption of Dkk1 binding to LRP5.

Biological Assays

Biological assays were used to screen the compounds identified by virtual screening.

Dkk-1 Binding Assay

The binding of Dkk1-AP to HEK cells expressing full length LRP5 or LRP5R34 mutant lacking the first two domains was performed as described in EXAMPLE 2 (FIG. 4). The first batch of 17 compounds was initially screened for the inhibition of Dkk1 binding to full length LRP5. It should be noted that NCI106164 (IC14) showed a 68% inhibitory effect on Dkk1 binding, while NCI39914 (IC5) and NCI660224 (IC3) stimulated Dkk1 binding by approximately 654% and 276%, respectively (see Table I). As for the enhancement of the binding by IC5 and IC13, the effect may be the result of receptor oligomerization or allosteric effects exerted on the receptors by these symmetric molecules. Importantly, IC5, IC13 (FIG. 8B), and IC15 (FIG. 8C) all contain an anthra-9,10-quinone core structure, suggesting that the quinone structure may provide basic interacting forces for the molecules to interact with the cavity. The presence of several aromatic amino acid residues in the Dkk-interacting cavity supports this idea.

TABLE I

Effects of chemical compounds (2 mg/ml) on DKK1 binding

| Compound 1000 ul DMSO | | Binding Inhibitory Rate of DKK1 % LRP5 WT |
|---|---|---|
| DMSO | 1:100 | 100 |
| 270071 | IC1 | 97 |
| 45123 | IC2 | 117 |
| 37815 | IC3 | 85 |
| 382917 | IC4 | 108 |

TABLE I-continued

Effects of chemical compounds (2 mg/ml) on DKK1 binding

| Compound 1000 ul DMSO | | Binding Inhibitory Rate of DKK1 % LRP5 WT |
|---|---|---|
| 660224 | IC5 | 276 |
| 38290 | IC6 | 101 |
| 649827 | IC7 | 88 |
| 70694 | IC8 | 180 |
| 648597 | IC9 | 79 |
| 618567 | IC10 | 96 |
| 657726 | IC11 | 90 |
| 12156 | IC12 | 127 |
| 39914 | IC13 | 654 |
| 106164 | IC14 | 68 |
| 16221 | IC15 | 73 |
| 651656 | IC16 | 96 |
| 67653 | IC17 | 107 |

TABLE II

Wnt activity assay screening of Batch II

| Compound | Basal | Wnt | Wnt + Dkk |
|---|---|---|---|
| Control | 100 | 1000 | 100 |
| 127133 | 97 | 170 | 106 |
| 1743 | 113 | 670 | 229 |
| 39963 | 115 | 970 | 114 |
| 337836 | 116 | 870 | 81 |
| 37608 | 26 | 0 | 10 |
| 372294 | 95 | 0 | 13 |
| 123823 | 79 | 220 | 137 |
| 366218 | 117 | 1220 | 476 |
| 342051 | 107 | 50 | 152 |
| 39957 | 103 | 40 | 16 |
| 4997 | 114 | 990 | 113 |
| 116405 | 88 | 230 | 23 |
| 641424 | 111 | 190 | 19 |
| 373532 | 99 | 110 | 27 |
| 25869 | 105 | 880 | 176 |
| 310659 | 128 | 130 | 21 |
| 28561 | 90 | 630 | 110 |
| 51530 | 130 | 0 | 0 |
| 128436 | 166 | 0 | 0 |
| 209942 | 100 | 750 | 136 |
| 366105 | 107 | 100 | 0 |
| 159858 | 121 | 80 | 147 |
| 106164 | 88 | 350 | 64 |
| 647082 | 95 | 940 | 105 |
| 657566 | 105 | 1140 | 227 |

TABLE III

Wnt activity assay screening of Batch III

| Compound | Basal | Wnt | Wnt + Dkk |
|---|---|---|---|
| Control | 100 | 1000 | 240 |
| 37089 | 102 | 1090 | 230 |
| 97309 | 90 | 430 | 105 |
| 8642 | 101 | 1220 | 1020 |
| 66425 | 85 | 1010 | 250 |
| 113914 | 92 | 1180 | 360 |
| 364163 | 0 | 0 | 0 |
| 115934 | 88 | 800 | 190 |
| 110317 | 90 | 1110 | 250 |
| 3751 | 97 | 1090 | 304 |
| 28627 | 107 | 800 | 403 |
| 10573 | 87 | 710 | 245 |
| 620055 | 10 | 1 | 6 |
| 37179 | 92 | 960 | 240 |

Table II & Table III

NIH3T3 cells were transfected with Wnt activity luciferase reporter gene. The next day, the compounds were dissolved in DMSO at 2 mg/ml and diluted at 20 ug/ml into tissue culture medium (Basal), medium containing Wnt3a (Wnt) or medium containing both Wnt3a and Dkk1 (Wnt+Dkk). DMSO without any compound served as the control. Six hours later, the cells were lysed and Wnt activity was determined using a luciferase assay. The data shown is percent basal activity. Compounds that show more than a 100% reversal of Dkk inhibition without affecting Wnt activity are shown in red.

Wnt Activity Assay

The second and third domains of LRP5 are required for Wnt signaling, and these domains probably directly interact with Wnt molecules. Since these domains share extensive amino acid sequence homology, it is probable that certain compounds that bind to the third domain may also bind to the first two domains, potentially causing the inhibition of Wnt activity. The second batch of compounds were initially screened using the Wnt activity assay and subsequently screened using the binding assay to confirm that compounds reversing Dkk inhibition inhibited Dkk binding to LRP5. As shown in Table II, 25 compounds from the second batch were screened using the Wnt activity assay. Specifically, NIH 3T3 cells were transfected with Wnt activity luciferase reporter gene. The next day, the compounds were dissolved in DMSO at 2 mg/ml and diluted at 20 ug/ml into tissue culture medium (B basal) containing Wn3a (Wnt) or medium containing both Wnt3a and Dkk1 (Wnt+Dkk). DMSO without any compound served as the control. Six hours later, the cells were lysed and Wnt activity was determined using a luciferase assay. The data shown is percent basal activity. The compounds were examined for the following: 1) basal reporter activity inhibition; 2) Wnt activity inhibition; and 3) reversal of Dkk-mediated inhibition of Wnt activity. As shown in Table II, 17 out of 25 compounds were found to inhibit Wnt activity by more than 30%. Two compounds, NCI366218 and NCI657566, were found to reverse Dkk1 mediated inhibition of Wnt signaling without affecting Wnt activity.

To determine which compounds reverse Dkk-mediated inhibition, a third batch of compounds was identified using virtual screening. 13 compounds were identified and subjected to Wnt activity screening. As shown in Table III, three compounds were found to greatly inhibit Wnt activity, and one compound (NCI8642) significantly reversed Dkk-mediated inhibition.

Figure 11A:
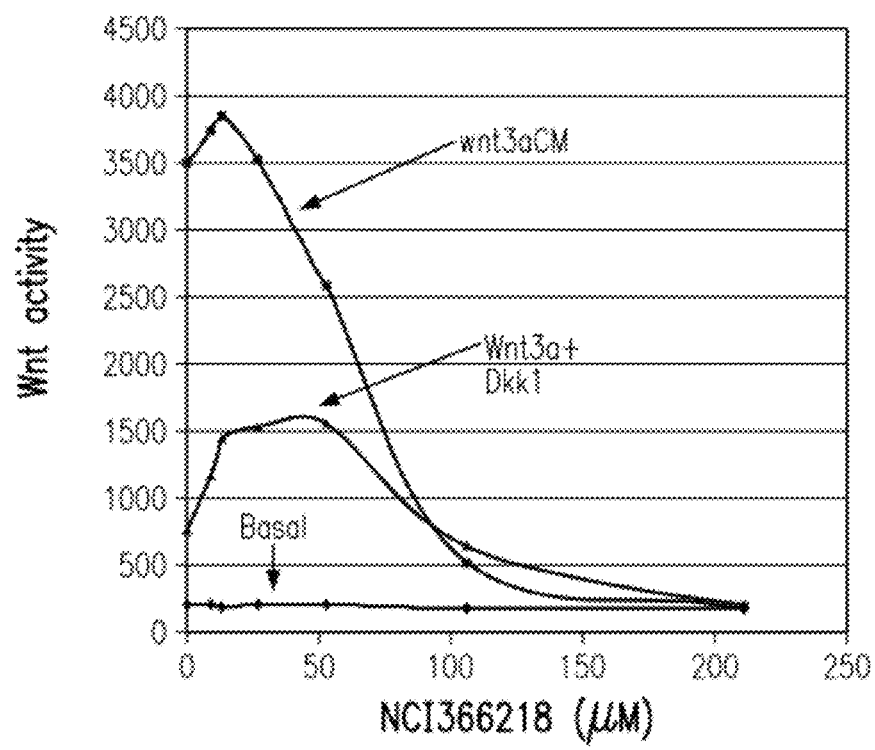
FIG. 11 illustrates that NCI366218 and NCI8642 reverse Dkk1 inhibition. HEK cells were transfected with LRP5 plasmid together with a LEF-1 expression plasmid, LEF-1 luciferase reporter plasmid and a GFP expression plasmid. The cells were then treated with different concentrations of the NCI366218 and NCI8642 compounds and subsequently treated with control CM, Wnt3a CM or Wnt 3a/Dkk1 CM mixture for 6 hrs. The reporter activity from cells treated with DMSO was taken as 100%.
Figure 11B:
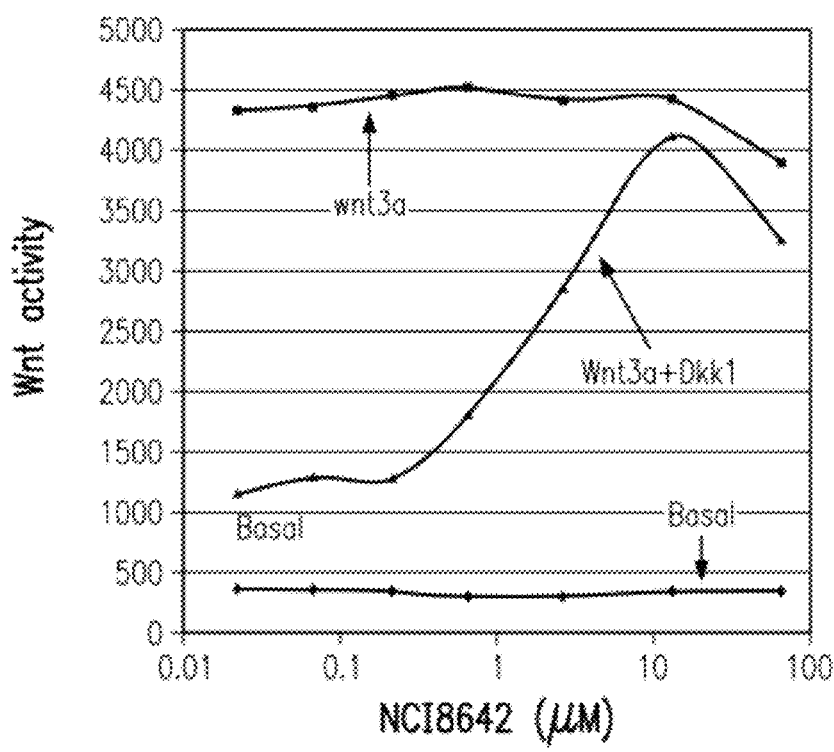
Figure 12A:
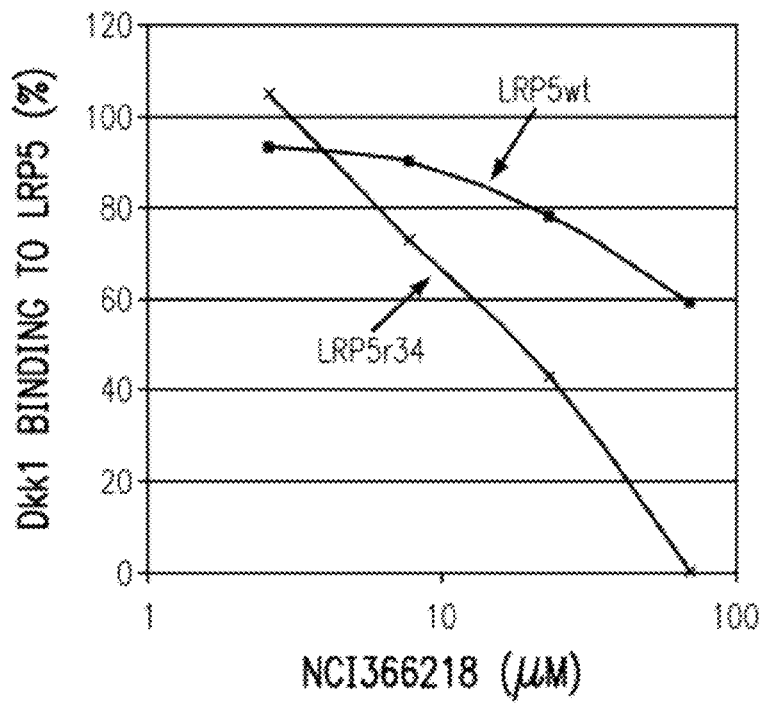
FIG. 12 shows that NCI366218 and NCI8642 can inhibit Dkk1 binding to LRP5. HEK cells were transfected with Mesd plasmids and LRP5 or LRP5R34. One day later, cells were treated with different concentrations of NCI366218 and NCI8642 and incubated on ice with conditioned medium (CM) prepared from HEK cells expressing mDkk1-AP. The AP activity was determined as previously described. The AP activity from cells treated with DMSO was taken as 100%.
Figure 12B:
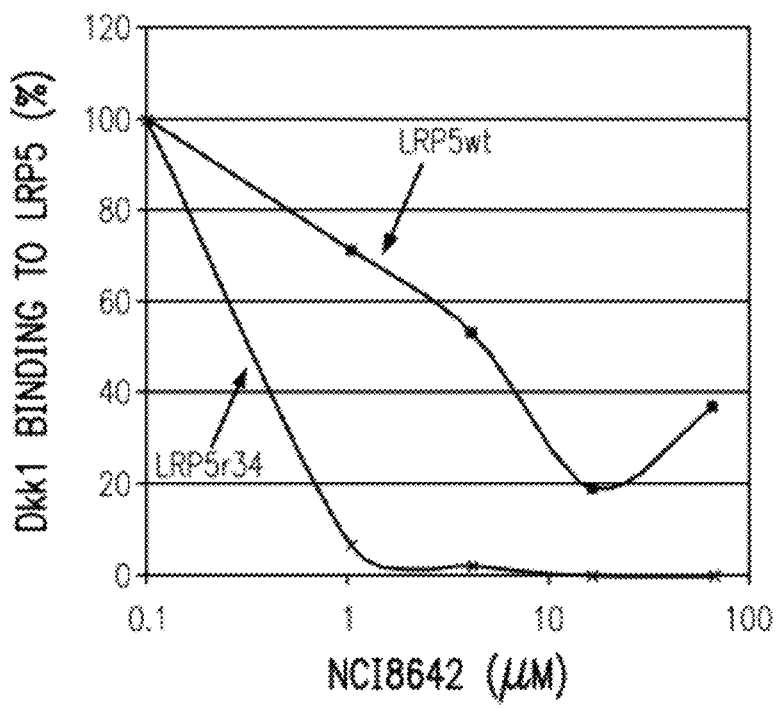

Both NCI8642 and NCI366218 were further characterized by Wnt activity assays and Dkk binding assays, as shown in FIG. 11 and FIG. 12. NCI8642 was more effective in the reversal of Dick-mediated inhibition. NCI8642 also had wider range of effective concentrations than NCI366218. Both compounds began to show Wnt inhibition at high concentrations. Both compounds reversed Dkk-mediated inhibition by disrupting the interaction between Dkk1 and LRP5 since both compounds inhibited the binding of Dkk1-AP to full length LRP5 and the LRP5 R34 mutant that lacks the first two domains. NCI8642 was shown to be more effective than NCI366218 in the inhibition of Dkk1 binding, consistent with its increased effectiveness in the reversal of Dkk-mediated antagonism to Wnt signaling.

Osteogenic Assay

Figure 13:
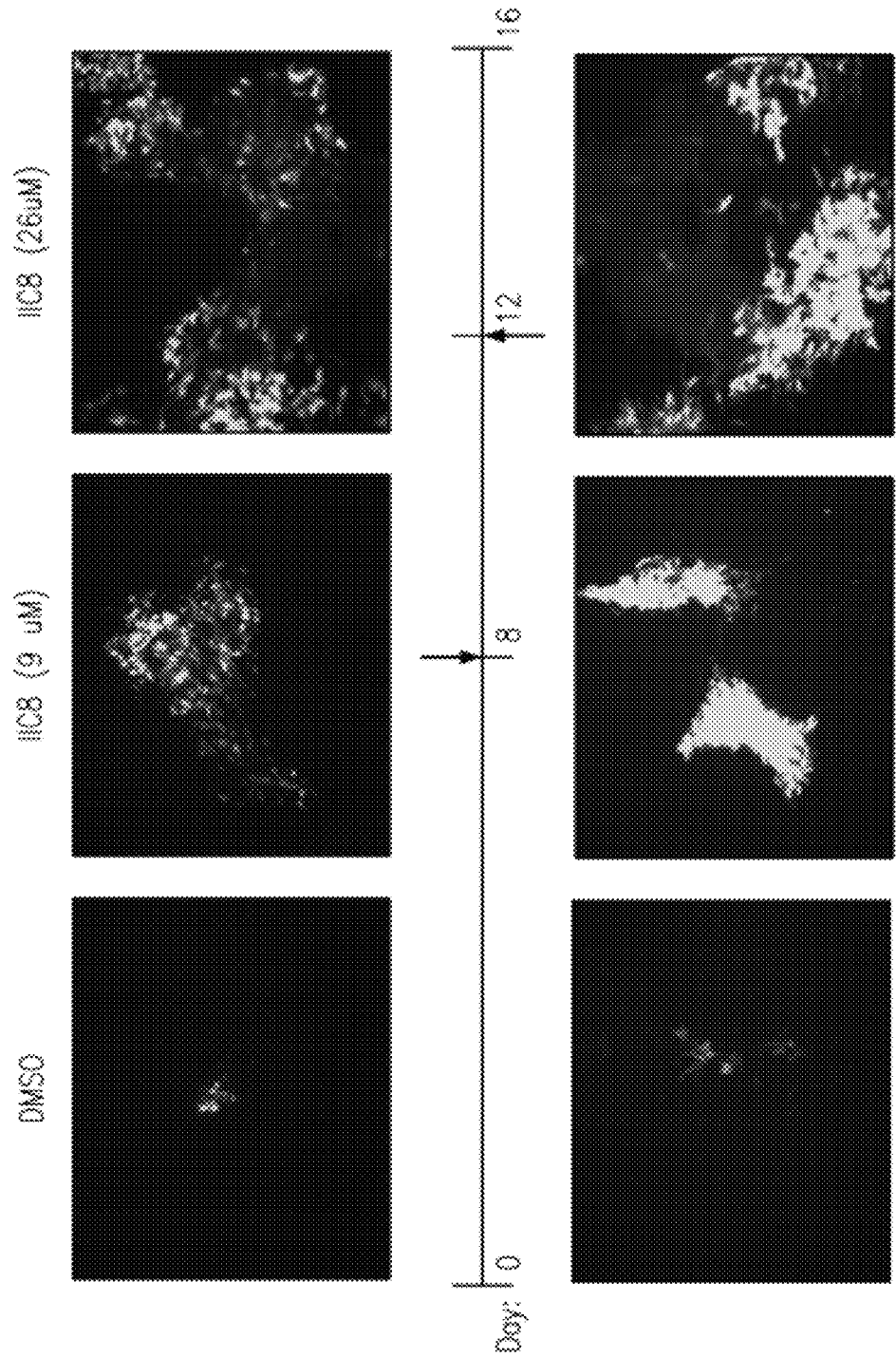
FIG. 13 illustrates that NCI366218 (IIC8) can stimulate osteoblast differentiation. Bone marrow stromal (BMS) cells were isolated from 3-month-old mice carrying a Green Fluorescent Protein (GFP) transgene controlled by the 2.3 Kb CollA1 promoter (2.3Col-GFP)[11], in which GFP can be used as a marker of osteoblast cells. On the $8^{th}$ and $12^{th}$ day, cultures were treated with 9 μM and 26 μM of IIC8 compound, respectively. The same time point, cultures were treated with DMSO as the control.
Figure 14:
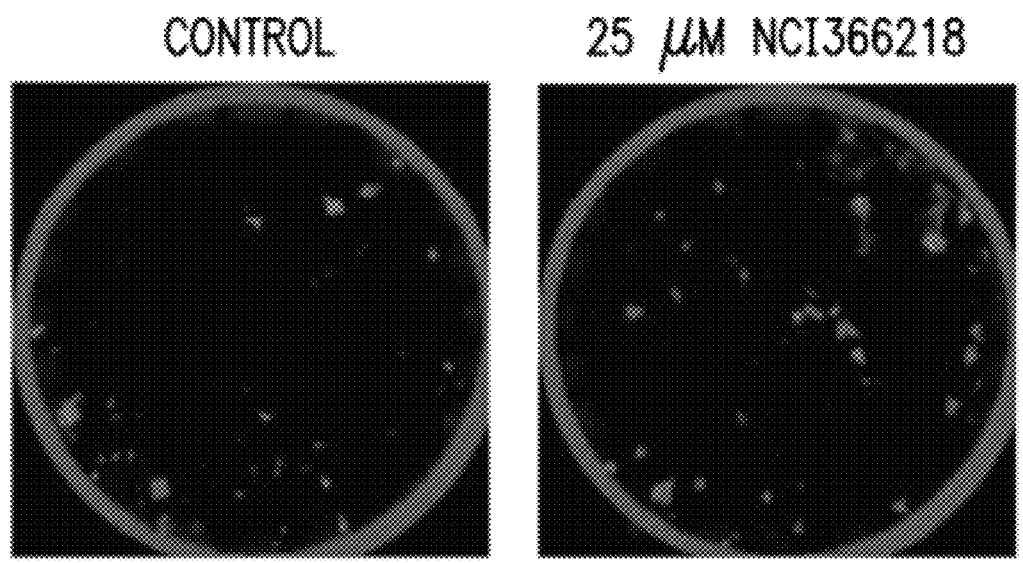
FIG. 14 shows an osteogenic assay. Primary bone marrow stromal osteoblasts were cultured in the presence and absence of NCI366218 and induced into differentiation. 20 days later, mineralization of the osteoblasts reflecting the bone formation process was observed with Xylene Orange staining. NCI366218 stimulated mineralization two fold.
Figure 14:
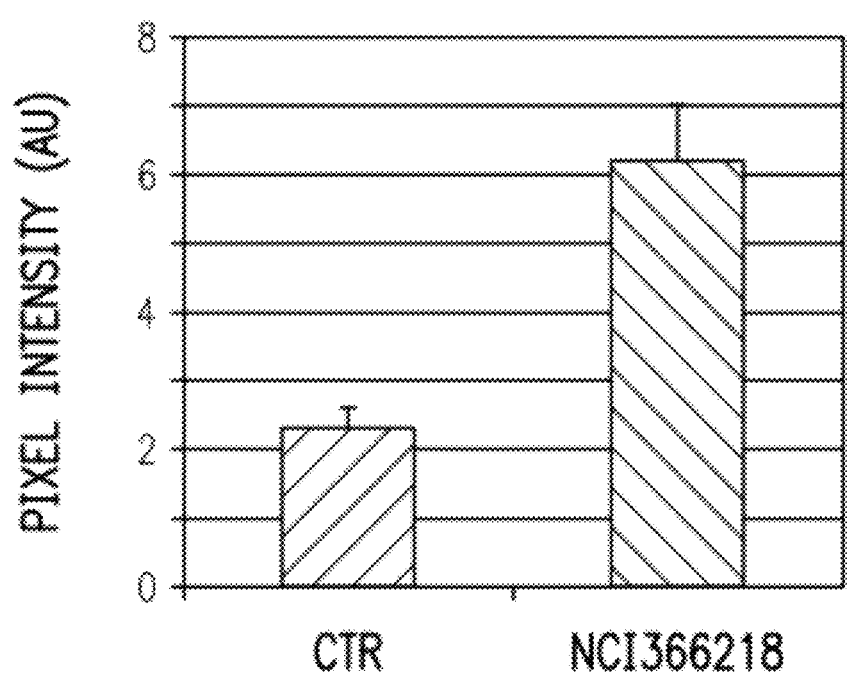
Figure 15A:
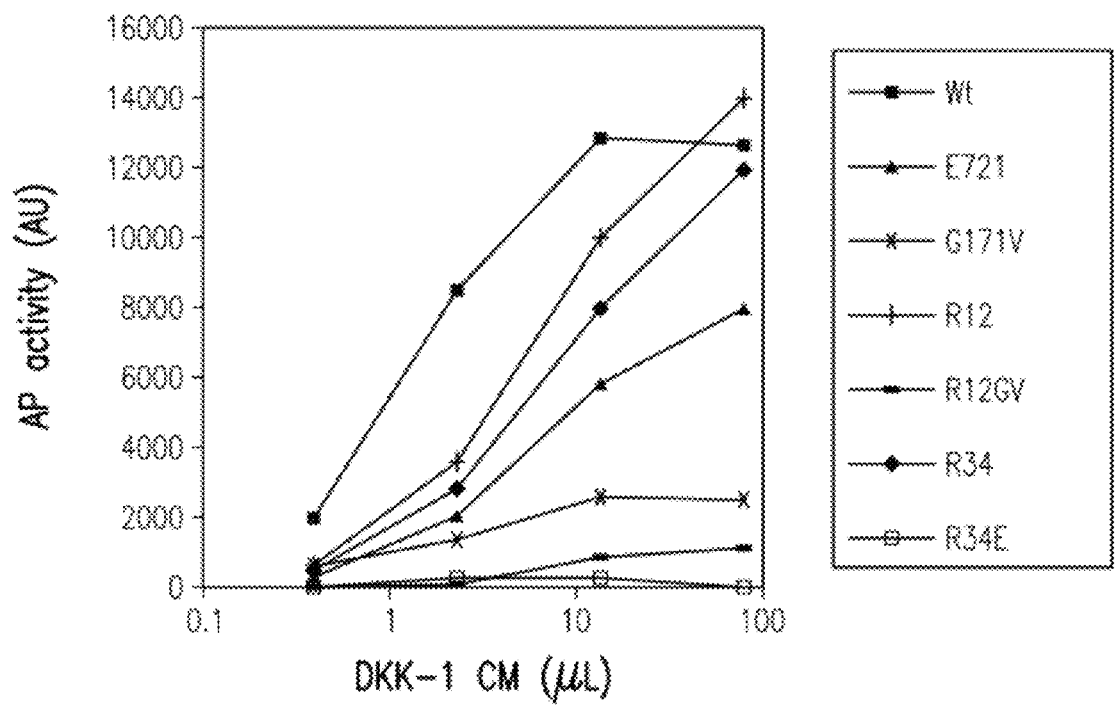
FIG. 15A shows that Dkk1 can bind to both LRP5R12 and LRP5R34, but the Dkk1 binding to the cell surface was significantly low in cells transfected with R12GV (G171V mutation in LRP5R12) and R34E (LRP5R34 carrying the E721 mutation).
Figure 15B:
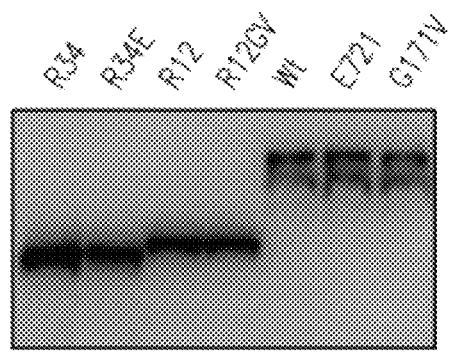
FIG. 15B shows equal amounts of Wt and mutant LRP5 expression after transfection.
Figure 16A:
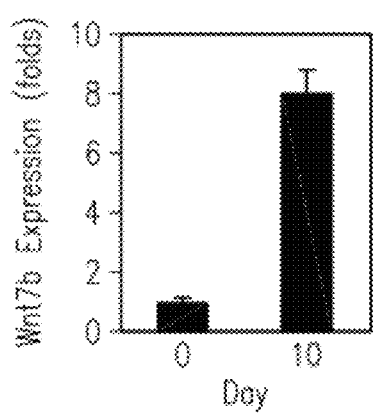
FIG. 16 illustrates Dkk1 and Wnt7b expression in osteogenic cells. Total RNA was isolated from bone marrow stromal cell culture at different time points after differentiation induction. Dkk and Wnt expression level was determined by real time RT-PCR. Wnt7b showed marked increase in its expression after differentiation induction (FIG. 16A). The ability of Wnt 7b to stimulate the LEF-1 reporter gene was examined and it was able to stimulate the canonical Wnt pathway (FIG. 16B).
FIG. 16C is mouse long bone section in situ hybridization picture. It shows most of Dkk1 is expressed in osteocyte. FIG. D illustrates the interactions between Kremen, Dkk, LRP, Wnt and Fz.
Figure 16B:
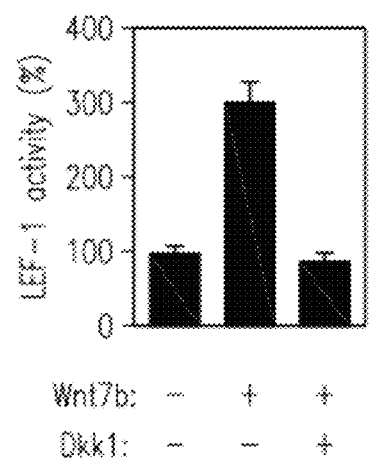
Figure 16C:
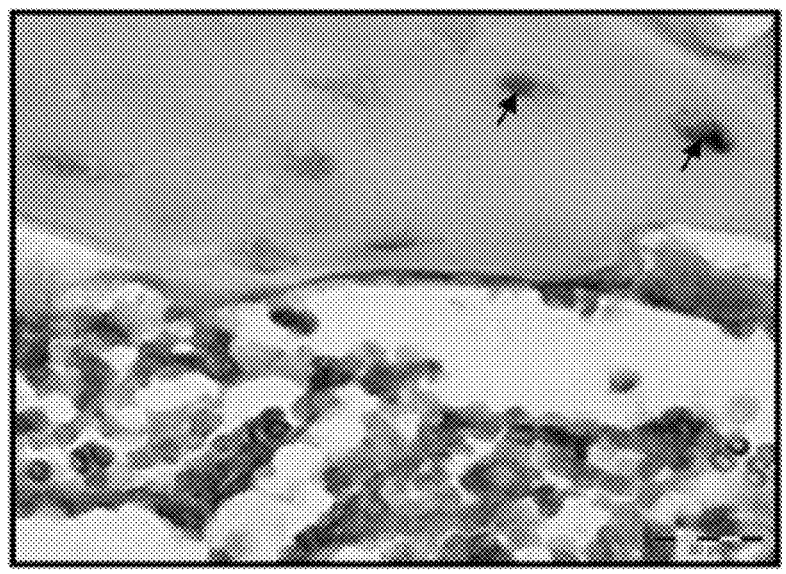
Figure 16D:
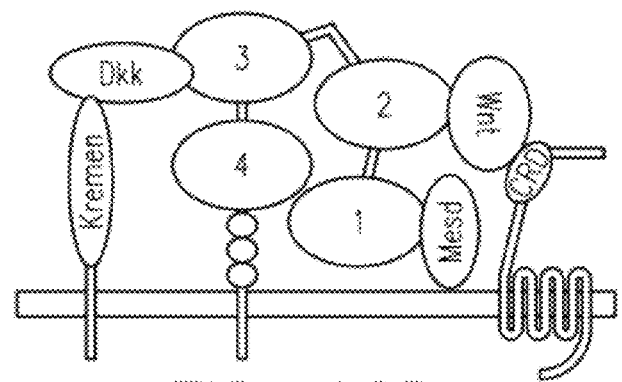

Wnt stimulates the proliferation and differentiation of cultured osteoblasts and Dkk inhibits this process. Therefore, these compounds increase osteogenesis. This may be monitored by the examination of mineralization or the expression of osteogeneic markers, including the expression of BSP, osteocalcin, and collagen. The expression of GFP driven by the 2.3 Kb Col1A1 promoter has also been monitored. FIG. 13 shows that NCI366218 stimulates GFP expression suggesting an increase in osteoblast differentiation. FIG. 14 shows that NCI366218 stimulates mineralization. NCI366218 also stimulates bone formation in calvarial organ culture.

Example 5.1 (B)

Screening Compounds Using Domain III as a Template

Figure 17A:
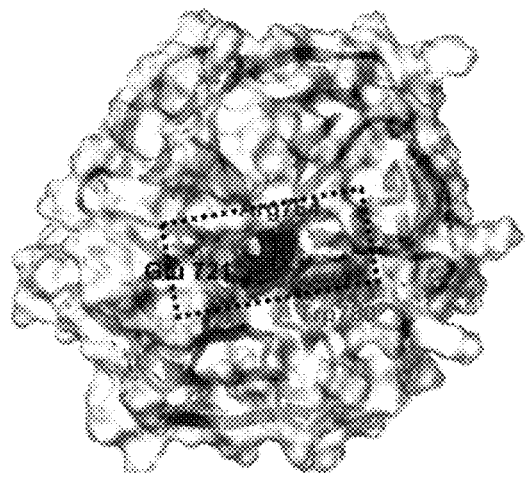
FIG. 17A shows the three key residues that were used in our initial shape-based virtual screen. The yellow box denotes the cavity.

Additional virtual screens of the National Cancer Institute (NCI) database (http://129.43.27.140/ncidb2) were carried out for chemical compounds that could potentially bind to this cavity. This database includes the coordinates of 250,251 small (M.W.<1,000 Da) chemical compounds. The initial screen was carried out with the program UNITY (Tripos, Inc.) using a search query consisting of LRP5 residues Glu721 and Arg764 with 0.3 Å tolerance and a hydrophobic center with 1.0 Å tolerance that is 3.2 Å away from LRP5 residue Trp780 (69) pointing towards the cavity (FIG. 17A). In order to take the flexibility of the compounds into consideration, the Directed Tweak algorithm in the program UNITY, which allows a rapid and conformationally flexible 3D search (21), was applied.

The candidate compounds (~2000) from the UNITY screen were then docked into the DKK1-binding surface using the program FlexX (Tripos, Inc.), which can quickly and flexibly dock ligands to protein-binding sites (72, 73). LRP5 residues Glu721, Trp863, Tyr719, Arg764, Asp887, Phe888, Gly781, Trp780 and Met890, which have been shown to be involved in DKK1 binding (69), were included in the calculations. Following the docking procedures, the compounds were ranked based on their predicted binding affinities for the Dkk1-binding pocket using the program Cscore. Cscore generates a relative, consensus score based on how well the individual scoring functions of the protein-ligand complex perform. The results from Cscore were then subjected to a final visual inspection.

Figure 17B:
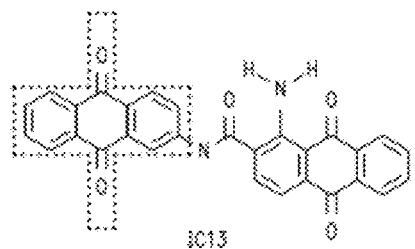
FIGS. 17B-G shows the chemical structures of IC13 (B), IC15 (C), IIC8 (D), IIC15 (E), IIC24 (F) and IIIC3 (G). The anthra-9,10-quinone core is boxed.

Seventeen compounds with the highest consensus scores were further tested (Compound IC1-IC17, Table IV). These compounds were subjected to the Dkk-1-binding competition and Wnt activity assays. Specifically, NIH3T3 cells were transfected with Wnt activity luciferase reporter gene. Next day, compounds, which were dissolved in DMSO at 2 mg/ml and diluted into PBS at 20 ug/ml, were added into tissue culture medium (basal), medium containing Wnt3a (Wnt) or both Wnt3a and Dkk1 (Wnt+Dkk). Control contains the same amount of DMSO. Six hours late cells were lysed and Wnt activity was determined by luciferase assay. Ten compounds showed more than 50% inhibition of Wnt-stimulated reporter gene activity without significantly affecting the basal reporter gene activity (Table IV). Among these ten compounds, four affected the binding of Dkk-alkaline phosphatase (AP) to LRP5 expressed on cell surface; IC14 and IC15 showed more than thirty percent inhibition, whereas, surprisingly, IC5 and IC13 showed stimulation of the binding (Table IV). The inhibition of Wnt activity may be due to the binding of the compounds to the first two YWTD repeat domains that have been implicated in Wnt binding probably through a direct interaction with Wnt molecules (35, 36, 47). Importantly, IC5, IC13 (FIG. 17B), and IC15 (FIG. 17C) all contain an anthra-9,10-quinone core structure, suggesting that the quinone structure may provide basic interacting forces for the molecules to interact with the cavity. The presence of several aromatic amino acid residues in the Dkk-interacting cavity supports this idea.

TABLE IV

| | | | | | | |
|---|---|---|---|---|---|---|
| | | | First round screen summary | | | |
| | | | Lef activity % | | Binding | |
| Compound | Designate | Basal | Wnt3aCM | Wnt3aCM DkklCM | to LRP5 | Structure |
| Control | Ctr | 100 | 1627 | 290 | 100 | |
| 270071 | IC1 | 104 | 841 | 314 | 97 | 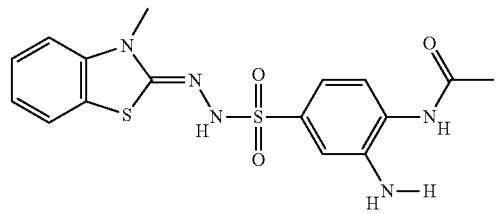 |
| 45123 | IC2 | 106 | 1092 | 318 | 117 | 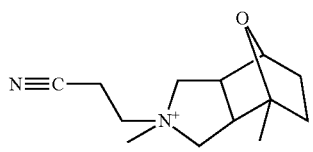 [SMILES: CC12CCC(O1)C1C[N+](C)(CCC#N)CC12] |

TABLE IV-continued
First round screen summary
| Compound | Designate | Lef activity % | | | Binding to LRP5 | Structure |
| --- | --- | --- | --- | --- | --- | --- |
| | | Basal | Wnt3aCM | Wnt3aCM Dkk1CM | | |
| 37815 | IC3 | 47 | 55 | 49 | 85 | 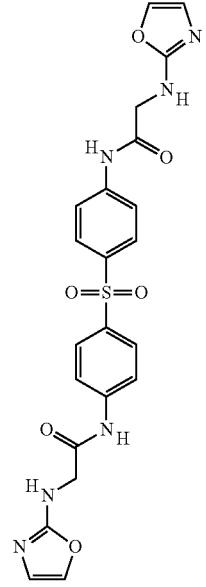 |
| 382917 | IC4 | 104 | 452 | 162 | 108 | 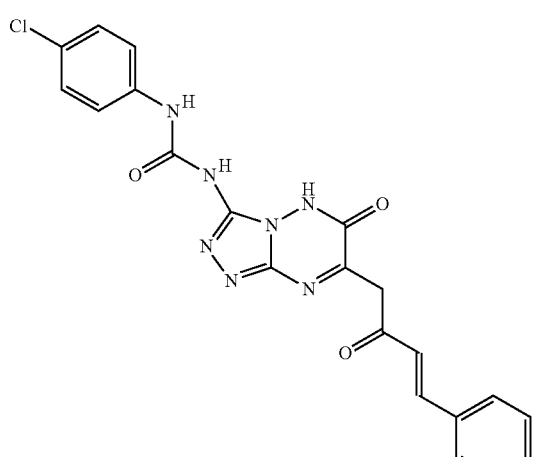 |

TABLE IV-continued
First round screen summary
| Compound | Designate | Lef activity % | | | Binding to LRP5 | Structure |
| --- | --- | --- | --- | --- | --- | --- |
| | | Basal | Wnt3aCM | Wnt3aCM Dkk1CM | | |
| 660224 | IC5 | 84 | 131 | 142 | 276 | 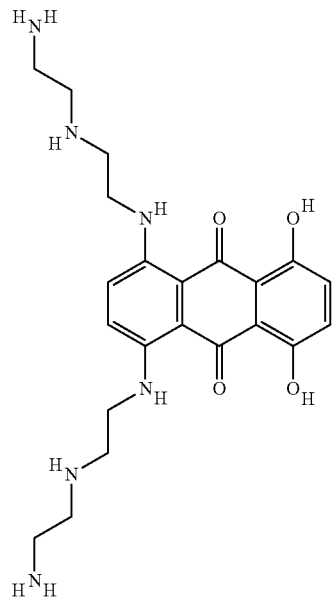 |
| 38290 | IC6 | 114 | 990 | 323 | 101 | 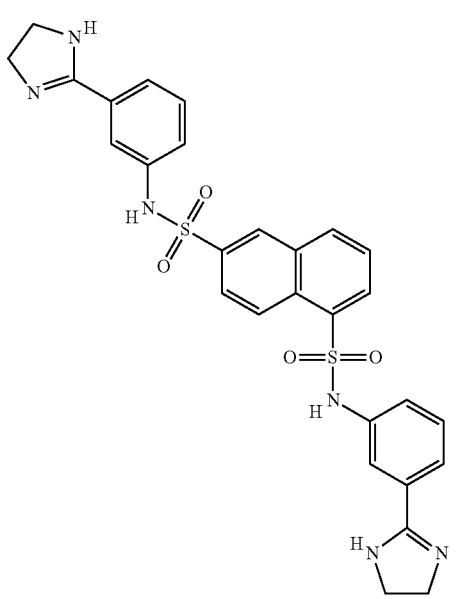 |

TABLE IV-continued
First round screen summary
| Compound | Designate | Lef activity % | | | Binding to LRP5 | Structure |
| --- | --- | --- | --- | --- | --- | --- |
| | | Basal | Wnt3aCM | Wnt3aCM Dkk1CM | | |
| 649827 | IC7 | 105 | 1072 | 370 | 88 | 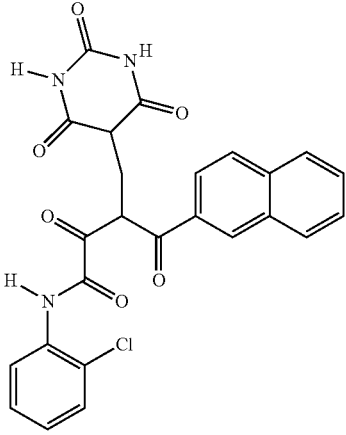 |
| 70694 | IC8 | 107 | 623 | 231 | 120 | 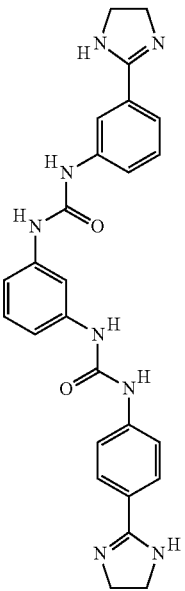 |
| 648597 | IC9 | 95 | 268 | 147 | 79 | 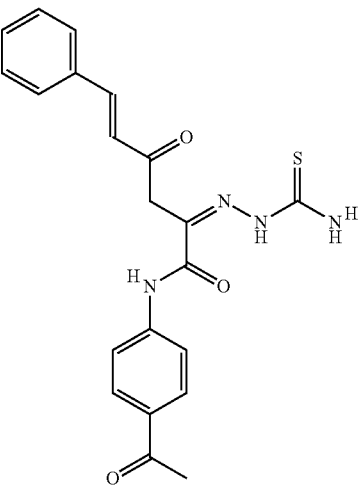 |

TABLE IV-continued

First round screen summary

| Compound | Designate | Lef activity % | | | Binding to LRP5 | Structure |
| | | Basal | Wnt3aCM | Wnt3aCM Dkk1CM | | |
|---|---|---|---|---|---|---|
| 618567 | IC10 | 102 | 962 | 324 | 96 | |
| 657726 | IC11 | 109 | 239 | 217 | 90 | |
| 12156 | IC12 | 112 | 762 | 239 | 127 | |
| 39914 | IC13 | 113 | 147 | 143 | 654 | |

TABLE IV-continued

First round screen summary

| Compound | Designate | Lef activity % | | | Binding to LRP5 | Structure |
| --- | --- | --- | --- | --- | --- | --- |
| | | Basal | Wnt3aCM | Wnt3aCM Dkk1CM | | |
| 106164 | IC14 | 97 | 340 | 217 | 68 | 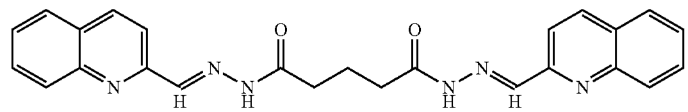 |
| 16221 | IC15 | 133 | 115 | 106 | 63 | 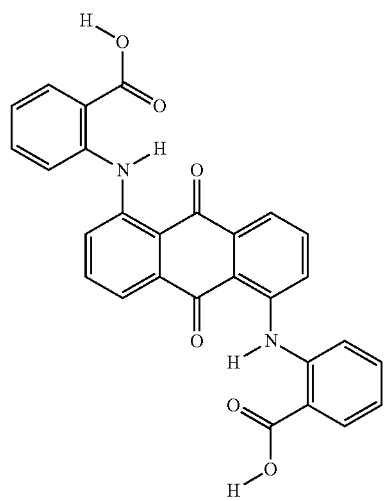 [SMILES: O=C(O)c1ccccc1Nc1cccc2c1C(=O)c1cccc(Nc3ccccc3C(=O)O)c1C2=O] |
| 651656 | IC16 | 99 | 398 | 226 | 96 | 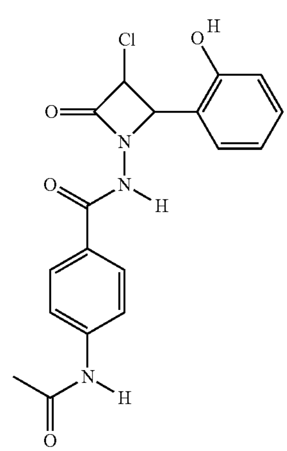 |

TABLE IV-continued

First round screen summary

| Compound | Designate | Basal | Lef activity % Wnt3aCM | Wnt3aCM Dkk1CM | Binding to LRP5 | Structure |
|---|---|---|---|---|---|---|
| 67653 | IC17 | 103 | 1124 | 369 | 107 | |
| Control | Ctr | 100 | 1890 | 193 | | |
| 127133 | IIC1 | 97 | 397 | 197 | 106 | |
| 1743 | IIC2 | 104 | 1420 | 417 | 81 | |

TABLE IV-continued

First round screen summary

| Compound | Designate | Lef activity % | | | Binding to LRP5 | Structure |
| | | Basal | Wnt3aCM | Wnt3aCM Dkk1CM | | |
| --- | --- | --- | --- | --- | --- | --- |
| 337836 | IIC4 | 116 | 1381 | 197 | 133 | |
| 37608 | IIC5 | 21 | 39 | 29 | 63 | |
| 372294 | IIC6 | 103 | 105 | 118 | 429 | |

TABLE IV-continued

First round screen summary

| Compound | Designate | Lef activity % | | | Binding to LRP5 | Structure |
| --- | --- | --- | --- | --- | --- | --- |
| | | Basal | Wnt3aCM | Wnt3aCM Dkk1CM | | |
| 123823 | IIC7 | 79 | 394 | 217 | 122 | |
| 342051 | IIC9 | 115 | 178 | 239 | 53 | |
| 116405 | IIC12 | 88 | 429 | 110 | 100 | |

TABLE IV-continued

First round screen summary

| Compound | Designate | Lef activity % | | | Binding to LRP5 | Structure |
| | | Basal | Wnt3aCM | Wnt3aCM Dkk1CM | | |
|---|---|---|---|---|---|---|
| 373532 | IIC14 | 99 | 254 | 138 | 163 | |
| 25869 | IIC15 | 105 | 1683 | 369 | 85 | |
| 310659 | IIC16 | 128 | 364 | 147 | 57 | |
| 28561 | IIC17 | 90 | 1323 | 231 | 323 | |

TABLE IV-continued

First round screen summary

| Compound | Designate | Lef activity % | | | Binding to LRP5 | Structure |
| --- | --- | --- | --- | --- | --- | --- |
| | | Basal | Wnt3aCM | Wnt3aCM Dkk1CM | | |
| 209942 | IIC20 | 101 | 1565 | 276 | 805 | 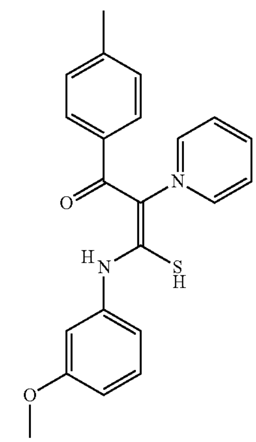 |
| 366105 | IIC21 | 107 | 288 | 103 | 54 | 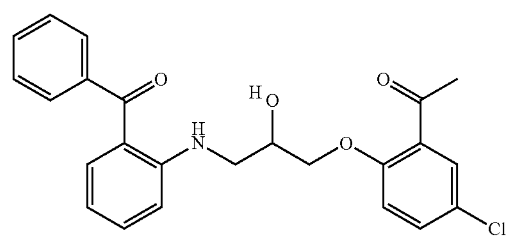 |
| 159858 | IIC22 | 121 | 269 | 311 | 118 | 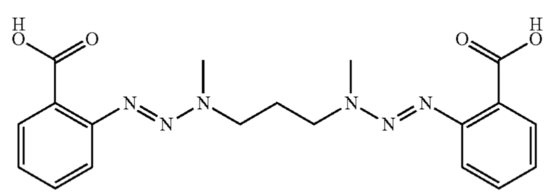 [SMILES: CN(CCCN(C)/N=N/c1ccccc1C(=O)O)/N=N/c1ccccc1C(=O)O] |
| 647082 | IIC23 | 95 | 1620 | 302 | 97 | 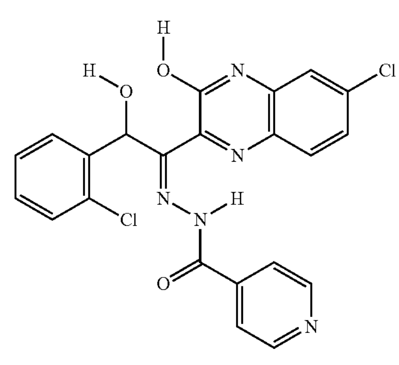 [SMILES: O=C(N/N=C(\c1nc2ccc(Cl)cc2nc1O)C(O)c1ccccc1Cl)c1ccncc1] |

TABLE IV-continued
First round screen summary
| Compound | Designate | Lef activity % | | | Binding to LRP5 | Structure |
| | | Basal | Wnt3aCM | Wnt3aCM Dkk1CM | | |
|---|---|---|---|---|---|---|
| 657566 | IIC24 | 105 | 1957 | 552 | 68 | 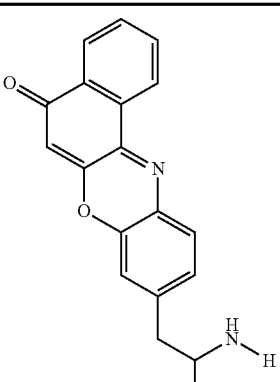 |
TABLE V
Summary for screening based on the anthra-9,10-quninone core structure
| Compound | Designate | Lef activity % | | | Structure |
| | | Basal | Wnt3aCM | Wnt3aCM Dkk1CM | |
|---|---|---|---|---|---|
| DMSO | Ctr | 100 | 1890 | 193 | |
| 39963 | IIC3 | 115 | 1536 | 229 | |

TABLE V-continued

Summary for screening based on the anthra-9,10-quninone core structure

| | | Lef activity % | | | |
|---|---|---|---|---|---|
| Compound | Designate | Basal | Wnt3aCM | Wnt3aCM Dkk1CM | Structure |
| 366218 | IIC8 | 109 | 2392 | 713 | |
| 39957 | IIC10 | 103 | 161 | 120 | |
| 4997 | IIC11 | 111 | 1782 | 223 | |
| 641424 | IIC13 | 111 | 443 | 128 | |

TABLE V-continued

Summary for screening based on the anthra-9,10-quninone core structure

| | | Lef activity % | | | |
|---|---|---|---|---|---|
| Compound | Designate | Basal | Wnt3aCM | Wnt3aCM Dkk1CM | Structure |
| 51530 | IIC18 | 129 | 119 | 127 | |
| 128436 | IIC19 | 166 | 144 | 148 | |

TABLE VI

Summary for screening based on IIC15

| | | Lef activity % | | | |
|---|---|---|---|---|---|
| Compound | Designate | Basal | Wnt3aCM | Wnt3aCM Dkk1CM | Structure |
| DMSO | 20 µg/ml | 100 | 1070 | 339 | |
| 37089 | IIIC1 | 102 | 1160 | 362 | |

TABLE VI-continued
Summary for screening based on IIC15
| | | | Lef activity % | | |
|---|---|---|---|---|---|
| Compound | Designate | Basal | Wnt3aCM | Wnt3aCM Dkk1CM | Structure |
| 97309 | IIIC2 | 90 | 503 | 193 | 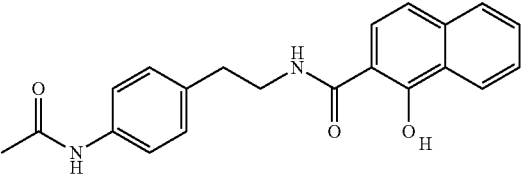 |
| 66425 | IIIC4 | 85 | 1071 | 358 | 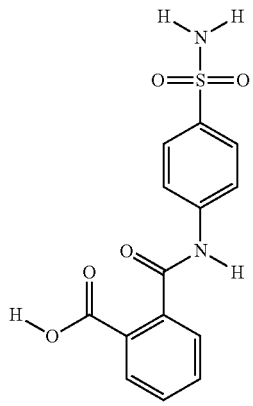 [SMILES: NS(=O)(=O)c1ccc(NC(=O)c2ccccc2C(=O)O)cc1] |
| 113914 | IIIC5 | 95 | 1238 | 463 | 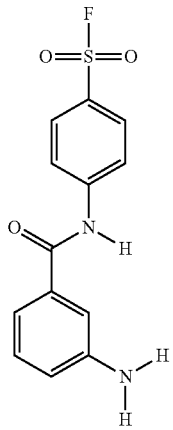 [SMILES: Nc1cccc(C(=O)Nc2ccc(S(=O)(=O)F)cc2)c1] |
| 115934 | IIIC7 | 88 | 865 | 276 | 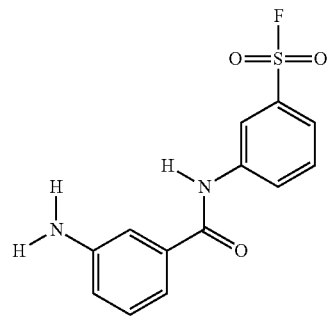 [SMILES: Nc1cccc(C(=O)Nc2cccc(S(=O)(=O)F)c2)c1] |

TABLE VI-continued

Summary for screening based on IIC15

| | | Lef activity % | | | |
|---|---|---|---|---|---|
| Compound | Designate | Basal | Wnt3aCM | Wnt3aCM Dkk1CM | Structure |
| 110317 | IIIC8 | 90 | 1505 | 426 | |
| 3751 | IIIC9 | 97 | 1491 | 477 | |
| 28627 | IIIC10 | 107 | 1133 | 613 | |

TABLE VI-continued

Summary for screening based on IIC15

| Compound | Designate | Lef activity % | | | Structure |
|---|---|---|---|---|---|
| | | Basal | Wnt3aCM | Wnt3aCM Dkk1CM | |
| 10573 | IIIC11 | 87 | 999 | 404 | |
| 37179 | IIIC13 | 92 | 1323 | 391 | |

TABLE VII

Summary for screening based on IIC24

| Compound | Designate | Lef activity % | | | Structure |
|---|---|---|---|---|---|
| | | Basal | Wnt3aCM | Wnt3aCM Dkk1CM | |
| DMSO | 20 μg/ml | 100 | 1070 | 339 | |
| 8642 | IIIC3 | 101 | 1282 | 1111 | |

TABLE VII-continued

Summary for screening based on IIC24

| Compound | Designate | Lef activity % | | | Structure |
|---|---|---|---|---|---|
| | | Basal | Wnt3aCM | Wnt3aCM Dkk1CM | |
| 364163 | IIIC6 | 63 | 53 | 42 | |
| 620055 | IIIC12 | 10 | 12 | 15 | |

IIC8 and IIIC3 are in blue. Color legends are the same as in Supplementary Table I.

With the assumption that the quinone core structure may contribute to the interaction, we conducted a second round of virtual screening and a 2D search, for the compounds that are similar to anthra-9,10-quinone in the NCI database using the similarity search algorithm of the UNITY program. The hits were then docked with FlexX as described previously. Seven highly scored compounds were then obtained from NCI and tested in the biological assays. Compound IIC8 (FIG. 17D) was identified for its ability to reverse Dkk-mediated inhibition of Wnt signaling (Table V).

In addition to the anthra-9,10-quinone-based compounds, an additional 17 compounds that ranked from 41-80 in their Cscores from the first virtual screen was obtained. The test of these 17 compounds revealed that nine of them inhibited Wnt signaling more than 50% (shaded compounds in Table IV). Importantly, four of compounds from this screen, including IIC15 (FIG. 17E) and IIC24 (FIG. 17F), showed some ability to reverse Dkk-mediated inhibition of Wnt signaling without significantly inhibiting Wnt signaling itself (Table IV). A 2D similarity search was carried out using IIC15 and IIC24 as the templates, and 13 additional candidate compounds were obtained for the Wnt activity assay (Tables VI and VII). One of the IIC24-based compounds, IIIC3 (FIG. 17G), turned out to be a very potent antagonist of Dkk-mediated inhibition of Wnt signaling (Table VII).

Figure 18A:
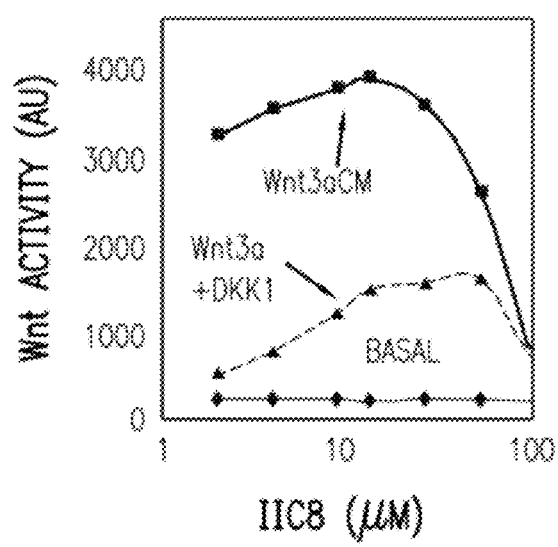
FIG. 18 shows effects of compounds on Wnt activity and Dkk-binding.
Figure 18B:
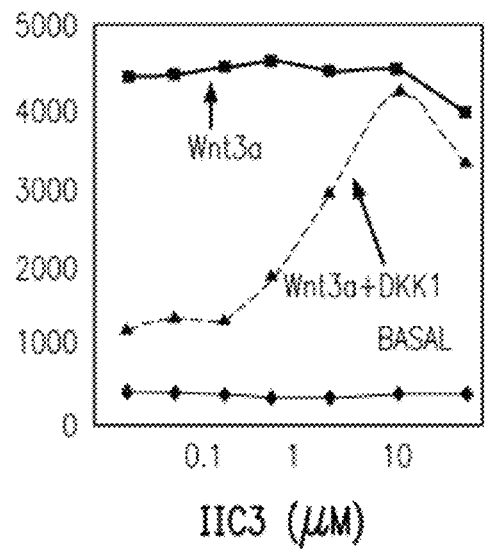
Figure 18C:
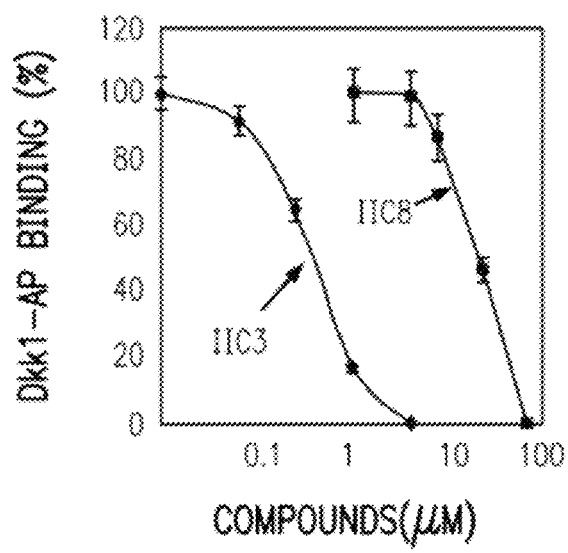
Figure 18D:
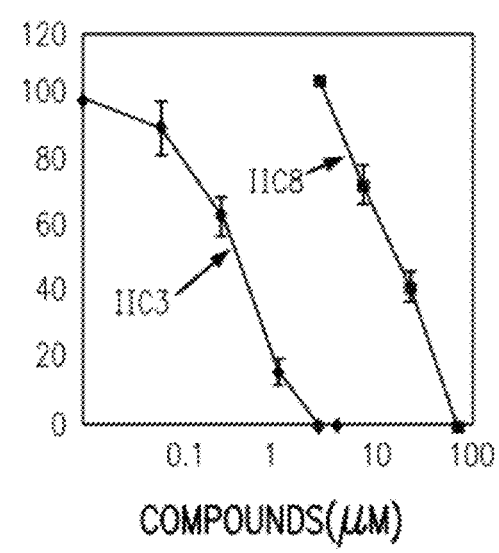

Both IIC8 and IIIC3 compounds were characterized further in the Wnt activity and Dkk binding assays. IIIC3 is more effective in reversal of Dkk inhibition and has a wider range of effective concentrations than IIC8 (FIG. 18A, B). IIC8 started to reverse Dkk-mediated inhibition at micro molar concentrations with an approximate $EC_{50}$ of 10 μM, whereas IIIC3 started to reverse Dkk inhibition below 1 μM with an EC50 of about 2 μM. Both compounds appeared to inhibit Wnt signaling at high concentrations. This inhibitory effect may be due to the low affinity of the compounds for the first two YWTD repeat domains that are required for Wnt signaling. Because both compounds inhibited the binding of Dkk1-AP to wild-type LRP5 (FIG. 18C) and a LRP5 mutant (FIG. 18D) that lacks the first two YWTD repeat domains, but retaining the Dkk binding domain (69), it is reasonable to conclude that these compounds are most likely to reverse Dkk inhibition by disrupting the interaction between Dkk1 and LRP. In addition, IIIC3 is more effective than IIC8 in the inhibition of Dkk1 binding, which is consistent with its increased effectiveness in its reversal of Dkk-mediated antagonism to Wnt signaling. Furthermore, the $IC_{50}$ values of these compounds (about 1 μM for IIIC3 and 10 μM for IIC8) for blocking the binding of Dkk1 to LRP5 are similar to the $EC_{50}$ values for these compounds to reverse Dkk inhibition, further supporting the conclusion that these compounds reverse Dkk inhibition by disrupting the interaction between Dkk and LRP.

Figure 17C:
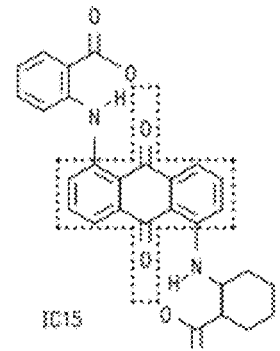
Figure 17D:
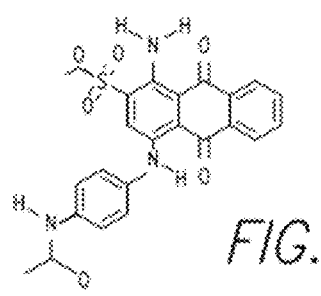
Figure 17E:
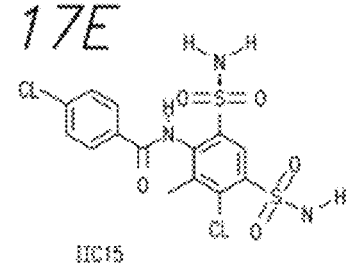
Figure 17F:
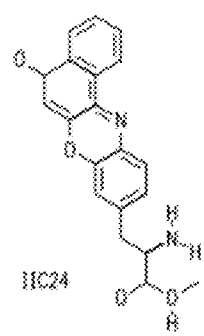
Figure 17G:
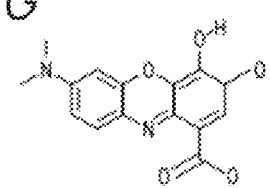
Figure 19A:
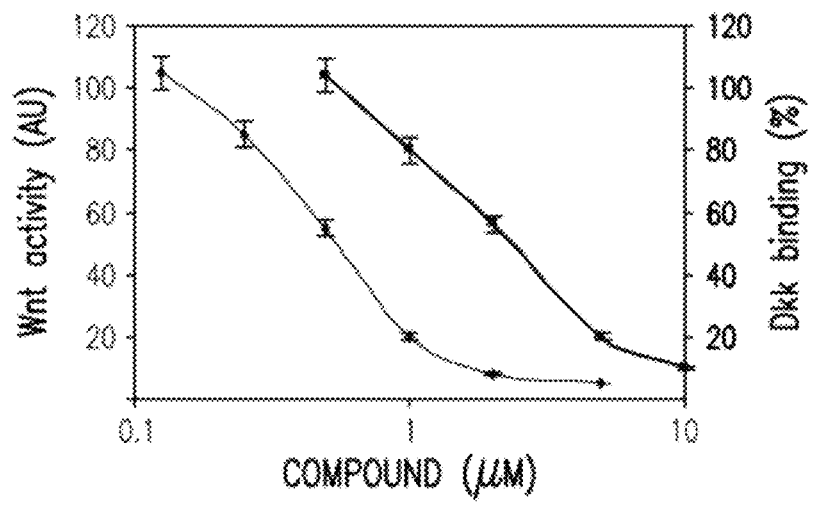
FIG. 19A shows effects of IC15 on Wnt3a-stimulated Wnt reporter gene activity and Dkk1-AP binding to LRP5.
Figure 19B:
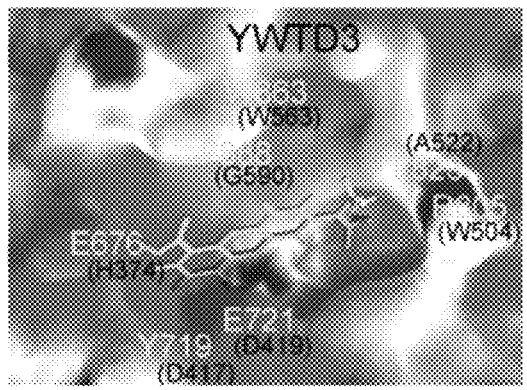
FIGS. 19B-E show molecular modeling of the binding of IIIC3 and IC 15 to the second and third YWTD repeat domains of LRP5. Corresponding residues are in parentheses.
Figure 19D:
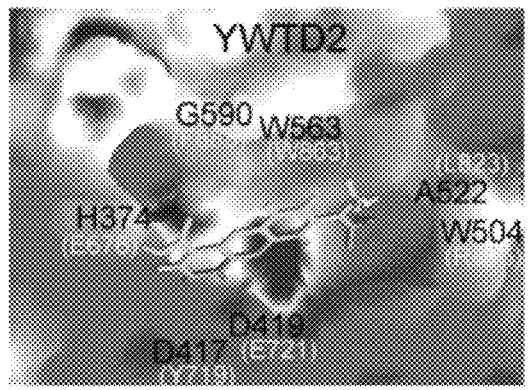
Figure 19C:
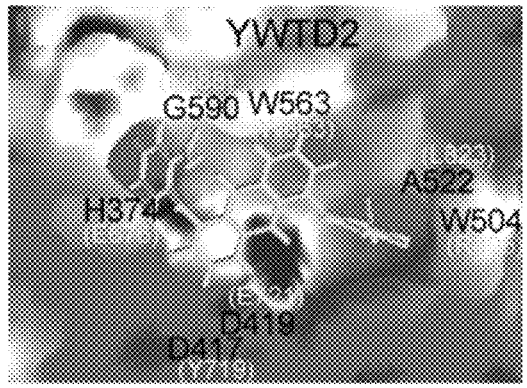
Figure 19E:
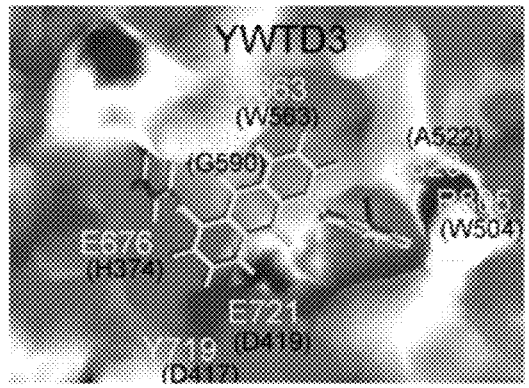
Figure 20A:
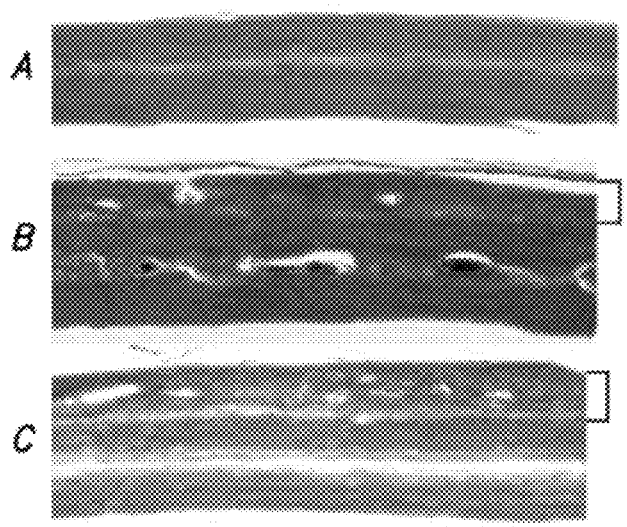
FIGS. 20A and 20B show effects on calvarial bone formation. Control vehicle (a), b-FGF (b), or IIIC3 (c) was injected under the skull derma three times a day for five days. Two weeks after the final injection, calvarias were collected, fixed, decalcified, and sectioned. The new bone layers are marked. The thickness of the new bone layers was quantified and is shown in B.
Figure 20B:
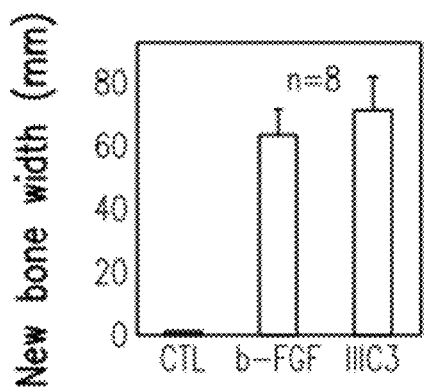
Figure 20C:
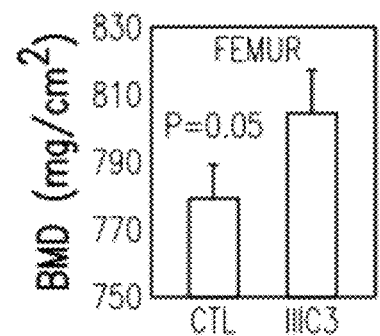
FIGS. 20C-E shows effects on bone mineral density (BMD). BMD and body weight were determined after the mice (n=20) were subjected to treatment and rest regiments.
Figure 20D:
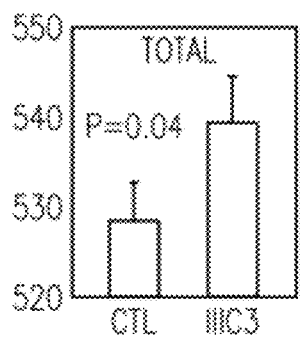
Figure 20E:
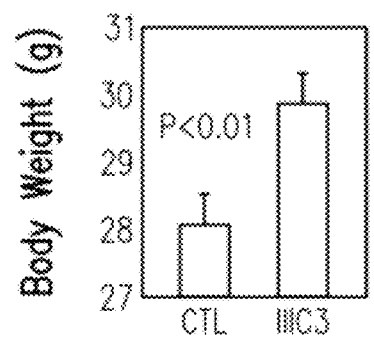
Figure 29:
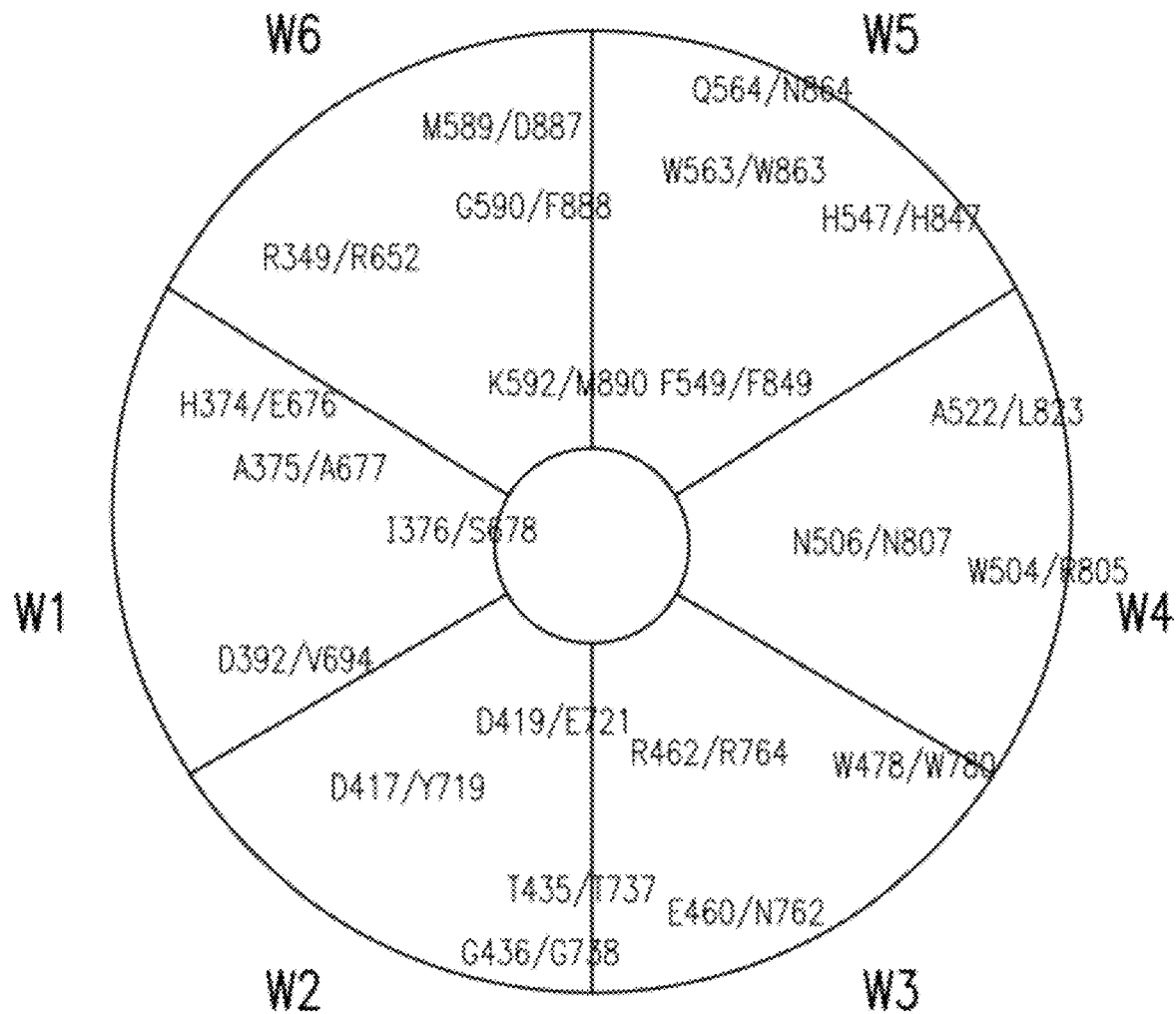
FIG. 29 shows a comparison of amino acids at the binding sites at the second (red) and third (blue) domains. Common amino acids are in black.

To better understand the function and structure relationship of the compounds, Wnt inhibiting compounds were reexamined. Among the 54 compounds we tested, almost a half (74) of them showed more than 50% inhibition of Wnt3a at 20 µg/ml (Tables IV-VII). The most potent Wnt inhibitor is IC15 (FIG. 17C). IC15 has an $IC_{50}$ value of about 0.5 µM for inhibiting the Wnt3a activity (FIG. 19A). This value is about 10 fold lower than the $IC_{50}$ value (5 µM) for inhibiting Dkk binding to the third YWTD EGF repeat domain, the domain that is required for Dkk antagonism (FIG. 19A). By contrast, the concentrations of IIIC3 required for inhibiting Wnt are at least ten times higher than those required for inhibiting Dkk binding, while the $IC_{50}$ values for IIIC3 to inhibit Dkk binding and to reverse Dkk-inhibition are similar (FIG. 18). These conclusions are further supported by the molecular modeling analysis of the binding of IIIC3 and IC15 to the second and third YWTD repeat domains. Although the second and third YWTD repeat domains of LRP5 share extensive amino acid sequence homology (41% identity), there are considerable differences in the ligand binding cavities of these two domains (FIG. 29). The cavity on the second domain is larger than that on the third domain, while the cavity of the third domain is deeper (FIG. 19 B, C). Therefore, it is reasonable to predict that IC15, which is larger than IIIC3, may fit better into the cavity of the second domain, whereas IIIC3 may match better with the cavity of the third domain. Indeed, in the FlexX docking models, the IIIC3 fits well into the cavity of the third domain (FIG. 3B), whereas IC15 fits perfectly with that of the second domain (FIG. 19C). In the IIIC3 complex structure, if the third domain is replaced with the second domain, the bound IIIC3 will lose many contacts with the target residues, that include Glu721, Tyr719, Leu823, and Phe888 (FIG. 19D). On the other hand, if the second domain is replaced with the third domain in the IC15 complex, the residues, for instance Leu823 and Phe888, on the third domain would clash with the bound IC15 (FIG. 19E).

It was next determined whether the most potent Dkk antagonistic compound IIIC3 could stimulate bone formation in mice. The compound was tested in a local bone formation model. IIIC3 was dissolved in DMSO and diluted 1:1000 into PBS at a concentration of 0.44 mg/ml. Fifteen micro-liters of IIIC3 (0.22 mg/Kg/day), control vehicle, or positive control (b-FGF, 12.5 µg/Kg/day) were injected into the subcutaneous tissue over the right side of the calvaria of four weeks old CD-1 mice three times a day for 5 days using a injection method described previously (74, 75). Calvarias were collected 22 days after the first injection and fixed for sectioning. As shown in FIG. 19, new bones were found in both b-FGF and IIIC3 treated calvarias. IIIC3 appeared to be as potent as FGF in stimulating bone formation (FIG. 19B). To evaluate the effectiveness of the compound in a systemic bone formation assay, we injected C57B1 mice (8 weeks old) intraperitoneally with IIIC3 and control vehicle. We observed significant increases in both femoral and whole body bone mineral density in mice injected with IIIC3 (2% increase for femur and 2.5% for total) compared to the control (FIG. 19 C, D), accompanying with a significant increase in body weight (7.1%; FIG. 19E). These results further validated the LRP/Dkk interaction as a potential therapeutic target for increasing bone formation and demonstrated these Dkk antagonists may be suitable lead compounds for further development into anabolic therapeutics to treat osteoporosis.

Protein-protein interactions are generally considered to be difficult to disrupt by small molecule compounds. In this study, a screening approach was used that combines structural biology, computation, and biological assays to identify small molecule compounds that can efficiently disrupt Dkk-LRP5 interaction. A de novo initial virtual screen was carried out for chemicals based only on a predicted structure of a target without any template. We were able to identify compounds from physical screening of merely 54 compounds, and the successive rounds of screening yielded better compounds than the previous did. In addition, the computation allows not only simply identifying compounds that fit into a cavity, but also provides a guide to compounds that can discriminate two similar cavities, i.e., the third YWTD repeat domain from the first two YWTD repeat domains of LRP5. The approach has allowed us to identify potent Dkk and Wnt antagonistic compounds that have shown great potentials to be developed into therapeutic reagents for treating osteoporosis and cancer. In addition, these compounds provide useful tools for therapeutic target validation and basic research in Wnt signaling.

Example 6

Use of IIIC3 as a Core Compound to Design New Variants

As described above, the ability of IIIC3 (NCI 8642) to act upon Wnt activity allows it to be used to design a core model where varying the R groups on this template allows identification of other molecules that may also have effects upon Wnt activity. Thus, if like IIIC3, $R^1$, $R^3$, $R^4$ and $R^6$ were hydrogens and $R^8$ was a Hydroxyl group, a more limited series of compounds could be made with the remaining positions of the following model compound (VIII):

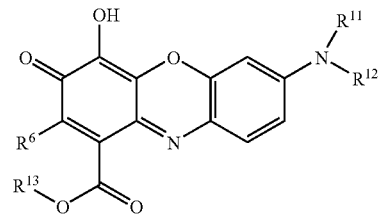

To initiate this series, a panel of compounds have been designed where $R^{11}$ and $R^{12}$ are methyl groups and $R^{13}$ is a hydroxyl group as in IIIC3 and the amine group was quarternized, giving the structure (VI):

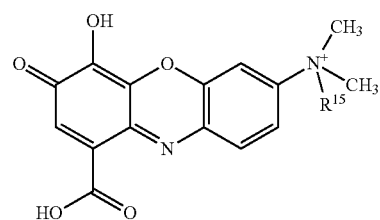

A series of substitutions have been designed for variations of $R^{15}$ in this compound using both linear and branched alkanes. The structures of the resultant compounds (EnzoM01-EnzoM12) are scanned as described previously to obtain a score for their likelihood of binding. A list of the particular substitutions used in EnzoM01-EnzoM12 as well as the resultant Cscore ratings are given below:

TABLE VIII

| Compound | R15 | Cscore |
|---|---|---|
| IIIC3 | — | 4 |
| EnzoM01 | CH3 | 5 |
| EnzoM02 | CH2CH3 | 5 |
| EnzoM03 | (CH2)2CH3 | 5 |
| EnzoM04 | CH(CH3)2 | 4 |
| EnzoM05 | (CH2)3CH3 | 3 |
| EnzoM06 | CH2CH(CH3)2 | 5 |
| EnzoM07 | CH(CH3)(CH2CH3) | 4 |
| EnzoM08 | C(CH3)3 | 4 |
| EnzoM09 | (CH2)4CH3 | 4 |
| EnzoM10 | (CH2)2CH(CH3)2 | 4 |
| EnzoM11 | CH2CH(CH3)(CH2CH3) | 5 |
| EnzoM12 | CH2C(CH3)3 | 5 |

In another approach, the carboxyl group of NCI 8642 is replaced by a carboxamide group to generate a series of compounds with the general structure (VII):

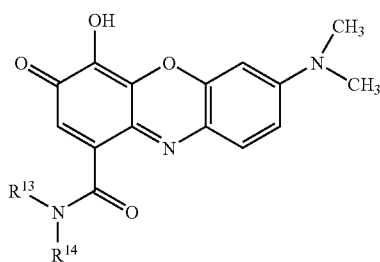

A list of the particular substitutions used in this series (EnzoM13-EnzoM41) as well as the resultant scores are given below:

TABLE IX

| Compound | R13 | R14 | Cscore |
|---|---|---|---|
| EnzoM13 | H | H | 5 |
| EnzoM14 | H | CH3 | 5 |
| EnzoM15 | CH3 | CH3 | 5 |
| EnzoM16 | H | CH2CH3 | 5 |
| EnzoM17 | H | (CH2)2CH3 | 5 |
| EnzoM18 | CH3 | CH2CH3 | 4 |
| EnzoM19 | CH3 | (CH2)2CH3 | 5 |
| EnzoM20 | H | C(CH3)3 | 5 |
| EnzoM21 | H | (CH2)3CH3 | 5 |
| EnzoM22 | CH3 | (CH2)3CH3 | 5 |
| EnzoM23 | H | CH2CH(CH3) | 5 |
| EnzoM24 | CH3 | CH2CH(CH3)2 | 5 |
| EnzoM25 | CH3 | C(CH3)3 | 5 |
| EnzoM26 | CH2CH3 | (CH2)2CH3 | 5 |
| EnzoM27 | CH2CH3 | CH(CH3)2 | 5 |
| EnzoM28 | CH2CH3 | (CH2)3CH3 | 5 |
| EnzoM29 | CH2CH3 | CH2CH(CH3)2 | 3 |
| EnzoM30 | CH2CH3 | (CH2)3CH3 | 5 |
| EnzoM31 | CH2CH3 | CH2CH(CH3)2 | 3 |
| EnzoM32 | CH3 | (CH2)4CH3 | 5 |
| EnzoM33 | CH3 | (CH2)2CH(CH3)2 | 5 |
| EnzoM34 | H | (CH2)4CH3 | 5 |
| EnzoM35 | H | (CH2)2CH(CH3)2 | 5 |
| EnzoM36 | CH2CH3 | (CH2)4CH3 | 5 |
| EnzoM37 | CH2CH3 | (CH2)2CH(CH3)2 | 5 |
| EnzoM38 | CH2CH3 | CH2CH(CH3)(CH2CH3) | 2 |
| EnzoM39 | H | CH2CH(CH3)(CH2CH3) | 5 |
| EnzoM40 | H | CH2C(CH3)3 | 2 |
| EnzoM41 | CH2CH3 | CH2C(CH3)3 | 4 |

In another series of compounds, the carboxyl group is esterified to give the structure (VIII):

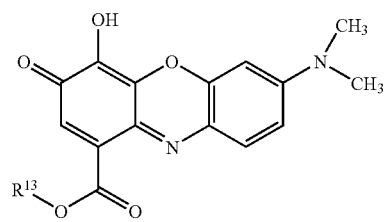

A panel of compounds (EnzoM42-EnzoM70) were designed with various groups; these substitutions and cScores are given below:

TABLE X

| Compound | R13 | Cscore |
|---|---|---|
| EnzoM42 | CH3 | 3 |
| EnzoM43 | CH2CH3 | 5 |
| EnzoM44 | (CH2)2CH3 | 5 |
| EnzoM45 | CH(CH3)2 | 5 |
| EnzoM46 | (CH2)3CH3 | 5 |
| EnzoM47 | CH2CH(CH3)2 | 5 |
| EnzoM48 | CH(CH3)(CH2CH3) | 5 |
| EnzoM49 | C(CH3)3 | 5 |
| EnzoM50 | ▷ (cyclopropyl) | 5 |
| EnzoM51 | (cyclohexyl) | 5 |
| EnzoM52 | (cyclopentyl) | 5 |
| EnzoM53 | CH2–phenyl | 2 |
| EnzoM54 | (trimethylcyclohexyl) | 5 |
| EnzoM55 | (dimethylcyclopentyl) | 2 |
| EnzoM56 | (dimethylcyclopropyl) | 4 |
| EnzoM57 | (tetramethylcyclopropyl) | 3 |

TABLE X-continued

| Compound | R¹³ | Cscore |
|---|---|---|
| EnzoM58 | 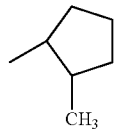 | 2 |
| EnzoM59 | 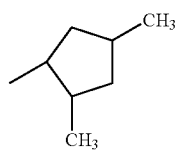 | 4 |
| EnzoM60 | 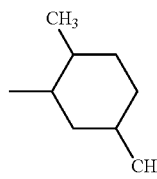 | 5 |
| EnzoM61 | 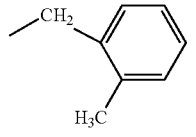 | 2 |
| EnzoM62 | 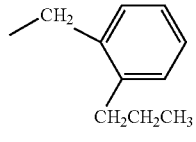 | 2 |
| EnzoM64 | 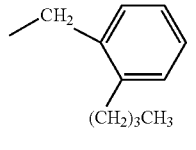 | 2 |
| EnzoM65 | 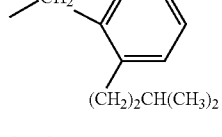 | 2 |
| EnzoM66 | $(CH_2)_4CH_3$ | 5 |
| EnzoM67 | $(CH_2)_2CH(CH_3)_2$ | 5 |
| EnzoM68 | $CH_3CH(CH_3)(CH_2CH_3)$ | 5 |
| EnzoM70 | $CH_2C(CH_3)_3$ | 4 |

It can be seen that the variety of substitutions that have been made in just three sites on the core molecule were able to generate a large number of candidates that can be tested by virtual screening without synthesizing a single molecule. Furthermore, when this series of compounds were tested in the same virtual screening program described previously, 44 out of the 70 compounds gave cScore values of 5. This demonstrates the power of the virtual substitution technique in designing new compounds since the compound IIIC3 used to design these molecules only had a relative cScore rating of 4.

Example 7

Refinement of Scores

Although all of the compounds that achieved high cScores in the previous example are candidates for testing, it would be more efficient to synthesize and test the ones that are the most likely to be effective. Since there was so many that had ratings of 5 (the highest potential cScore), a different criterion has to be used to sort the compounds out. In computing the cScore, various component scores are compiled together to achieve a final rating. In the original screening of the NCI library, the template compound, NCI 18642 (IIIC3), showed the highest rating of one of these components, the FR-Score. As such, this component score was used to rank the various analogs of the core compound that had cScores of 5. When viewed this way, 7 of the 44 candidates scored higher than the original NCI 18642. The values for these compounds (as well as those for IIIC3) are given below in Table XI.

TABLE XI

| Compound | FR-Score | GR-Score | PMFR-Score | DR-Score | Chemscore | cScore |
|---|---|---|---|---|---|---|
| EnzoM14 | −17.76 | −156.56 | −74.49 | −94.41 | −27.04 | 5 |
| EnzoM15 | −16.59 | −130.66 | −72.09 | −94.78 | −27.46 | 5 |
| EnzoM25 | −16.31 | −162.33 | −72.71 | −108.31 | −30.04 | 5 |
| EnzoM12 | −16.19 | −183.24 | −107.71 | −103.93 | −28.91 | 5 |
| EnzoM01 | −15.57 | 158.54 | −93.24 | −91.66 | −27.32 | 5 |
| EnzoM39 | −15.57 | 182.99 | −82.66 | −106.61 | −27.99 | 5 |
| EnzoM35 | −15.23 | 172.59 | −84.19 | −104.16 | −28.42 | 5 |
| IIIC3 | −14.79 | −124.58 | −71.08 | −73.64 | −26.28 | 4 |

This approach again shows the ability of screening a virtual library to identify promising candidates that would be worth synthesizing and testing in biological assays. Due to their higher rankings, it is possible that such candidates may demonstrate more potency than the original compounds that defined a core structure.

Example 8

Synthesis of Compounds Selected from Example 7

Synthesis of compounds selected by the virtual screening steps described above can be carried out by a number of means known in the art. For instance, these compounds may be created by taking a similar compound and substituting chemical groups by one or more replacement steps. In an example of this, IIIC3 (NCI 18642) is commercially available as gallocyanine and can serve as a starting point for many substitutions. Alternatively, precursors of the desired compound can be synthesized with the appropriate R groups and joined together to synthesize a candidate to be tested in a biological assay.

(A) Synthesis of EnzoM15

To a solution of 6.02 g of gallocyanine (free of hydrochloride) in 40 ml of DMF was added 6.62 g of succinimido-1,1,3,3-tetramethyluronium tetrafluoroborate followed by 6.96 ml of diisopropylethylamine and stirred overnight at room temperature. After removal of DMF, the residue was resuspended in 10 ml of anhydrous THF and then 10 ml of 2M dimethylamine in TMF was added. The mixture was heated at 50-60° C. for 5 hours. The product was purified by column chromatography using silica gel ($CH_2Cl_2$/1% MeOH) to give 0.8 g (12% yield) of EnzoM15 (shown below).

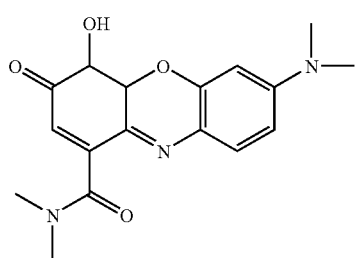 [SMILES: CN(C)C(=O)C1=CC(=O)C(O)C2Oc3cc(N(C)C)ccc3N=C12]

(B) Synthesis of EnzoM14

The synthesis of EnzoM14 was carried out basically as described for EnzoM15 except that 100 ml of methylamine was substituted for the dimethylamine used in the synthesis of EnzoM15. The heating step was also increased from 5 hours to overnight instead. Purification on silica gel was carried out as described above to give 0.75 g (12% yield) of EnzoM14 (shown below).

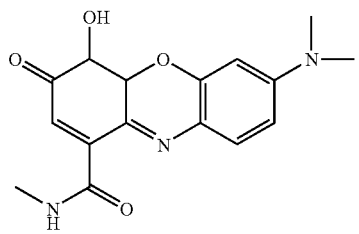 [SMILES: CNC(=O)C1=CC(=O)C(O)C2Oc3cc(N(C)C)ccc3N=C12]

(C) Synthesis of EnzoM01

Step 1. Synthesis of Methyl Iodide

A three necked flask with a stirring magnet was fitted with a thermometer, a separatory funnel and a small fractionating column connected with a condenser set for downward distillation and a receiving flask kept in an ice water bath. A solution was made by dissolving 800 g (4.8 moles) of potassium iodide in 430 ml of water and this was added to the flask. 60 g of calcium carbonate was then added and the mixture heated to 60-65° C. with stirring. The temperature was maintained at 60-65° C. and then 630 g (473 ml, 5 moles) of "practical" methyl sulfate was gradually added through the separatory funnel over a period of 2 hours. The rate of addition of the calcium carbonate was maintained to keep distillation of methyl iodide product proceeding into the receiving flask. After all of the calcium carbonate had been added, the temperature was raised to 65-70° C. for about 40 minutes to complete distillation of the methyl iodide. The product was separated from a small amount of water residue and then the product was dried over anhydrous calcium chloride followed by decanting the methyl chloride into a dry distilling flask. A few crystals of potassium iodide were added and the product distilled from a water bath. The redistilled product gave a yield of 615-640 g (a 90-94% yield) and had a boiling point of 41-43° C.

Step 2. Addition of Methyl Group to Gallocyanine 1.5 g of gallocyanine (chloride free) was dissolved in 500 ml of DMF in a 1000 ml flask. The mixture was stirred at 30° C. for 1 hour and then 10 ml of the methyl iodide made in the step above was added. The solution was then heated and refluxed with stirring for 72 hours, the condenser pipe was sealed with a balloon and additional 10 ml of methyl iodide was added every 12 hours. The THF was then distilled off at 80° C. The remaining solid (EnzoM01) gave a yield of about 98%.

A mixture of 100 mg (0.33 mMoles) of gallocyanine (chloride free), 50 ml of methanol, 38 μl (0.33 mMoles) of 2,6-lutidine and 0.5 ml of methyl iodide were placed in a pressure vessel with stirrer. The mixture was stirred and heated at about 100° C. for 4 days. After concentration in vacuo, the residue was washed with 5 ml of ethanol. Filtration gave 91 mg of solid product. The structure of EnzoM01 is given below:

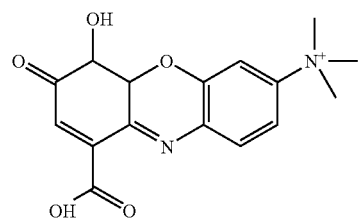 [SMILES: C[N+](C)(C)c1ccc2c(c1)OC1C(=N2)C(C(=O)O)=CC(=O)C1O]

(D) Synthesis of EnzoM02

Since EnzoM01 showed interesting results (results shown in Examples below), a related compound, EnzoM02, that had a FR-Score lower than the original IIIC3, was also chosen for synthesis and biological testing. The compound EnzoM02 is essentially similar to EnzoM01 except that an ethyl group replaces one of the methyl groups on the quarternized nitrogen. As such, EnzoM02 was made essentially as described for EnzoM1 except that the quarternization took place with ethyl iodide instead of methyl iodide and it was carried out on a smaller scale. A mixture of 100 mg (0.33 mMoles) of Gallocyanine (chloride free), 50 ml of methanol, 38 μl (0.33 mMoles) of 2,6-lutidine and 0.5 ml of methyl iodide were placed in a pressure vessel with stirrer. The mixture was stirred and heated at about 100° C. for 4 days. After concentration in vacuo, the residue was washed with 5 ml of ethanol. The yield of filtration product was 134 mg and the structure of EnzoM02 is shown below:

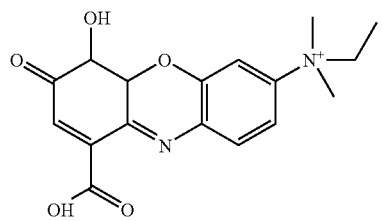 [SMILES: CC[N+](C)(C)c1ccc2c(c1)OC1C(=N2)C(C(=O)O)=CC(=O)C1O]

(E) Synthesis of EnzoM03

Another compound EnzoM03 that was related to EnzoM01 (but like Enzo M02 in having an FR-Score lower than IIIC3) was chosen for synthesis. The compound EnzoM03 differs from EnzoM01 by having a propyl group instead of a methyl group on the quarternized nitrogen. As such, the compound EnzoM03 was made essentially as described for EnzoM02 except that the quarternization took place with propyl iodide instead of ethyl iodide. The yield of filtration product was 138 mg and the structure of EnzoM03 is shown below:

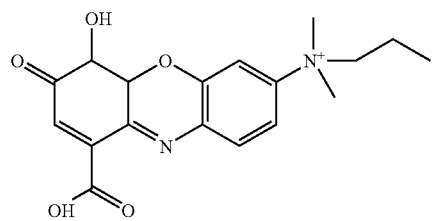 [SMILES: CCC[N+](C)(C)c1ccc2c(c1)OC1C(=N2)C(C(=O)O)=CC(=O)C1O]

Example 9

Testing Compounds Synthesized in Example 8

Figure 21:
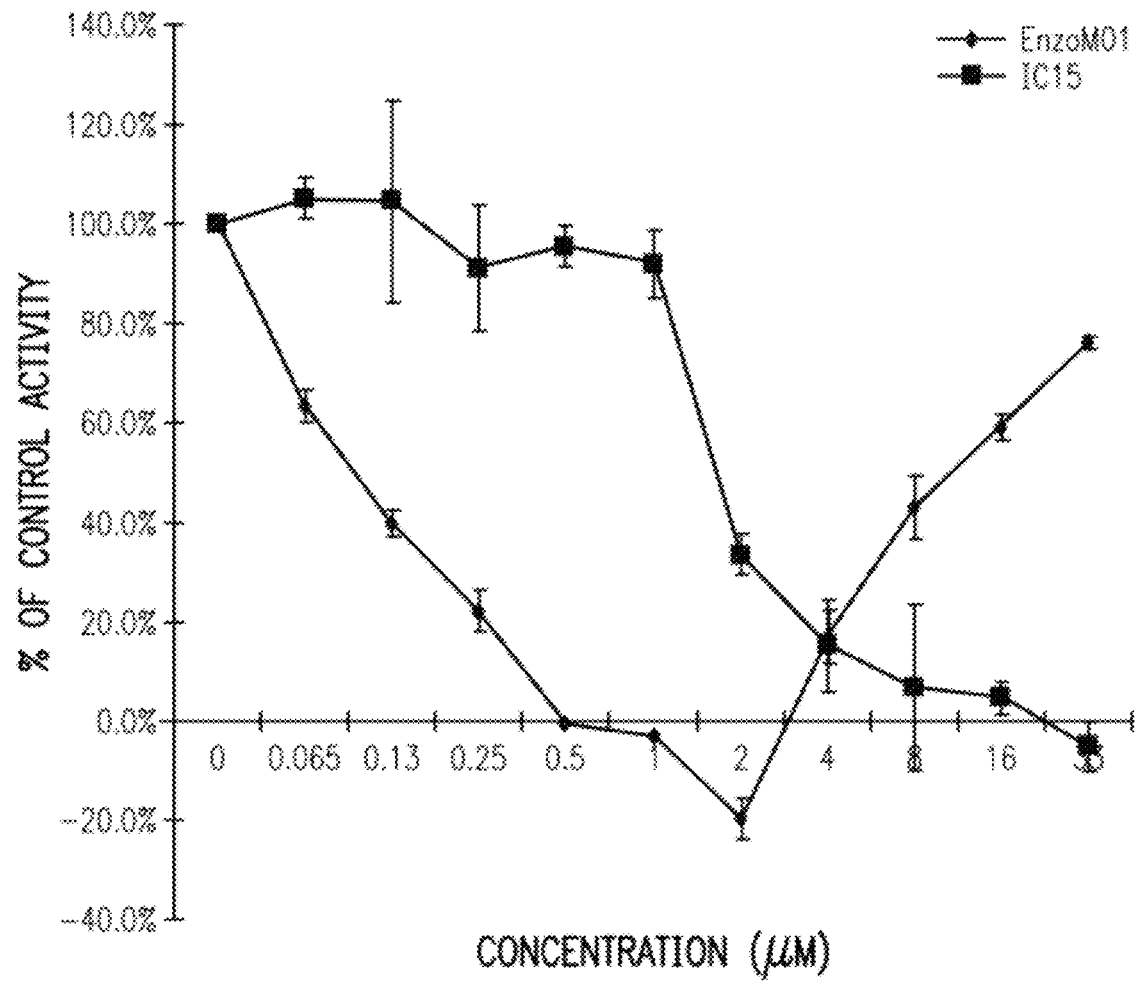
FIG. 21 shows the effects of EnzoM01 and IC15 on the inhibition of Wnt-stimulated beta-catenin activity.

After synthesis of the compounds described in Example 8, they were tested as described previously for Wnt activity and effects on Dkk inhibition. Additionally, the previous screening had used a single concentration of the test compound in the assays. Since a smaller number of compounds were being tested in this example, a variety of different inputs for each test compound could be tested simultaneously for Wnt activity. The results of various concentrations of EnzoM01 are shown in FIG. 21 and as a comparison, a titration with IC15 is also included. It can be seen for both EnzoM01 and IC15, there is a dose response for effects upon Wnt activity. However, the same level of inhibition of Wnt activity seen by IC15 can be seen at a dose of EnzoM01 that is approximately 15 times less. It can also be seen that at higher levels of EnzoM01 (8.33 μM and greater) there is a change in the effect upon Wnt activity, possibly indicating a more complex response to this drug. An HPLC analysis of this particular EnzoM01 preparation also showed it to be contaminated with a small amount of unreacted gallocyanine which may also be a factor at the higher dosages.

Figure 22:
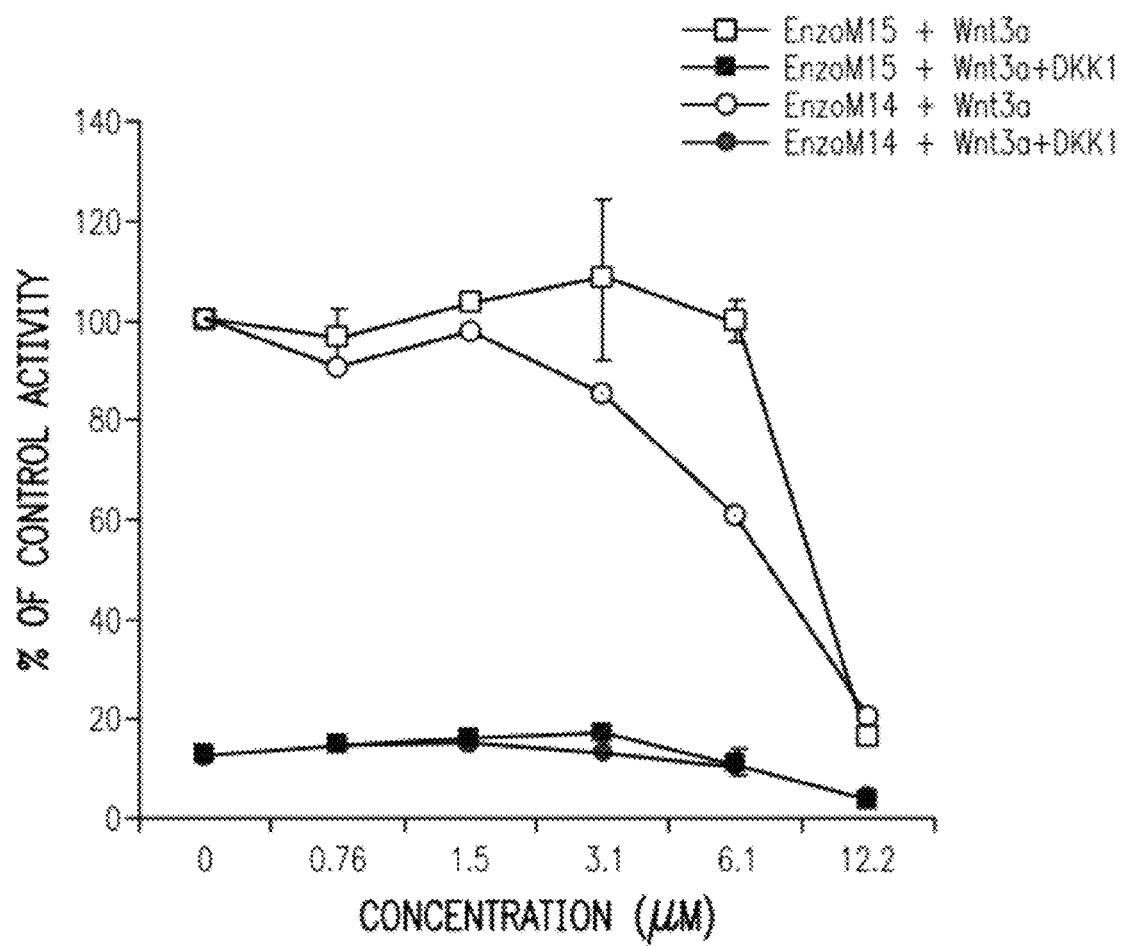
FIG. 22 shows the inhibition of Wnt-stimulated beta-catenin activity by both EnzoM14 and EnzoM15.

In FIG. 22, the results are shown for EnzoM14 and EnzoM15. In this experiment, EnzoM14 shows a dose response for reduction of Wnt activity whereas EnzoM15 shows a more abrupt response after 6.1 μM. It can also be seen that these compounds have no apparent effect on Dkk-mediated inhibition of Wnt activity.

Figure 23A:
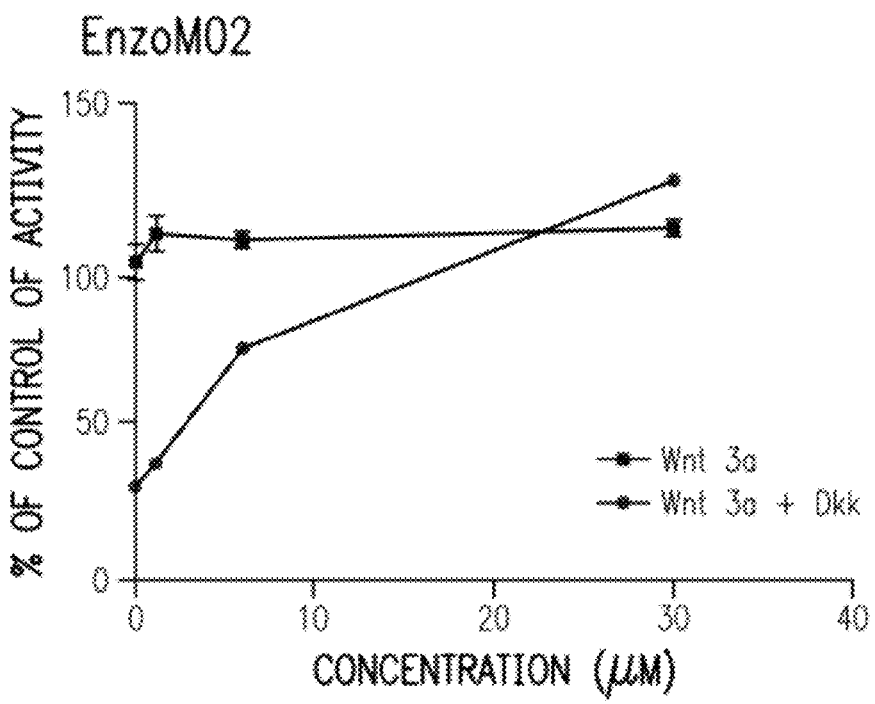
FIG. 23 shows the reversal of Dkk1 inhibition of Wnt signaling activity by EnzoM02 (FIG. 23A) and EnzoM03 (FIG. 23B).
Figure 23B:
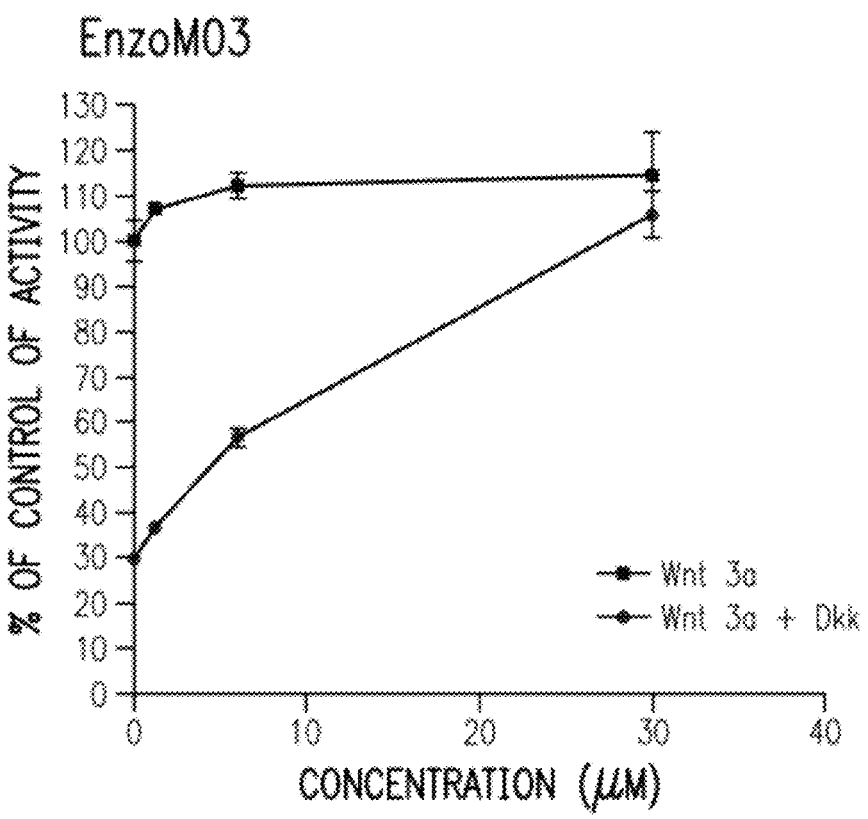

In FIG. 23, the results are shown for EnzoM02 and EnzoM03 with essentially similar results for each compound. At the concentrations used in this experiment there was very slight effects upon Wnt activity itself. However, at the highest concentrations used (6 μM and 30 μM), these compounds demonstrated an ability to decrease the effects of Dkk on Wnt activity.

Example 10

Effects of Various Compounds on the Viability of a Tumor Cell Line

As described above, the Wnt pathway has been linked to the development and progression of cancer. Three of the compounds that have been discovered to affect Wnt activity (IC15, IIIC3 and EnzoM01) were applied to a tumor cell line (PC-3) growing in vitro.

Figure 24A:
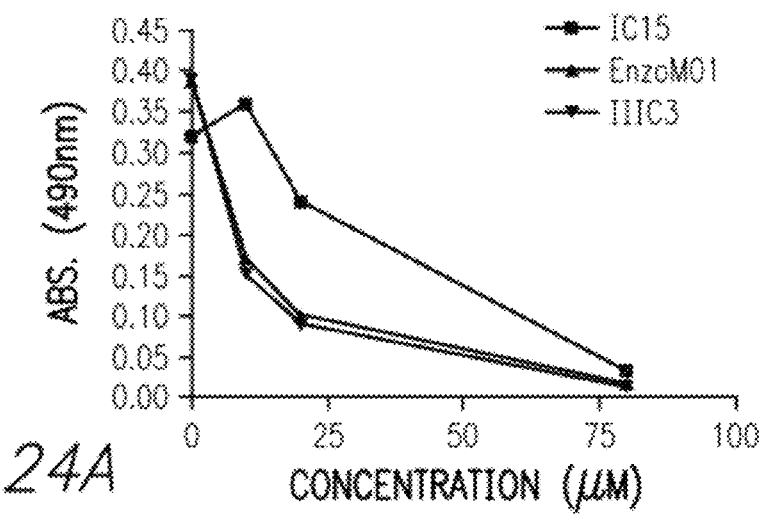
FIG. 24 shows the effects of three compounds on the viability of PC-3 tumor cells at different cell densities: (A) 500 cells/well, (B) 1000 cells/well and (C) 2000 cells/well.
Figure 24B:
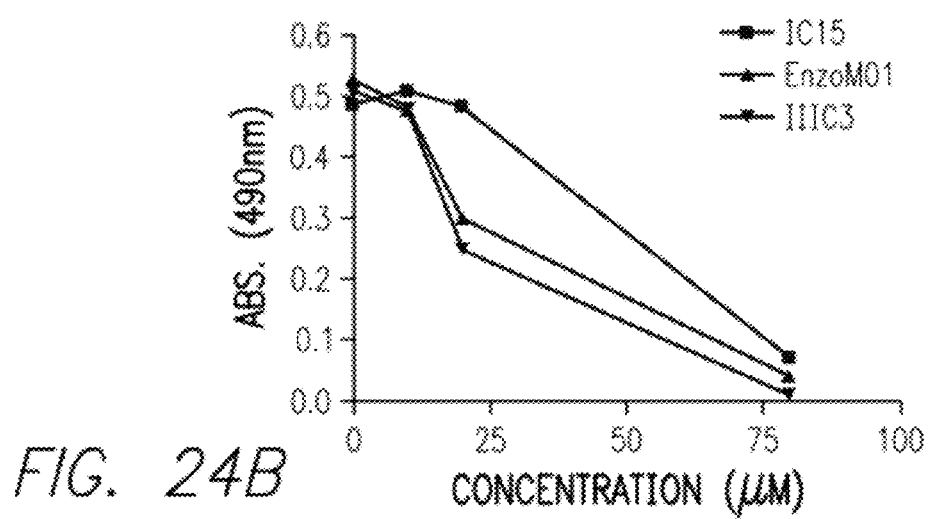
Figure 24C:
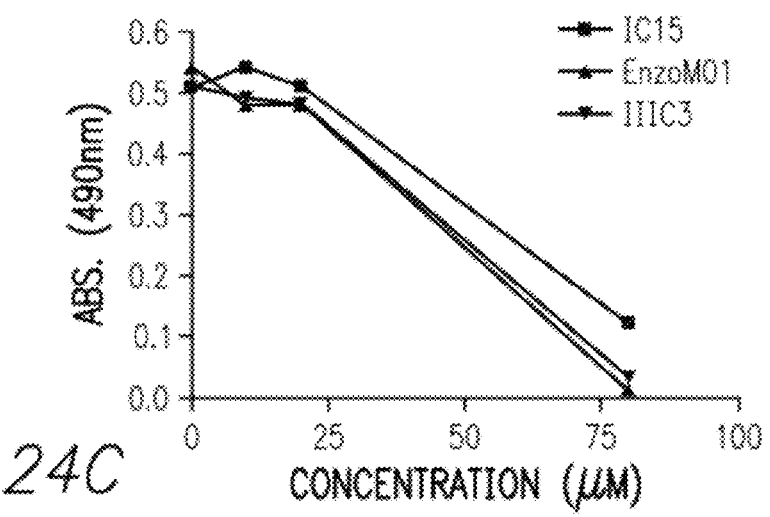

PC-3 tumor cells were seeded into a 96 well plate with: A) 500 cells/well; B) 1000 cells/well; and C) 2000 cells/well with Ham's F12 medium supplemented with 10% FBS. Various amounts of IC15, IIIC3 or EnzoM01 (10 μM. 20 μM or 80 μM final) were added to the media and growth continued for 10 days. Media was removed, the cells were washed with PBS and then incubated with RPMI media (without Phenol Red) containing 20% Cell titer 96 Aqueous One Solution Reagent (Promega, Madison, Wis.) for four hours. Cellular proliferation was then measured by absorbance according to the manufacturer's directions. The results of this assay are shown in FIG. 24. The presence of these compounds seemed to have a profound effect upon the number of viable PC-3 cells present at the end of the experiment, however, the effects of the drug was dependent upon the initial plating density. At the lowest density (500 cells/well) IIIC3 and EnzoM01 showed a decrease in the number of viable cells at 10 μM and IC15 showed an effect at 20 μM. In the 1000 cell/well samples, IIIC3 and EnzoM01 show a 10% and 15% reduction in the number of viable cells at the 10 μM level, respectively, and approximately a 50% reduction at the 20 μM level; whereas, IC15 shows a reduction only at the highest concentration tested, 80 μM. At the highest cell density tested (2000 cells/well) all three compounds demonstrated cytotoxicity at levels greater than 20 μM of test compounds were present. In conclusion, this example demonstrates that three different compounds selected for an ability to a) bind to LRP 5/6 and b) affect Wnt activity are capable of reducing the ability of a cancer cell line to proliferate.

Example 11

Effects on β-catenin Activity

The protein β-catenin is considered to be a major downstream target of the Wnt pathway. It had previously been noted that a number of cell lines derived from tumors have elevated levels of β-catenin compared to normal cells. In fact, various mutations and deletions in the apc (adenomatous polyposis coli) gene, which directly regulates β-catenin activity, has been strongly linked with the development of colon cancer. For instance, mice strains that have been genetically engineered to have defects in the apc gene ("multiple intestinal neoplasia" or "min" strains) are genetically predisposed to develop a large number of intestinal tumors as they age.

A number of different tumor cell lines were tested for the effects of EnzoM01 on expression of β-catenin as measured by an ELISA assay. The tumor lines were derived from different tissue types: ovarian cancer (PA-1), prostate cancer (PC-3), breast cancer (HTB-24 and HTB26) and colon cancer (Lys174T).

A) Cell Growth

The various cell lines listed above were grown to about 70% confluency and then various amounts of EnzoM01 were added and incubated for 16 hours. The media was removed, the cells harvested and cellular lysates were used for ELISA assays to measure (β-catenin.

B) ELISA Assay

Wells of a 96 well plate were coated with capture antibody, an anti-β-catenin monoclonal antibody (BD Bioscience, San Diego Calif.), in sodium carbonate, pH 9.0 overnight at 4° C. The next day, the wells were washed once with TBST (Tris buffered saline containing 0.02% Tween 20) and incubated with 1% BSA blocking solution for 1 hour at room temperature. Wells were washed once with TBST and cell lysates added and incubated at room temperature for 1 hour. Wells were then incubated with anti-β-catenin polyclonal antibody (BD Bioscience, San Diego, Calif.) at room temperature for 45 minutes. Wells were washed three times with TBST and then a peroxidase conjugated antiRabbit IgG secondary antibody (Cell Signaling Technology, Danvers, Mass.) was added to each well and incubated for 25 minutes. Wells were washed three times with TBST and fluorescence was developed by incubating with 1:1 mix of SuperSignal West Pico Stable Peroxide Solution (Pierce Biochemicals, Rockford, Ill.).

C) Results

Figure 25A:
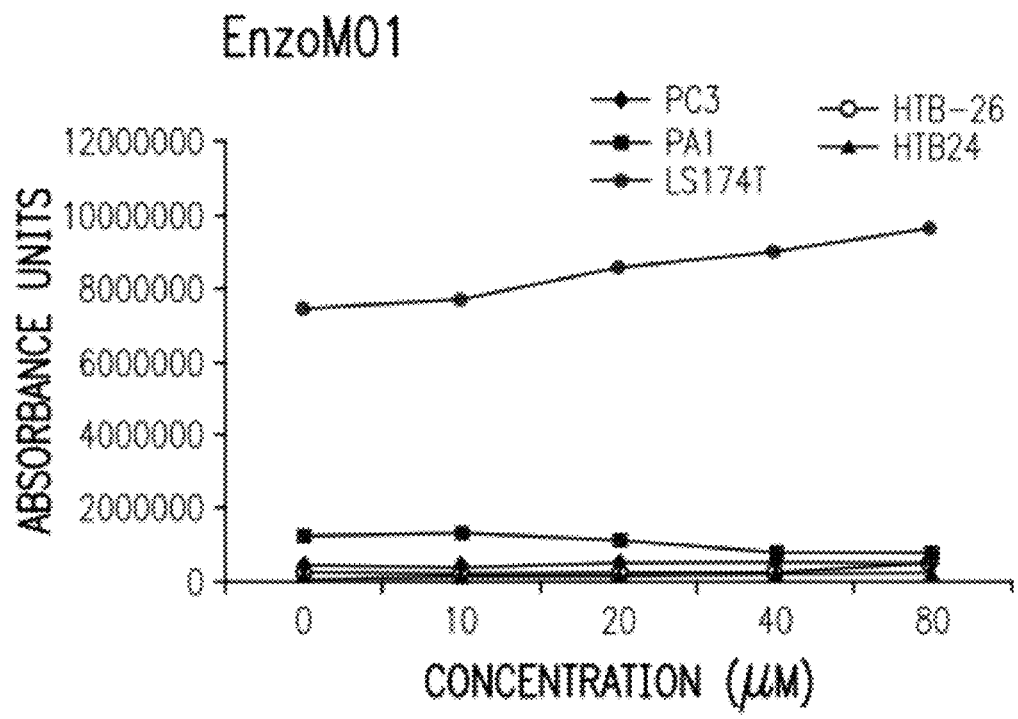
FIGS. 25A and B show the effects of EnzoM01 on beta-catenin production in different tumor cell lines.
Figure 25B:
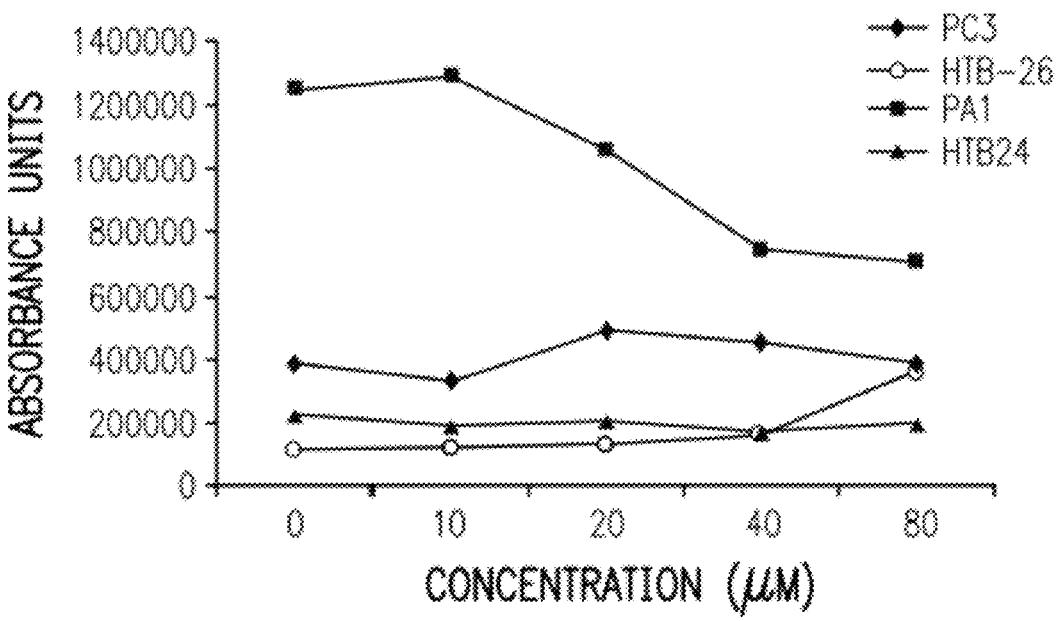

The results of this experiment are shown in FIG. 25A. It can be seen that the intrinsic level of β-catenin in LS174T is much higher compared to the other cell lines and that there is a slight but dose-responsive effect upon LS174T by EnzoM01 at the dosages used where β-catenin activity actually increases as the dosage goes up. However, since the activity of β-catenin is so high in this cell line, it obscures the effects on the other cell lines that have much lower intrinsic levels of β-catenin activity. Accordingly, this data is also presented with the LS174T data omitted in FIG. 25B. It can be seen that although there was essentially no change in β-catenin levels in the breast cancer cell lines HTB-26 and HTB24 as well as the prostate cancer cell line PC-3, there was a selective reduction of β-catenin levels in the ovarian cell line PA1 at the higher doses of EnzoM01. The IC50 value for EnzoM01 was in the range of 20-40 μM.

Example 12

Effects of Various Compounds on Tumor Induction and Progression

In a study on the effects of diet upon induction and progression of colon tumors, apc$^{min/+}$ mice had been shown to respond to the presence or absence of a particular dietetic supplement, β-glucosylceramide (110). The ability of a reagent to influence the frequency or size of spontaneous tumors in this strain of mice presents an opportunity to test some of the previously identified compounds for their potential in affecting induction and progression of cancer in a live animal.

Compounds IC15 and IIIC3 were identified in the virtual screening process for a likelihood of binding to a selected site on LRP5. Both of these compounds were administered to groups of apc$^{min/+}$ mice and the size and frequency of tumors were measured at a later time point.

A) Treatment of Test Mice

In order to investigate the effectiveness of these two compounds in vivo, 8-9 week old C57BL/6J$^{APC(min+)}$/J were obtained from Jackson Laboratories (Bar Harbor, Me.). The mice were kept on a normal diet for 54 days at which time they were switched to a high fat diet for 36 days. At this point, the mice were injected with vehicle, 625 uM IIIC3 or 42 uM IC15 in a volume of 1 ml every other day for 90 days. At the end of the treatment period, the mice were sacrificed and their intestines removed and followed by staining with methylene blue to quantify the number and size of developing tumors in the intestines.

B) Results

The number of tumors of various sizes is given below in Table XII.

TABLE XII

| Treatment | Tumors of size 0-1.53 mm² | Tumors of size 1.53-3.0 mm² | Tumors of size 3.0-4.62 mm² | Tumors of size 4.62-6.15 mm² | Tumors of size 6.15-7.69 mm² | Tumors of size >7.69 mm² | Total Tumors |
|---|---|---|---|---|---|---|---|
| Vehicle | 20.7 ± 2.08 | 18.57 ± 2.98 | 11.43 ± 3.44 | 4.71 ± 0.89 | 2.57 ± 0.37 | 1.43 ± 0.48 | 59.43 ± 8.18 |
| IIIC3 | 7.5 ± 1.38 | 10.33 ± 1.48 | 6.50 ± 0.96 | 2.5 ± 0.67 | 2.5 ± 0.5 | 2.33 ± 0.67 | 31.67 ± 3.49 |
| 1C15 | 9.33 ± 1.33 | 16.00 ± 0.58 | 4.67 ± 1.45 | 3.3 ± 0.88 | 3.7 ± 1.87 | 1.33 ± 0.33 | 38.33 ± 3.71 |

It can be seen that both of these compounds gave a decrease in the overall number of tumors. The average number of tumors on the test animals was 59.4 for the control and only 31.67 and 38.33 for the animals treated with IIIC3 and IC15 respectively. This shows a reduction of 47% and 36% after treatment with these compounds. It can also be seen that the effects of these compounds is seen more prominently with the smaller sized tumors than the larger tumors. This may be an indication that these compounds delay initiation but have less of an effect upon progression once a tumor has been established although other explanations are also possible.

Example 13

Effects of Various Compounds on Levels of Glucose, Insulin, Triglycerides and Cholesterol in Mice on a High Caloric Diet As has been discussed previously, LRP5/6 has been shown to play multiple roles in the Wnt signaling pathway, including the modulation of normal cholesterol and glucose metabolism. A group of C57BL/6J mice were initially maintained on a normal caloric diet for 5 days after which time they were fasted overnight and then blood glucose levels were assayed using a Lifescan glucometer (Johnson & Johnson). The animals were then placed on a high caloric diet for 10 days during which time they were simultaneously administered different concentrations of EnzoM01, IC15 and IIIC3 (0.02, 0.06 and 0.30 mg/kg/day for Enzo M01, 0.2, 0.6 and 3.0 mg/kg/day for IC15 and 0.5, 2.0 and 8.0 mg/kg/day for IIIC3). On the final day, animals were subjected to an overnight fast and then blood glucose levels were determined.

Results

Figure 26A:
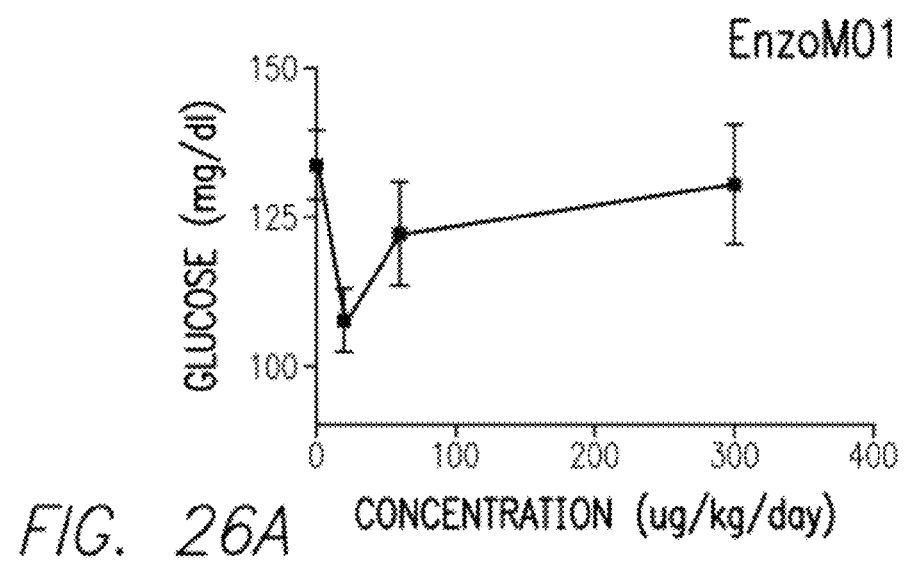
FIG. 26 shows the effect of EnzoM01 (FIG. 26A), IC15 (FIG. 26B) and IIIC3 (FIG. 26C) on glucose metabolism in mice subjected to a high caloric diet.
Figure 26B:
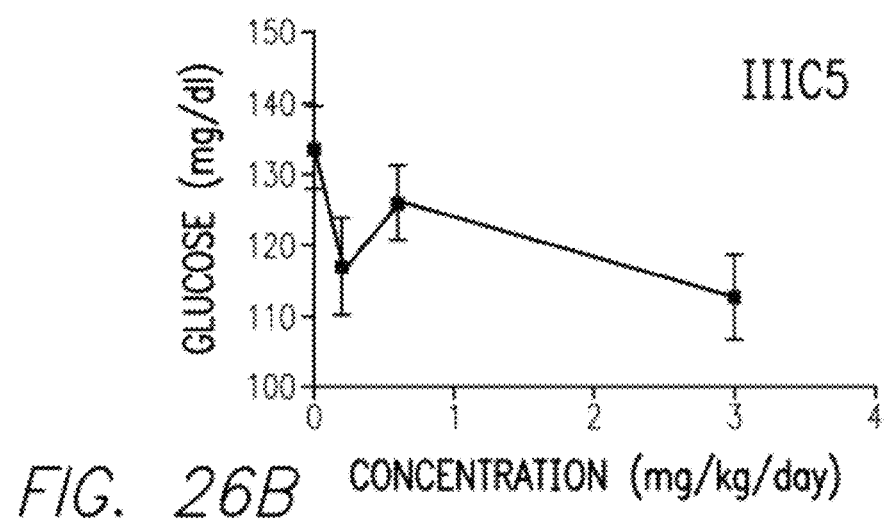
Figure 26C:
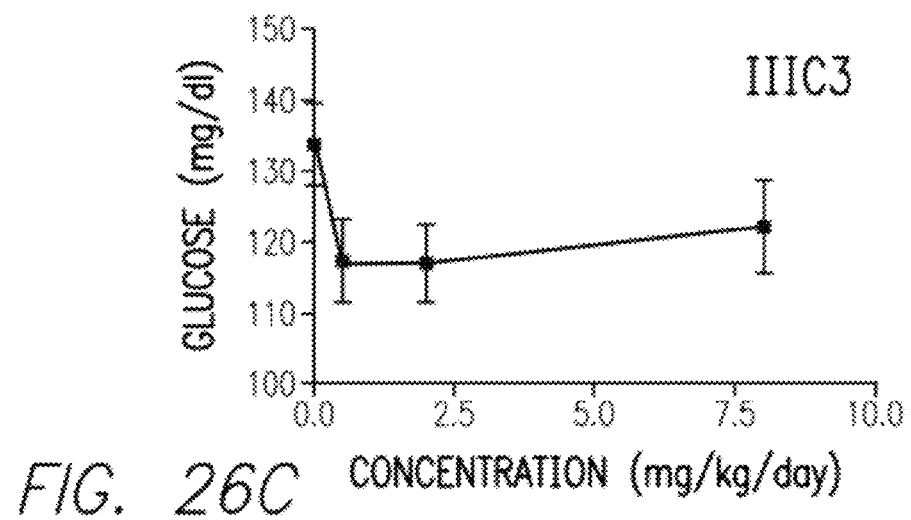
Figure 27A:
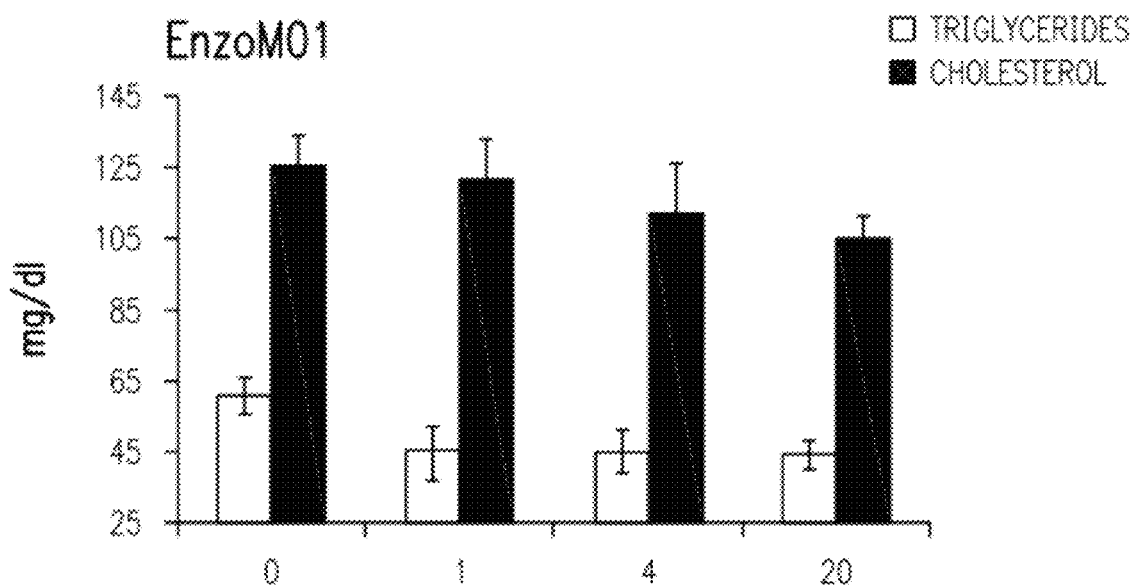
FIG. 27 shows the effect of (FIG. 27A) EnzoM01 and (FIG. 27B) IC15 on serum levels of triglycerides and cholesterol in high caloric diet fed mice.
Figure 27B:
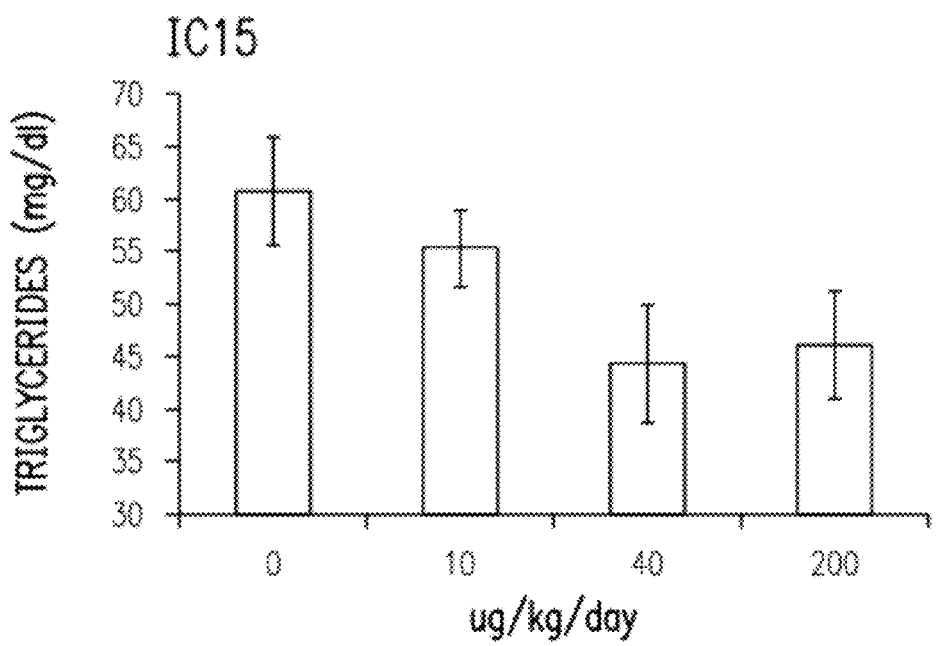

After feeding on a high caloric diet for 10 days, the control mice showed an approximately 30% increase in serum glucose levels. In FIG. 26 it can be seen that all three compounds differentially lowered blood glucose levels to varying degrees. At the highest concentrations used, both IIIC3 and IC15 brought blood glucose levels back to within 10% of normal, physiological serum values; whereas, treatment with EnzoM01 was most effective at a concentration of 0.02 mg/kg/day. These results demonstrate that all three compounds are capable of returning hyperglycemic mice back to normo-glycemic values without inducing hypoglycemia. In addition, blood samples were also analyzed for cholesterol and triglyceride levels. This was carried out by submitting serum samples to a clinical laboratory (Enzo Laboratories, Farmingdale, N.Y.) where they were measured the same way as if they were patient samples. As seen in FIG. 27A, EnzoM01, and in 27B, IC15, were effective in lowering triglyceride levels. At the concentrations used, it can also be seen in FIG. 27A that EnzoM01 was also effective in lowering cholesterol Example 14

Treatment of Diabetic Mice

In addition to investigating the effect these compounds have on normal mice fed a high caloric diet, markedly diabetic and insulin-resistant db/db mice (Jackson Laboratories, Bar Harbor, Me.) were tested with treatment with IIIC3. The db/db mouse is hyperleptinemic and develops obesity and severe type 2 diabetes partly due to a functional defect in the long-form leptin receptor, which plays a significant role in the regulation of food intake and the control of body weight (111, 112).

Figure 28A:
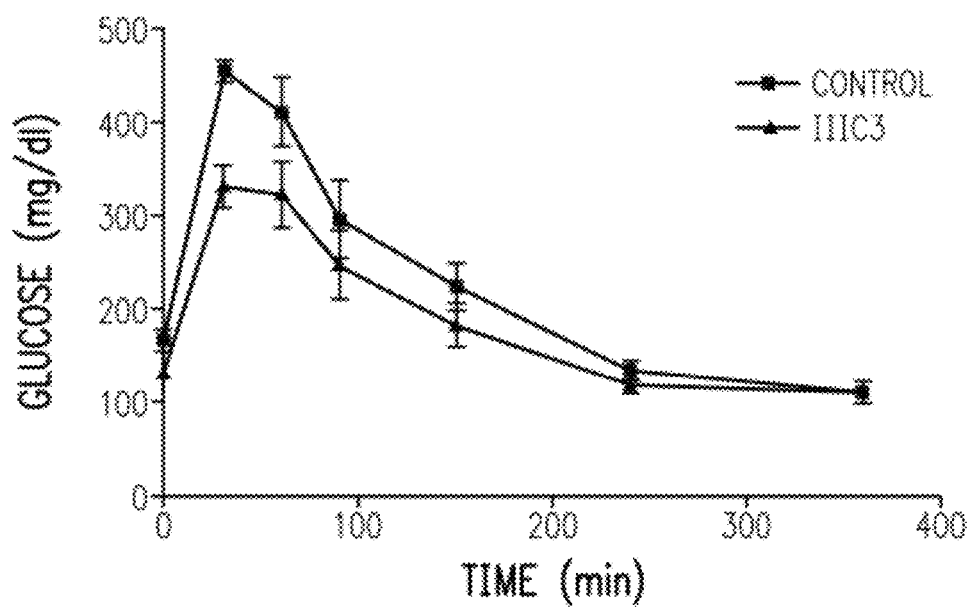
FIG. 28 shows the effect of IIIC3 on glucose (FIG. 28A) and insulin (FIG. 28B) levels in db/db mice.
Figure 28B:
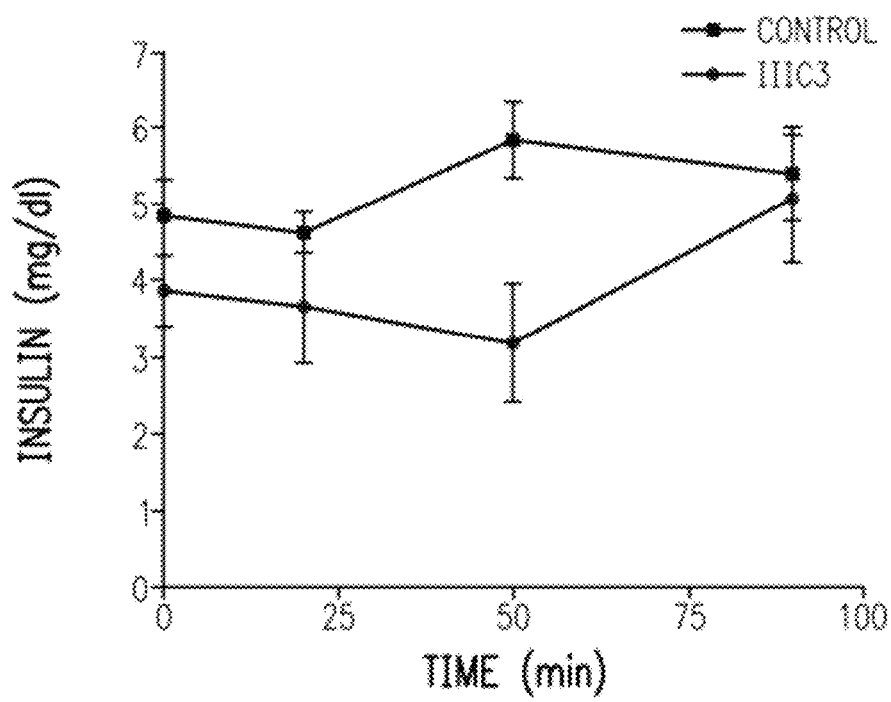

The diabetic prone mice were placed on a high caloric diet for 12 days during which time they were simultaneously administered 7 mg/kg/day of IIIC3. At the end of this treatment, the mice were fasted for 12 hours and the mice were then administered an IP injection of 1 g/kg glucose for a glucose tolerance test. At various times after the injection, glucose and insulin concentrations in the blood were analyzed with glucose being measured as described previously and insulin measured by the Insulin Ultrasensitive EIA (ALPCO Diagnostics, Salem, N.H.). As seen in FIG. 28A, the mice treated with IIIC3 demonstrated an improved ability for glucose disposal. This effect was also paralleled by a significant reduction of plasma insulin levels (FIG. 28B).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

REFERENCE LIST 1. 2001 NIH Consensus Conference Development Panel on Osteoporosis Prevention, Diagnosis and Therapy. JAMA 285:785-795.
2. Babij et al., 2003, J Bone Miner Res 18:960-74.
3. Bafico et al., 2001, Nat Cell Biol 3:683-6.
4. Bain et al., 2003, Biochem Biophys Res Commun 301:84-91.
5. Boyden et al., 2002, N Engl J Med 346:1513-21.
6. Capelluto et al. 2002, Nature 419(6908):726-9.
7. Cheyette et al. 2002, Dev Cell, Vol 2 449-461.
8. Clark et al. 2002, J. Mol. Graph.
9. Culi et al. 2003, Cell 112:343-54.
10. Dale et al. 1998, 329:209-223.
11. Daniels et al 2002, 10(3):573-84.
12. Dann et al. 2001, Nature, Vol. 412, 86-90.
13. Glinka et al, 1998, Nature 391:357-62.
14. Gong et. al. 2001, Cell 107:513-23.
15. Gumbiner et al. 1998, 8:430-5.
16. Graham et. al. 2000, Cell. 103(6):885-96.
17. Gruneberg, et al. 2001, Angew. Chem. Int. Ed Engl. 40, 389-393.
18. Hey et al. 1998. Gene. 216, 103-11.
19. Hsieh et al. 2003, Cell 112:355-67.
20. Hsu et al. 1998, Molecular and Cellular Biology 18:4807-4818.
21. Hurst. 1994, J. Chem. Inf. Comput. Sci. 34, 190-196.
22. Jeon et. al. 2001, Nat Struct Biol 8:499-504.
23. Kalajzic et. al. 2002, J Bone Miner Res 17:15-25.
24. Kannus et al. 2000, Osteoporos Int 11:443-8.
25. Katoet. al. 2002, J Cell Biol 157:303-14.
26. Krupnik et al. 1999, Gene 238:301-13.
27. Leyns et. al. 1997, Cell, Vol. 88 747-756.
28. Li et al. 2002, J Biol Chem 277:5977-81.
29. Li et al. 1999, EMBO J. 18:4233-4240.
30. Li et al. 1999, J. Biol. Chem. 274:129-134.
31. Lips 1997, Am J Med 103:3 S-8S; discussion 8S-11S.
32. Little et al. 2002, Am J Hum Genet. 70:11-9.
33. Love et al, 1995, Nature. 376(6543):791-5.
34. Mao et al. 2002, Nature 417:664-7.
35. Mao et al, Nature 411:321-5.
36. Mao et al, 2001, Mol Cell 7:801-9.
37. Monaghan 1999, Mech Dev 87:45-56.
38. Moon R T et al, 1997, Cell, Vol. 88, 725-728.
39. Nusse 2001, Nature 411:255-6.
40. Pandur et al, 2001, Bioessays 23:207-10.
41. Pfaffl 2001, Nucleic Acids Res 29:e45.
42. Pinson et al, 2000, Nature 407:535-538.
43. Poy 2001, Nat Struct Biol. 8(12):1053-7.
44. Rarey et al, (1996) J. Mol. Biol. 261: 470-489.
45. Schweizer et al, 2003, BMC Cell Biol 4:4.
46. Semenov et al, 2001, Curr Biol 11:951-61.
47. Takagi et al, 2003, Nature 424:969-74.
48. Tamai et al, 2000, Nature 407:530-5.
49. Tamai et al, 2004, Molecular Cell, Vol. 13, 149-156.
50. Tolwinski et al, 2003, et al, Dev Cell 4:407-18.
51. Van Wesenbeeck et al, 2003, Am J Hum Genet. 72:763-71.
52. von Kries et al, 2000, Nat Struct Biol. 7(9):800-7.
53. Waszkowycz, et al, 2001, IBM Systems J. 40, 360-376.
54. Wehrli, et al, 2000, Nature 407:527-30.
55. Wharton 2003, Dev Biol. 253(1):1-17.
56. Wodarz 1998, Annu. Rev. Cell Dev. Biol. 14:59-88.
57. Wong et al, 2003, Mol. Cell. 12(5):1251-60.
58. Wong et al, 2000, Nat Struct Biol. 7(12):1178-84.
59. Xing Y et al, 2003, Genes Dev. 2003 Nov. 15; 17(22): 2753-64.
60. Zuckerman1996, N Engl J Med 334:1519-25.
61. Reya et al, 2005 *Nature* 434: 843
62. Kleber et al, 2004 *Curr Opin Cell Bio*116:681
63. Logan et al, 2004 *Annu Rev Cell Dev Biol* 20: 781
64. Sancho et al, 2004 *Annu Rev Cell Dev Biol* 20: 695
65. Wang et al, 2004 *Curr Opin Genet Dev* 14: 533
66. Moon et al, 2004, *Nat Rev Genet.* 5:691
67. He et al, 2004, *Development* 131:1663.
68. Kawano et al, 2003 *J Cell Sci* 116: 2627
69. Zhang et al., 2004, *Mol Cell Biol* 24:4677
70. Fujino et al., 2003, *Proc Natl Acad Sci USA* 100: 229
71. Yamazaki et al, 2003, *Biochem Biophys Res Commun* 304: 229
72. Hoffmann et al., 1999, *J Med Chem* 42: 4422.
73. Kramer 1999, *Proteins* 37: 228
74. Mundy et al., 1999, *Science* 286: 1946
75 Dunstan et al., 1999, *J Bone Miner Res* 14:953
76. Li, et al, 2001, *Cell Mol Life Sci* 58: 2085
77. Smith, 1999, *Trends Biochem Sci* 24: 181
78. Yuan et al, 1999, *J. Biol. Chem.* 274: 30419
79. Li et al, 2002, JBC 277; 5977-5981
80. Li et al., 2005, JBC 280; 19883-19887
81. Wei et al. 2006, Cell 124; 1141-1154
82. Johnson et al., 2004, J Bone Disease and Mineral Research 19; 1749-1757
83. Hayt et al. 2005, JBC 280; 13616-13623
84. Kikuchi et al., 2006, Exp Molec. Med. 38; 1-10
85. Mi et al, 2005, J Cell Biochem 95; 328-338,
86. Semenov et al. 2005, JBC 280; 26770-26775
87. Logan et al, Annu. Rev. Cell Dev. Bio120; 781-810
88. Streeten et al., 2003, J Bone Miner Res 18
89. Kato et al. 2002, J Cell Biol 157; 303-314
90. Krane 2005, J Exp Med 201; 841-843
91. Krishnan et al., 2006, J Clin Invest 116; 1202-1
92. Nussse et al., 1982, Cell 31:99-109
93. Liang et al., 2003, Cancer cell 4:349-360
94. Weeraratna et al., 2002, Cancer Cell 1:279-288
95. Polakis 2000 Genes Dev 14: 1837-1851
96. Behrens and Lustig 2004 Int J Dev Biol 48: 477-487
97. Luu et al., 2004 Curr Cancer Drug Targets 4; 653-671
98. Bafico et al., 2004b Cancer Cell 6; 497-506
99. Janssens et al., 2006 Investigational New Drugs 24; 263-280
100. Tian et al. 2003 NEJM 349: 2483-2494
101. Oshima et al., 2005 Blood 106: 3160-3165
102. Toomes et al, 2004 Am. J. Hum. Genet. 74: 751-730

103. Niemann et al., 2004 Am J. Hum. Genet. 74: 558-563
104. Grant et al., 2006, Nature Genetics 38: 320-323
105. Rodova et al., 2002 J. Biol. Chem. 277: 29577-29583
106. Surendram et al., Am J Physiol Renal Physiol 282: F431-F441
107. Chilosi et al., 2003, Am J. Pathol. 162: 1495-1502
108. Cheon et al., 2002 Proc. Nat. Acad. Sci. (USA) 99: 6973-6978
109. Miyaoka et al., 1999 Schizophr. Res. 38:1-6
110. Symolon et al. 2004 J. Nutr. 134: 1157-1161
111. Chen H. et al Cell 84: 491-495, 1996
112. Lee G. H. *Nature* 379: 632-635, 1996

What is claimed is:

1. A compound having the structure (VI):

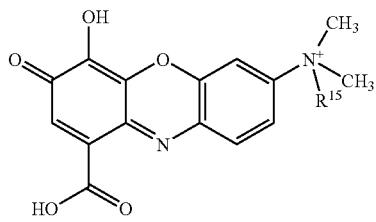

wherein $R^{15}$ is a linear or branched alkyl group.

2. The compound of claim 1, wherein $R^{15}$ is a linear or branched $C_{1-5}$ alkyl group.
3. The compound of claim 1, wherein $R^{15}$ is a methyl group.
4. The compound of claim 1, wherein $R^{15}$ is an ethyl group.
5. The compound of claim 1, wherein $R^{15}$ is a propyl group.
6. The compound of claim 1, wherein $R^{15}$ is $CH_2C(CH_3)_3$.
7. A composition comprising the compound of claim 1.
8. The compound of claim 1, wherein $R^{15}$ is $CH(CH_3)_2$.
9. The compound of claim 1, wherein $R^{15}$ is $(CH_2)_3CH_3$.
10. The compound of claim 1, wherein $R^{15}$ is $CH_2CH(CH_3)_2$.
11. The compound of claim 1, wherein $R^{15}$ is $CH(CH_3)(CH_2CH_3)$.
12. The compound of claim 1, wherein $R^{15}$ is $C(CH_3)_3$.
13. The compound of claim 1, wherein $R^{15}$ is $(CH_2)_4CH_3$.
14. The compound of claim 1, wherein $R^{15}$ is $(CH_2)_2CH(CH_3)_2$.
15. The compound of claim 1, wherein $R^{15}$ is $CH_2CH(CH_3)(CH_2CH_3)$.
16. The composition of claim 7, further comprising a pharmaceutically acceptable excipient.
17. The composition of claim 16, further comprising a second compound, wherein the second compound is a therapeutic agent.

* * * * *

UNITED STATES PATENT AND TRADEMARK OFFICE
CERTIFICATE OF CORRECTION

| | | |
|---|---|---|
| PATENT NO. | : 8,367,822 B2 | Page 1 of 1 |
| APPLICATION NO. | : 11/598916 | |
| DATED | : February 5, 2013 | |
| INVENTOR(S) | : Wu et al. | |

It is certified that error appears in the above-identified patent and that said Letters Patent is hereby corrected as shown below:

On the title page, item [60] under Related U.S. Application Data delete

"Provisional application No. 60/504,864, filed on Sep. 22, 2003."

and insert

--Provisional application No. 60/504,860, filed on Sep. 22, 2003.--

Signed and Sealed this
Thirteenth Day of May, 2014

Michelle K. Lee
*Deputy Director of the United States Patent and Trademark Office*